United States Patent
Gillespie et al.

(10) Patent No.: US 7,652,013 B2
(45) Date of Patent: Jan. 26, 2010

(54) INHIBITORS OF STEAROYL-COA DESATURASE

(75) Inventors: Paul Gillespie, Westfield, NJ (US); Robert Alan Goodnow, Jr., Gillette, NJ (US); Shawn David Erickson, Leonia, NJ (US); Richard Jones, Didcot (GB)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/328,874

(22) Filed: Dec. 5, 2008

(65) Prior Publication Data

US 2009/0149466 A1 Jun. 11, 2009

Related U.S. Application Data

(60) Provisional application No. 61/090,025, filed on Aug. 19, 2008, provisional application No. 61/007,154, filed on Dec. 11, 2007.

(51) Int. Cl.
C07D 239/47 (2006.01)
A61K 31/513 (2006.01)
(52) U.S. Cl. .................... 514/252.14; 544/295
(58) Field of Classification Search .......... 544/295; 514/252.14
See application file for complete search history.

(56) References Cited

U.S. PATENT DOCUMENTS

| 5,670,508 | A * | 9/1997 | Wang et al. ............. 514/272 |
| 6,562,970 | B1 | 5/2003 | Mais et al. |
| 2004/0254359 | A1 | 12/2004 | Crooke et al. |
| 2005/0059668 | A1 | 3/2005 | Alberati-Giani et al. |

FOREIGN PATENT DOCUMENTS

| WO | WO 03012031 | 2/2003 |
| WO | WO 2005/011655 | 2/2005 |
| WO | WO 2005014607 | 2/2005 |
| WO | WO 2006014133 | 2/2006 |
| WO | WO 2006/130986 | 12/2006 |

OTHER PUBLICATIONS

L. Zhang et al. *Biochem. J.* 1999, 340, 255-264.
J. Wang et al. *Biochem. Biophys. Res. Commun.* 2005, 332, 735-742.
M. H. Hulver et al. *Cell Metab.* 2005, 2, 251-261.
S. B. Biddinger et al. *Diabetes* 2005, 54, 1314-1323.
A. H. Gates and M. Karasek *Science* 1965, 148, 1471-1473.
M. Miyazaki et al. *J. Biol. Chem.* 2000, 275, 30132-31038.
P. Cohen et al. *Science* 2002, 297, 240-243.
J. M. Ntambi et al. *Proc. Natl. Acad. Sci USA* 2002, 99, 11482-11486.
G. Jiang et al. *J. Clin. Invest.* 2005, 115, 1030-1038.
D. J. Brown and J. S. Harper *J. Chem. Soc.* 1961, 1298-1303.
D. Isbecque et al. *Helv. Chim. Acta* 1959, 42, 1317-1323.
J. E. Arrowsmith et al. *J. Med. Chem.* 1989, 32, 562-568.
A. F. Abdel-Magid and S. J. Mehrman *Org. Process Res. Dev.* 2006, 10, 971-1031.

* cited by examiner

*Primary Examiner*—Deepak Rao
(74) *Attorney, Agent, or Firm*—George W. Johnston; Dennis P. Tramaloni; Samuel H. Megerditchian

(57) ABSTRACT

Provided herein are compounds of the formula (I):

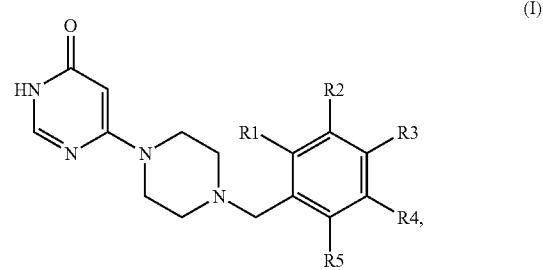

as well as pharmaceutically acceptable salts thereof, wherein the substituents are as those disclosed in the specification. These compounds, and the pharmaceutical compositions containing them, are useful for the treatment of diseases such as, for example, obesity.

19 Claims, No Drawings

INHIBITORS OF STEAROYL-COA DESATURASE

PRIORITY TO RELATED APPLICATION(S)

This application claims the benefit of U.S. Provisional Application No. 61/090,025, filed Aug. 19, 2008, and U.S. Provisional Application No. 61/007,154, filed Dec. 11, 2007. The entire contents of the above-identified applications are hereby incorporated by reference.

FIELD OF THE INVENTION

The invention relates to inhibitors of Stearoyl-CoA desaturase 1 (SCD1). The inhibitors are useful for the treatment of diseases such as, for example, obesity.

All documents cited or relied upon below are expressly incorporated herein by reference.

BACKGROUND OF THE INVENTION

Obesity is a condition that affects hundreds of millions of people. Obesity is associated with several very serious illnesses that can lead to decreased quality of life and in some cases to early death. Although there are multiple treatment options available for obesity, there is still a significant unmet medical need and a need for new therapies.

The World Health Organization (WHO) defines obesity using an index called the Body-Mass Index (BMI) which is defined as the weight of an individual in kilograms divided by the square of the height in meters. Individuals with a BMI greater than 25 $kg/m^2$ are considered overweight, while individuals with a BMI greater than 30 $kg/m^2$ are considered obese. Worldwide, approximately 1.6 billion adults are overweight and 400 million adults are obese, and these numbers are expected to increase [WHO Fact Sheet No. 311, September 2006].

Individuals with high BMIs are at risk of a number of serious complications, and the risk increases with BMI. Among the conditions associated with obesity are cardiovascular disease, diabetes, osteoarthritis, and certain cancers. These conditions cause a reduction in the ability of individuals to lead normal lives, and may lead to early death.

Obesity results from an imbalance between the intake of calories in food (for example, in carbohydrates and fats) and energy expenditure (for example, in exercise). A number of factors including genetic susceptibility have been found to contribute to the likelihood that an individual will become obese.

Stearoyl-CoA desaturase (SCD) is an enzyme which catalyzes the introduction of a cis double bond into saturated fatty acids to give monounsaturated fatty acids. Two of the most important substrates for the SCD enzymes are the Co-enzyme A esters of stearate and palmitate, which are converted into oleate and palmitoleate respectively. Oleate is the most common monounsaturated fatty acid found in membrane phospholipids, triglycerides, and cholesterol esters, and the ratio of saturated to unsaturated fatty acids affects membrane fluidity. The ratio of a monounsaturated fatty acid to the corresponding saturated fatty acid (for example, the ratio between oleate and stearate) is known as the desaturation index.

Several different isoforms of the SCD enzyme are known, and the number and tissue expression of the different isoforms vary across different species. For example, in the mouse, four different isoforms of the enzyme are known (SCD1, SCD2, SCD3, and SCD4), while in human two forms of SCD are known (SCD1 and SCD5). The homology between the human and mouse SCD1 proteins is 85% [L. Zhang et al. *Biochem. J.* 1999, 340, 255-264] while the two human isoforms of the protein have 75% homology. Human SCD1 is highly expressed in liver and especially in adipose tissue, while SCD5 has the highest levels of expression in brain and pancreas [J. Wang et al. *Biochem. Biophys. Res. Commun.* 2005, 332, 735-742].

The potential of SCD1 as a target for the treatment of obesity is shown from expression data in humans, from a naturally occurring mutation in mice, from an SCD1 knockout mouse, and by reducing the expression of the SCD1 protein using antisense oligonucleotides.

Transcriptional profiling of RNA from a small sample of lean and obese donors revealed that mRNA expression of SCD1 was elevated three-fold in the obese individuals while other genes involved in the oxidation of fatty acids, such as pyruvate dehydrogenase kinase 4, carnitine palmitoyltransferase 1β, and malonyl-CoA decarboxylase did not differ significantly between the two groups [M. H. Hulver et al. *Cell Metab.* 2005, 2, 251-261]. Furthermore, the SCD1 mRNA levels showed a positive association with BMI; the desaturation index of total tissue lipids (for oleate/stearate) was 40% higher in muscle lipid extracts from obese donors; and fatty acid oxidation was higher in primary human skeletal myocytes from lean than from obese donors. Studies in animals also show that SCD1 expression is higher in obese than in lean individuals. For example, C57Bl/6 mice fed a high-fat diet have SCD1 mRNA levels 50% higher than those of mice on a low fat diet. SCD1 activity was also shown to be 50% higher in liver microsomes from the high-fat fed mice, by measuring the rate of production of oleate from stearate [S. B. Biddinger et al. *Diabetes* 2005, 54, 1314-1323].

The asebia ($ab^J/ab^J$) mouse is a mutant strain of BALB/c mice. The mutation arose spontaneously and results in a lack of functional SCD1 because of the deletion of the first four exons of the gene. The phenotype of the asebia mouse includes alopecia and skin defects which are not seen in the heterozygotes [A. H. Gates and M. Karasek *Science* 1965, 148, 1471-1473]. In addition, the asebia mice show decreased levels of triglycerides and liver cholesterol esters [M. Miyazaki et al. *J. Biol. Chem.* 2000, 275, 30132-31038]. From studies in animals in which both the SCD1 and ob genes are defective, a greater understanding of the relevance of SCD1 in the development of obesity has emerged.

The ob/ob mouse is one of the most common models used in obesity research. In this model, the mouse has a mutation in the gene that codes for the 16 kDa hormone leptin, which plays a role in the regulation of appetite and energy expenditure, and the mutation renders the mice obese with enlarged livers engorged with fat. Expression of the SCD1 gene is increased in the liver of leptin-deficient ob/ob mice, compared to wild-type mice, and the overexpression of SCD1 is reduced by administration of leptin [P. Cohen et al. *Science* 2002, 297, 240-243]. Furthermore, intercrossing ob/ob mice with asebia mice results in double mutant $ab^J/ab^J$; ob/ob mice which have increased lean mass compared to the ob/ob mice, but lower body weight and lower fat mass, despite consuming more food. These results suggest that downregulation of SCD1 is one mechanism through which leptin acts, and also that SCD1 is indeed a viable target for pharmacological intervention for the treatment of obesity.

The phenotype of an SCD1 knockout mouse further supports the validity of this enzyme as an obesity target. The $SCD1^{-/-}$ mouse was generated by targeted disruption of the SCD1 gene in C57Bl/6 mice. The $SCD1^{-/-}$ mice have reduced body fat and are resistant to weight gain when fed a high-fat diet. They have increased energy expenditure and increased oxygen consumption. Genes involved in lipid oxidation are over-expressed in these mice, while genes involved in lipid synthesis are down-regulated [J. M. Ntambi et al. *Proc. Natl. Acad. Sci USA* 2002, 99, 11482-11486]. Homozygous SCD1 knockout mice exhibit abnormalities in the sebaceous gland as do the asebia mice described above, and also in the meibomian gland in the eye.

SCD1-specific antisense oligonucleotides (ASOs) have been shown to reduce SCD1 mRNA and protein levels in mouse primary hepatocytes. In addition, fatty acid synthesis in primary hepatocytes is reduced while fatty acid oxidation increases. In C57BI/6 mice fed on a high fat diet for 10 weeks, SCD1-specific ASOs led to a significant reduction in weight gain, without an effect on food intake. The percentage of fat is decreased and the ratio of lean mass to total body mass is increased in the ASO-treated animals. Examination of the livers after 10 weeks showed that ASO-treatment resulted in a reduction in de novo fatty acid synthesis and also in hepatic steatosis [G. Jiang et al. *J. Clin. Invest.* 2005, 115, 1030-1038]. The alopecia phenotype of the asebia mouse was not observed in the treated animals. Three patent applications (WO 2005014607, US 2004254359, WO 2003012031) describe antisense compounds, compositions and methods for modulating the expression of stearoyl-CoA desaturase. These compounds, compositions and methods are claimed to be useful for the treatment of diseases associated with the expression of SCD, including atherosclerosis, cardiovascular diseases and abnormal cholesterol or lipid metabolism.

SUMMARY OF THE INVENTION

The present invention pertains to SCD inhibitors In a preferred embodiment, the invention provides compounds of the formula (I):

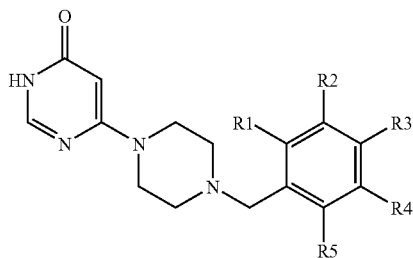

as well as pharmaceutically acceptable salts thereof.

DETAILED DESCRIPTION OF THE INVENTION

In an embodiment of the present invention, provided is a compound of formula (I):

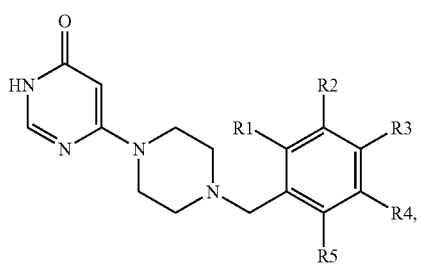

wherein:

$R^1$ is hydrogen, lower alkyl, alkoxy or halogen;

$R^2$ is hydrogen, alkoxy, halogen, haloalkyl, O-haloalkyl or $NO_2$;

$R^3$ is hydrogen, lower alkyl, alkoxy or halogen;

$R^4$ is hydrogen, lower alkyl, halogen, cyano or $NO_2$; and $R^5$ is hydrogen, lower alkyl, hydroxy, haloalkyl or $NO_2$, wherein at least one of $R^1$, $R^2$, $R^3$, $R^4$ or $R^5$ is hydrogen, and pharmaceutically acceptable salts thereof.

In another embodiment of the present invention, provided is a pharmaceutical composition, comprising a therapeutically effective amount of a compound according to formula I or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent carbocyclic radical of three to seven, preferably three to six carbon atoms. This term is further exemplified by radicals such as cyclopropyl, cyclobutyl, cyclopentyl and cyclohexyl. In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic monovalent mono- or polycarbocyclic radical, such as phenyl or naphthyl, preferably phenyl.

The term "heteroaryl," alone or in combination with other groups, means a monocyclic or bicyclic radical of 5 to 12 ring atoms having at least one aromatic ring containing one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, aminocarbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters(e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day Compounds of the present invention can be prepared beginning with commercially available starting materials and utilizing general synthetic techniques and procedures known to those skilled in the art. Outlined below are reaction schemes suitable for preparing such compounds. Further exemplification is found in the specific examples listed below.

Synthesis of Compounds of the Invention According to Scheme 1

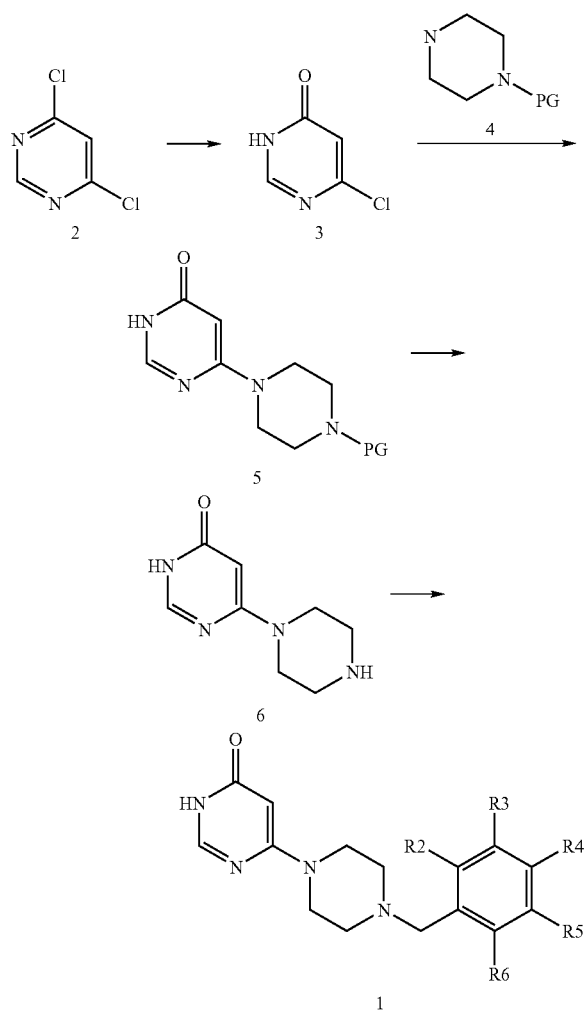

Compounds of the invention may be made by any conventional means. For example, they may be made according to the process outlined in Scheme 1. According to this process, 4,6-dichloropyrimidine of formula 2, which is commercially available (for example, from Aldrich), can be partially hydrolyzed to give 6-chloro-3H-pyrimidin-4-one, the compound of formula 3. This reaction can be conveniently effected by heating a mixture of the compound of formula 2 with aqueous hydrochloric acid at a temperature of about 70° C. The compound of formula 3 is a known compound, and methods that have previously been reported for the preparation of this intermediate could also be used. For example, the partial hydrolysis of the compound of formula 2 to give the desired intermediate of formula 3 has been reported using aqueous hydrochloric acid at a temperature of about 100° C. in D. J. Brown and J. S. Harper *J. Chem. Soc.* 1961, 1298-1303. As a further example, it has been reported that the compound of formula 3 has been made from the compound of formula 2 in a two step process involving first the treatment of the compound of formula 2 with sodium methoxide in the presence of methanol to give 4-chloro-6-methoxy-pyrimidine, followed by hydrolysis of the methoxy group by heating in concentrated hydrochloric acid at 100° C. Conditions suitable for this reaction can be found in D. Isbecque et al. *Helv. Chim. Acta* 1959, 42, 1317-1323. As a final, but not limiting, example that shows how the compound of formula 3 can be made, a procedure has been patented in U.S. Pat. No. 6,562,970 for the preparation of this compound by the hydrolysis of 4-chloro-6-methoxypyrimidine using hydrogen halide. The compound of formula 3 is also commercially available from a number of vendors including Maybridge of Tintagel, Cornwall, UK.

The conversion of the chloropyrimidine of formula 3 to the piperazine-substituted pyrimidine of formula 5 can be conveniently carried out by treating the compound of formula 3 with a mono-protected piperazine derivative of formula 4. A number of protective groups could be used in the compound of formula 4 and many of these are well known to one of average skill in the art of organic synthesis. Conditions that can be used for the introduction and removal of protective groups are enumerated in "Protective Groups in Organic Synthesis" [T. W. Greene and P. G. M. Wuts, 2nd Edition, John Wiley & Sons, N.Y. 1991] in the chapter on protection for the amino group. Some examples of preferred protective groups for the current purpose are the benzyl derivatives (for example, benzyl or 3,4-dimethoxybenzyl) and particularly conveniently the carbamates (especially, tert-butyl carbamate and benzyl carbamate). For example, in the case where the tert-butyl carbamate is selected as the protective group, the compound of formula 3 is treated with the commercially available compound of formula 4 where PG represents tert-butoxycarbonyl in the presence of a base such as an organic base (e.g., triethylamine or diisopropylethylamine or the like) in an inert solvent such as an alcohol (for example, n-butanol or sec-butanol) at a temperature between about 80° C. and about 100° C. to give the substituted compound of formula 5. An example of conditions used to effect a similar displacement reaction of the compound of formula 3 with an amine can be found in J. E. Arrowsmith et al. *J. Med. Chem.* 1989, 32, 562-568.

The conversion of the protected piperazine derivative of formula 5 to the piperazine of formula 6 may be effected by any conventional means. The conditions used to effect this transformation will depend on the nature of the protective group in the compound of formula 5. Suitable conditions for many protective groups may be found in "Protective Groups in Organic Synthesis" [T. W. Greene and P. G. M. Wuts, 2nd Edition, John Wiley & Sons, N.Y. 1991] in the chapter on protection for the amino group. In the case where the protective group in the compound of formula 5 is benzyloxycarbonyl (Cbz), the group can be removed under hydrogenolytic conditions, for example by hydrogenation in the presence of a noble metal catalyst such as palladium-on-carbon, or palladium black, in the presence of an inert solvent (for example, an alcohol such as ethanol) at about room temperature and under atmospheric pressure, or at elevated pressure (such as 50 psi of hydrogen) if required. As a further example, in the case where the protective group is tert-butoxycarbonyl (Boc), the group can be removed by treatment of the compound of formula 5 with acid (either organic or inorganic) in an inert solvent. For example, the Boc group can be removed by treatment of the compound of formula 5 with trifluoroacetic acid in dichloromethane at about room temperature, or it can be removed by treatment of the compound of formula 5 with hydrochloric acid in an alcoholic solvent (e.g., methanol or ethanol) or an ether (e.g., dioxane) or ethyl acetate, also at about room temperature. An alternative and particularly convenient approach for the removal of the Boc group is to use polymer-supported toluenesulfonic acid (MP-TsOH), a reagent commercialized by Argonaut Technologies (which is now part of Biotage AB) and which is available from Aldrich. According to this procedure, the protected derivative of formula 5 is treated with MP-TsOH in an inert solvent such as dichloromethane and the mixture is shaken at room temperature. The compound of formula 6 is then eluted from the resin using ammonia in methanol.

The conversion of the intermediate of formula 6 to the compound of the invention of formula 1 can be effected by conventional methods that are well known to one of average skill in the art of organic synthesis. For example, two of the most commonly used approaches for this type of transformation are alkylation and reductive alkylation. In the alkylation approach, the compound of formula 6 is treated with an alkylating agent [which in this case is a benzyl derivative of formula 7 where X represents a leaving group such as a halide (e.g., chloride, or preferably bromide) or a sulfonate ester (e.g., mesylate, tosylate, or benzenesulfonate)] in the presence of a base such as an organic base (e.g., triethylamine or diisopropylethylamine or the like) or an inorganic base (for example, sodium, potassium or cesium carbonate, or sodium hydrogen carbonate) in an inert solvent such as acetonitrile, 2-butanone, tetrahydrofuran, or N,N-dimethylformamide at a temperature between about room temperature and about 100° C., preferably at about 80° C. Examples of precise conditions suitable for carrying out such an alkylation reaction can be found in the literature, for example in K. J. Hodgetts et al. *Bioorg. Med. Chem.* 2001, 9, 3207-3213; in R. W. Feenstra et al. *Bioorg. Med. Chem. Lett.* 2001, 11, 2345-2349; in J. K. Chakrabarti et al. *J. Med. Chem.* 1989, 32, 2573-2582; and in K. Hino et al. *J. Med. Chem.* 1988, 31, 107-117.

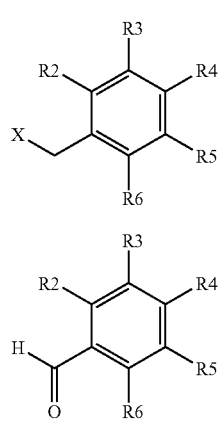

Alternatively, in the reductive alkylation approach, the intermediate of formula 6 is treated with a benzaldehyde of formula 8 and the resulting imine is reduced to give the compound of formula 1. The reduction can be carried out using hydrogenation under noble metal catalysis, or it can be carried out by treating the imine with a reducing agent such as sodium borohydride or sodium cyanoborohydride or preferably sodium triacetoxyborohydride. The imine formation and reduction can be carried out as two separate steps, or they can be combined in a single step. The one-step approach is convenient and is well known to one of average skill in the art of organic synthesis. A review on this reaction with particular focus on the use of sodium triacetoxyborohydride as the reducing agent has recently been published (A. F. Abdel-Magid and S. J. Mehrman *Org. Process Res. Dev.* 2006, 10, 971-1031). The reaction is conveniently carried out by treating the intermediate of formula 6 with a benzaldehyde of formula 8 in an inert solvent such as a halogenated hydrocarbon (for example dichloromethane or 1,2-dichloroethane) in the optional additional presence of an agent that absorbs water such as molecular sieves at about room temperature. A reducing agent such as sodium cyanoborohydride or preferably sodium triacetoxyborohydride is added either at the same time as the intermediate of formula 6 and the benzaldehyde of formula 8 are combined, or after an interval, such as about one hour. Examples of conditions that can be used for this reaction can be found in the literature, for example in W. Sallem et al. *Bioorg. Med. Chem.* 2006, 14, 7999-8013; in WO 2006014133; in E. Bogatcheva et al. *J. Med. Chem.* 2006, 49, 3045-3048; and in D. H. Boschelli et al. *J. Med. Chem.* 2004, 47, 6666-6668.

Synthesis of Compounds of the Invention According to Scheme 2

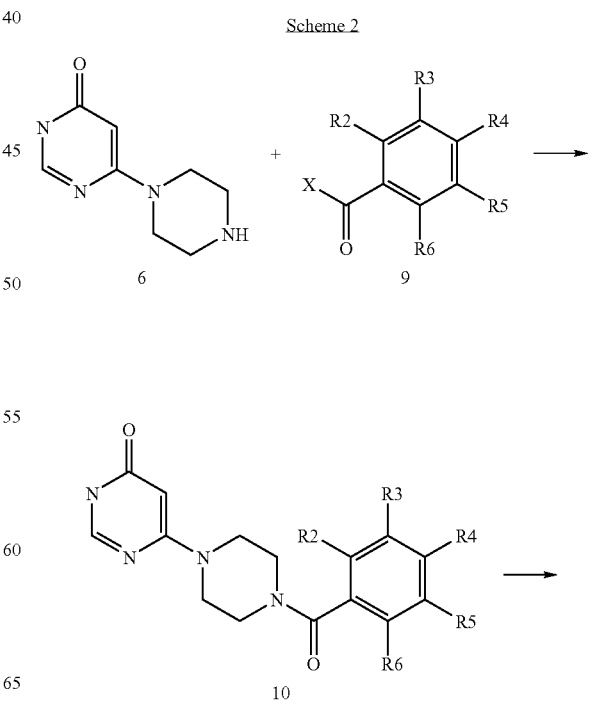

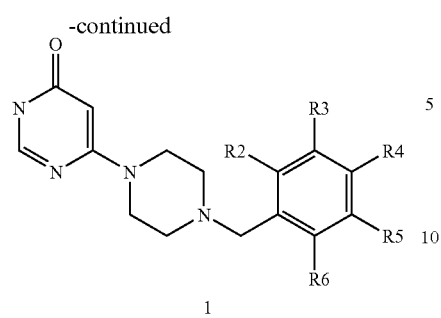

Compounds of the invention may also be made by the process outlined in Scheme 2. According to this process, the intermediate of formula 6 is acylated with benzoic acid or a derivative of benzoic acid of formula 9 to give an amide of formula 10 which can then be reduced to give the compound of the invention of formula 1. It will be immediately obvious to one of average skill in the art that this procedure is appropriate only for the preparation of compounds of formula 1 where any R2, R3, R4, R5, and R6 substituents are stable to the reducing conditions required to effect the conversion of the compound of formula 10 to the compound of formula 1.

The acylation reaction is conveniently carried out by treating the intermediate of formula 6 with the benzoic acid of formula 9 where X represents OH in the presence of an appropriate base, such as diisopropylethylamine, a coupling agent such as O-(benzotriazol-1-yl)-1,1,3,3-tetramethyluronium hexa-fluorophosphate, and in the optional additional presence of a catalyst such as 1-hydroxybenzo-triazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. Alternatively, the reaction can be carried out by converting the carboxylic acid of formula 9 where X represents OH to an activated ester derivative, such as the N-hydroxysuccinimide ester, and subsequently reacting this with the intermediate of formula 6. This reaction sequence can be carried out by reacting the carboxylic acid of formula 9 where X represents OH with N-hydroxysuccinimide in the presence of a coupling agent such as N,N'-dicyclohexylcarbodiimide in an inert solvent such as tetrahydrofuran at a temperature between about 0 degrees and about room temperature. The resulting N-hydroxysuccinimide ester is then treated with the intermediate of formula 6 in the presence of a base, such as an organic base (e.g., triethylamine or diisopropylethylamine or the like) in a suitable inert solvent such as N,N-dimethylformamide at around room temperature. Examples of conditions that can be used for this reaction can be found in the literature, for example in US 2005059668; in A. S. Mehanna and J. Y. Kim *Bioorg. Med. Chem.* 2005, 13, 4323-4331; in N. Serradji et al. *J. Med. Chem.* 2004, 47, 6410-6419; and in M. L. Bolognesi et al. *J. Med. Chem.* 2001, 44, 362-371.

The reduction of the amide derivative of formula 10 to give the compound of the invention of formula 1 can be effected using a reducing agent such as lithium aluminum hydride or borane-methyl sulfide complex. The reaction is carried out by treating a solution of the amide derivative of formula 10 in an inert solvent such as tetrahydrofuran with the reducing agent, preferably lithium aluminum hydride, and then allowing the reaction to proceed at a temperature between about room temperature and about 50° C. Conditions suitable for this reduction reaction can be found in the literature, for example in WO 2007017468; in WO 2005103000; in B. Le Bourdonnec et al. *J. Med. Chem.* 2006, 49, 7290-7306; in M. Qadir et al. *J. Org. Chem.* 2005, 70, 1545-1551; in S. F. Nielsen et al. *J. Med. Chem.* 2005, 48, 2667-2677; and in H. Sugimoto et al. *J. Med. Chem.* 1990, 33, 1880-1887.

Synthesis of Compounds of the Invention According to Scheme 3

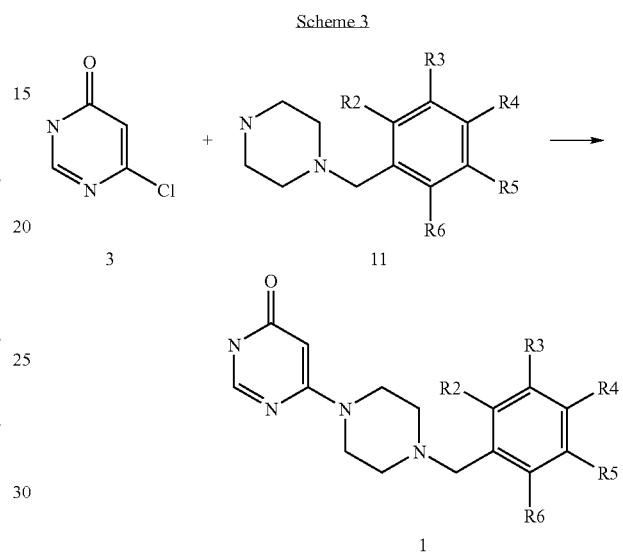

Compounds of the invention of formula 1 can also be prepared by the reaction of the intermediate chloro-pyridone of formula 3 with a piperazine derivative of formula 11. For example, the compound of formula 3 can be treated with the compound of formula 11 in the presence of a base such as an organic base (e.g., triethylamine or diisopropylethylamine or the like) in an inert solvent such as an alcohol (for example, n-butanol or sec-butanol) at a temperature between about 80° C. and about 100° C. to give the compound of the invention of formula 1.

Availability of Reagents Useful for the Preparation of Compounds of the Invention Availability of Compounds of Formula 7

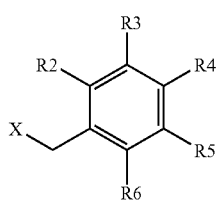

A sample list of commercially available reagents of formula 7 is provided below. This list is provided for the purposes of illustration only and is not intended to limit the reagents of formula 7 that can be used to prepare compounds of the invention. These reagents are available from one or more of the following vendors Acros Organics USA, 500 American Road, Morris Plains, N.J. 07950, USA Aldrich Chemical Company, Inc., 1001 West Saint Paul Avenue, Milwaukee, Wis. 53233, USA.

Alfa Aesar, 26 Parkridge Road, Ward Hill, Mass. 01835, USA

Apollo Scientific Ltd., Whitefield Road, Bredbury, Stockport, Cheshire SK6 2QR, UK.

Matrix Scientific, P.O. Box 25067, Columbia, S.C. 29224-5067, USA

Oakwood Products, Inc., 1741 Old Dunbar Road, West Columbia, S.C. 29172, USA.

TCI America, 9211 N. Harborgate Street, Portland, Oreg. 97203, USA 2,5-Bis(trifluoromethyl)benzyl bromide; 3,5-bis(trifluoromethyl)benzyl bromide; 2-bromobenzyl bromide; 3-bromobenzyl bromide; 4-bromobenzyl bromide; 2-bromo-6-chlorobenzyl bromide; 4-bromo-2,6-difluorobenzyl bromide; 2-bromo-4-fluorobenzyl bromide; 2-bromo-5-fluorobenzyl bromide; 4-bromo-2-fluorobenzyl bromide; 4-(bromomethyl) benzoic acid; 1-(bromomethyl)-2,3-dimethylbenzene; alpha-bromo-m-tolunitrile; 4-bromo-2,3,6-trifluorobenzyl bromide; 2-bromo-5-(trifluoromethyl)benzyl bromide; 4-tert-butylbenzyl bromide; 2-chlorobenzyl bromide; 3-chlorobenzyl bromide; 4-chlorobenzyl bromide; 2-chloro-3,6-difluorobenzyl bromide; 3-chloro-2,6-difluorobenzyl bromide; 4-chloro-2,6-difluorobenzyl bromide; 2-chloro-4-fluorobenzyl bromide; 2-chloro-5-fluorobenzyl bromide; 2-chloro-6-fluorobenzyl bromide; 3-chloro-2-fluorobenzyl bromide; 3-chloro-4-fluorobenzyl bromide; 3-chloro-5-fluorobenzyl bromide; 4-chloro-2-fluorobenzyl bromide; 4-chloro-3-fluorobenzyl bromide; 5-chloro-2-fluorobenzyl bromide; 2-chloro-6- fluoro-3- methylbenzyl bromide; 6-chloro-2-fluoro-3-methylbenzyl bromide; 3-chloro-2-fluoro-5-(trifluoromethyl)benzyl bromide; 3-chloro-2-fluoro-6-(trifluoromethyl)benzyl bromide; 4-chloro-2,3,6-trifluorobenzyl bromide; 2-chloro -3-(trifluoromethyl)benzyl bromide; 2-chloro-5-(trifluoromethyl)benzyl bromide; 4-chloro-3-(trifluoromethyl)benzyl bromide; 5-chloro-2-(trifluoromethyl)benzyl bromide; 3-cyano -4-fluorobenzyl bromide; 3,5-dibromobenzyl bromide; 2,4-dibromo-6-fluorobenzyl bromide; 3,5-dibromo-2-fluorobenzyl bromide; 3,5-di-tert-butylbenzyl bromide; 2,3-dichlorobenzyl bromide; 2,5-dichlorobenzyl bromide; 2,6-dichlorobenzyl bromide; 3,4-dichlorobenzyl bromide; 2,4-dichloro-5-fluorobenzyl bromide; 2,3-difluorobenzyl bromide; 2,4-difluorobenzyl bromide; 2,5-difluorobenzyl bromide; 2,6-difluorobenzyl bromide; 3,4-difluorobenzyl bromide; 3,5-difluorobenzyl bromide; 2,3-difluoro -4-methylbenzyl bromide; 2,6-difluoro-3-methylbenzyl bromide; 2,3-difluoro-4-(trifluoromethyl) benzyl bromide; 2,4-dimethylbenzyl bromide; 3,5-dimethylbenzyl bromide; 2-fluorobenzyl bromide; 3-fluorobenzyl bromide; 4-fluorobenzyl bromide; 2-fluoro -3-methylbenzyl bromide; 2-fluoro-4-methylbenzyl bromide; 3-fluoro-2-methylbenzyl bromide; 3-fluoro-4-methylbenzyl bromide; 3-fluoro-5-methylbenzyl bromide; 4-fluoro-3-methylbenzyl bromide; 5-fluoro-2-methylbenzyl bromide; 2-fluoro-6-nitrobenzyl bromide; 4-fluoro-3-nitrobenzyl bromide; 2-fluoro-3-(trifluoromethyl)benzyl bromide; 2-fluoro-5-(trifluoromethyl)benzyl bromide; 2-fluoro-6-(trifluoromethyl)benzyl bromide; 3-fluoro-2-(trifluoromethyl)benzyl bromide; 3-fluoro-4-(trifluoromethyl)benzyl bromide; 3-fluoro-5-(trifluoromethyl)benzyl bromide; 4-fluoro-2-(trifluoromethyl)benzyl bromide; 4-fluoro-3-(trifluoromethyl)benzyl bromide; 5-fluoro-2-(trifluoromethyl)benzyl bromide; 2-hydroxy-5-nitrobenzyl bromide; 2-iodobenzyl bromide; 3-iodobenzyl bromide; 4-iodobenzyl bromide; 4-iodo-3-nitrobenzyl bromide; 4-isopropyl benzyl bromide; 2-methylbenzyl bromide; 3-methylbenzyl bromide; 4-methylbenzyl bromide; 4-methyl-2,3,5,6-tetrafluorobenzyl bromide; 2-methyl-3-(trifluoromethyl) benzyl bromide; 2-methyl-5-(trifluoromethyl)benzyl bromide; 3-methyl-5-(trifluoromethyl)benzyl bromide; 4-methyl-2-(trifluoromethyl)benzyl bromide; 4-methyl-3-(trifluoromethyl)benzyl bromide; 2-nitrobenzyl bromide; 3-nitrobenzyl bromide; 2-nitro-4-(trifluoromethyl)benzyl bromide; pentafluorobenzyl bromide; 2,3,4,5-tetrafluorobenzyl bromide; 2,3,5,6-tetrafluorobenzyl bromide; alpha,3,5-tribromo-2-hydroxytoluene; 2,3,6-trichlorobenzyl bromide; 2,3,4-trifluorobenzyl bromide; 2,3,5-trifluorobenzyl bromide; 2,3,6-trifluorobenzyl bromide; 2,4,5-trifluorobenzyl bromide; 2,4,6-trifluorobenzyl bromide; 3,4,5-trifluorobenzyl bromide; 2-(trifluoromethyl)benzyl bromide; 3-(trifluoromethyl)benzyl bromide.

In addition to commercially available reagents, compounds of formula 7 may be made using a number of procedures that are widely known in the field of organic synthesis. A listing of many of these methods can be found in "Comprehensive Organic Transformations: A Guide to Functional Group Preparations" [R. C. Larock, VCH Publishers, Inc. New York, 1989], for example on pages 313 and 353-363. Two examples of convenient procedures are described below. As will be clear to one of average skill in the art, not all reactions can be used to prepare all compounds of formula 7, but reactions appropriate for the preparation of specific compounds of formula 7 will be apparent to a synthetic organic chemist.

Compounds of formula 7 where X represents bromine can be prepared by treating a compound of formula 7 where X represents hydrogen with N-bromosuccinimide or 3,3-dimethyl-N,N'-dibromo-hydantoin in an inert solvent such as a halogenated alkane (for example, carbon tetrachloride) or acetonitrile, in the optional additional presence of a catalyst such as azobis(isobutyronitrile) or benzoyl peroxide at a suitable temperature, conveniently at the boiling point of the solvent, and in the optional additional presence of a source of light; or by treating a compound of formula 7 where X represents hydrogen with bromine in an inert solvent such as a mixture of water and an aromatic hydrocarbon (e.g., benzene) or a halogenated alkane (e.g., chloroform) under irradiation with an incandescent light. Compounds of formula 7 where X represents chlorine can be prepared by treating a compound of formula 7 where X represents hydrogen with N-chlorosuccinimide or sulfuryl chloride in an inert solvent such as a halogenated alkane (for example, carbon tetrachloride) or acetonitrile in the optional additional presence of a catalyst such as azobis(isobutyronitrile) or benzoyl peroxide at a suitable temperature, conveniently at the boiling point of the solvent, and in the optional additional presence of a source of light; or by treating a compound of formula 7 where X represents hydrogen with chlorine in an inert solvent such as a mixture of water and an aromatic hydrocarbon (e.g., benzene) or a halogenated alkane (e.g., chloroform or carbon tetrachloride) under irradiation with an incandescent light. Examples of precise conditions suitable for carrying out such a halogenation reaction can be found in the literature, for example in F. L. M. Pattison and B. C. Saunders *J. Chem. Soc.* 1949, 2745-2749; in R. W. Taft et al. *J. Am. Chem. Soc.* 1963, 85, 709-724; in N. Kornblum and D. C. Iffland *J. Am. Chem. Soc.* 1949, 71, 2137-2143; in M. E. Rodriguez et al. *J. Heterocyclic Chem.* 2001, 38, 387-389; and in L. Wang et al. *J. Med. Chem.* 2004, 47, 612-626.

A compound of formula 7 where X represents bromine can be prepared by treating a compound of formula 7 where X represents hydroxyl with phosphorus tribromide or a mixture of N-bromosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 7 where X represents chlorine can be prepared by treating a compound of formula 7 where X represents hydroxyl with thionyl chloride or a mixture of N-chlorosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 7 where X represents $OSO_2E$ where E represents lower alkyl or aryl can be prepared by treating a compound of formula 7 where X represents hydroxyl with a sulfonyl chloride $ESO_2Cl$ (for example, methanesulfonyl chloride or p-toluenesulfonyl chloride) in the presence of a base such as a tertiary amine (e.g., triethylamine or diisopropylethylamine) in an inert solvent such as a halogenated hydrocarbon (e.g., methylene chloride) at a temperature between about 0 degrees and about room temperature, preferably at about 0 degrees. A compound of formula 7 where X represents iodine can be prepared by treating a compound of formula 7 where X represents chlorine, bromine, or $OSO_2E$ where E represents lower alkyl or aryl, with an alkali metal iodide (e.g., sodium iodide) in an inert solvent such as a ketone (e.g., acetone or methyl ethyl ketone) at a temperature between about 50° C. and about 80° C., conveniently at about the boiling point of the solvent. Examples of precise conditions suitable for carrying out such a substitution reaction can be found in the literature, for example in D. Lednicer et al. *J. Med. Chem.* 1980, 23, 424-430; in G. Anilkumar et al. *Org. Process Res. Dev.* 2002, 6, 190-191; in N. Kornblum and D. C. Iffland *J. Am. Chem. Soc.* 1949, 71, 2137-2143; in A. Varnavas et al. *Eur. J. Med. Chem.* 2005, 40, 563-581; in A. B. S. Maya et al. *J. Med. Chem.* 2005, 48, 556-568; and in R. Lines and J. H. P. Utley *J. Chem. Soc., Perkin Trans.* 2 1977, 803-809.

Availability of Compounds of Formula 8

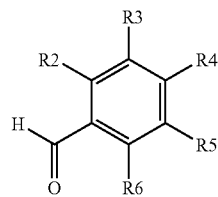

8

A sample list of commercially available aldehydes of formula 8 is provided below. This list is provided for the purposes of illustration only and is not intended to limit the reagents of formula 8 that can be used to prepare compounds of the invention. These reagents are available from one or more of the following vendors Acros Organics USA, 500 American Road, Morris Plains, N.J. 07950, USA Aldrich Chemical Company, Inc., 1001 West Saint Paul Avenue, Milwaukee, Wis. 53233, USA.

Alfa Aesar, 26 Parkridge Road, Ward Hill, Mass. 01835, USA

Apollo Scientific Ltd., Whitefield Road, Bredbury, Stockport, Cheshire SK6 2QR, UK.

Matrix Scientific, P.O. Box 25067, Columbia, S.C. 29224-5067, USA

Oakwood Products, Inc., 1741 Old Dunbar Road, West Columbia, S.C. 29172, USA.

TCI America, 9211 N. Harborgate Street, Portland, Oreg. 97203, USA

2-Bromobenzaldehyde; 3-bromobenzaldehyde; 4-bromobenzaldehyde; 3-bromo -5-tert-butyl-2-hydroxy-benzaldehyde; 5-bromo-2-chlorobenzaldehyde; 3-bromo -5-chloro-2-hydroxybenzaldehyde; 4-bromo-5-chloro-2-hydroxy -benzaldehyde; 3-bromo -4,5-dichloro-2-hydroxybenzaldehyde; 4-bromo-2,6-difluorobenzylaldehyde; 2-bromo-5-fluorobenzaldehyde; 4-bromo-2-fluorobenzaldehyde; 3-bromo-4-fluoro-2-hydroxy-5-nitro-benzaldehyde; 5-bromo-3-fluorosalicylaldehyde; 3-bromo-2-hydroxybenzaldehyde; 3-bromo-2-hydroxy-4,5-dimethyl-benzaldehyde; 3-bromo-2-hydroxy-5-methyl-benzaldehyde; 5-bromo-2-hydroxy-3-methyl-benzaldehyde; 5-bromo-2-hydroxy-4-methyl-benzaldehyde; 3-bromo-2-hydroxy-4-methyl-5-nitro-benzaldehyde; 5-bromo-2-hydroxy -4-methyl-3-nitrobenzaldehyde; 3-bromo-2-hydroxy-5- nitrobenzaldehyde; 5-bromo -2-hydroxy-3-nitro-benzaldehyde; 4-bromo-3-nitro-benzaldehyde; 5-bromosalicylaldehyde; 5-tert-butyl-3-chloro-2-hydroxy-benzaldehyde; 4-tert-butyl-2-hydroxy-benzaldehyde; 5-tert-butyl-2-hydroxy-benzalde-hyde; 5-tert-butyl-2-hydroxy-3-nitro-benzaldehyde; 2-chlorobenzaldehyde; 3-chlorobenzaldehyde; 4-chlorobenzaldehyde; 2-chloro-5-fluorobenzaldehyde; 3-chloro-2-fluorobenzaldehyde; 5-chloro -2-fluorobenzaldehyde; 3-chloro-5-fluoro-2-hydroxybenzaldehyde; 5-chloro-4-fluoro -2-hydroxy-benzaldehyde; 5-chloro-4-fluoro-2-hydroxy-3-nitro -benzaldehyde; 2-chloro -6-fluoro-3-methylbenz-aldehyde; 5-chloro-2-hydroxy-3,4-dimethyl -benzaldehyde; 5-chloro-2-hydroxy-4-methyl-3-nitro-benzaldehyde; 4-chloro-2-hydroxy-5-nitro-benzaldehyde; 2-chloro-6-methylbenzaldehyde; 4-chloro-2,3,6-trifluorobenzaldehyde; 4-chloro-2-(trifluoromethyl)benzaldehyde; 2-cyanobenzaldehyde; 3-cyanobenzaldehyde; 4-cyanobenzaldehyde; 4-cyano-2-fluorobenzaldehyde; 2,5-dibromobenzalde-hyde; 3,5-dibromobenzaldehyde; 3,5-dibromo-2- fluorobenzaldehyde; 3,5-dibromo-2-hydroxy-4-methylbenzaldehyde; 2,5-dichlorobenzaldehyde; 3,4-dichlorobenzaldehyde; 3,5-dichlorosalicyl -aldehyde; 2,4-difluorobenzaldehyde; 3,4-difluorobenzaldehyde; 3,5-difluoro -2-hydroxybenzaldehyde; 3,6-difluoro-2-hydroxybenzaldehyde; 2,6-difluoro-3-methylbenzaldehyde; 3,5-diiodosalicyl-aldehyde; 2,4-dimethylbenzaldehyde; 3,5-dimethylbenzaldehyde; 3,5-dimethyl-4-chloro-2-formyl-phenol; 4-ethylbenzaldehyde; 4-ethyl -3-nitrobenzaldehyde; 2-fluorobenzaldehyde; 3-fluorobenzal-dehyde; 4-fluorobenzaldehyde; 4-fluoro-2-hydroxybenzaldehyde; 2-fluoro-4-iodobenzaldehyde; 2-fluoro -5-iodobenzaldehyde; 2-fluoro-3-methylbenzaldehyde; 3-fluoro-4-methylbenzaldehyde; 3-fluoro-5-methylbenzaldehyde; 4-fluoro-3-methylbenzaldehyde; 5-fluoro-2-methylbenzaldehyde; 2-fluoro-5-nitrobenzaldehyde; 4-fluoro -3-nitrobenzaldehyde; 2-fluoro-3-(trifluoromethyl)benzaldehyde; 2-fluoro-4-(trifluoromethyl)benzaldehyde; 2-fluoro-5-(trifluoromethyl)benzaldehyde; 3-fluoro-2-(trifluoromethyl) benzaldehyde; 2-hydroxy-4,5-dimethyl-benzaldehyde; 2-hydroxy-4,6-dimethyl-benzaldehyde; 2-hydroxy-3,4-dimethyl-5-nitro-benzaldehyde; 2-hydroxy-3,6-dimethyl -5-nitro-benzaldehyde; 2-hydroxy-5-iodo-3-methyl-benzaldehyde; 2-hydroxy-5-iodo -4-methyl-benzal-dehyde; 2-hydroxy-5-iodo-3-nitro-benzaldehyde; 2-hydroxy-5-isopropyl-benzaldehyde; 2-hydroxy-5-methylbenzaldehyde; 2-hydroxy-4-methyl-5-nitro -benzaldehyde; 3-iodobenzaldehyde; 4-isobutylbenzaldehyde; 3-isopropylbenzaldehyde;

4-isopropylbenzaldehyde; m-tolualdehyde; pentamethylbenzaldehyde; 2,3,4,5-tetrafluorobenzaldehyde; 2,3,5,6-tetramethylbenzaldehyde; p-tolualdehyde; 2,3,6-trichlorobenzaldehyde; 2,3,5-trifluorobenzaldehyde; 2,4,5-trifluorobenzaldehyde; 2,4,6-trifluorobenzaldehyde; 3-(trifluoromethyl) benzaldehyde; and 2,4,5-trimethylbenzalde-hyde.

In addition to commercially available reagents, compounds of formula 8 may be made using a number of procedures that are widely known in the field of organic synthesis. A listing of many of these methods can be found in "Comprehensive Organic Transformations: A Guide to Functional Group Preparations" [R. C. Larock, VCH Publishers, Inc. New York, 1989], for example on pages 604-624. Some of the most common reactions used to prepare aldehydes of formula 8 include the oxidation of benzylic alcohols (for example using manganese dioxide, using Swern conditions, using the Dess-Martin periodinane, or using o-iodoxybenzoic acid); the reduction of carboxylic acid derivatives (for example, esters or nitriles) using diisobutylaluminum hydride, sodium bis(2-methoxyethoxy)-aluminum hydride (Red-Al) or the like; palladium-catalyzed carbonylation; lithium-halogen exchange followed by reaction of the anion with a formamide such as N-formyl piperidine or N,N-dimethylformamide; or by oxidative cleavage of the double bond of a vinyl-benzene derivative.

Examples of precise conditions suitable for carrying out the oxidation of a benzylic alcohol to a benzaldehyde can be found in the literature, for example in J. S. Yadav et al. *Tetrahedron* 2004, 60, 2131-2135; in C. Kuhakam et al. *Synth. Commun.* 2006, 36, 2887-2892; in C. Theeraladanon et al. *Tetrahedron* 2004, 60, 3017-3035; in H. Zhao and A. Thurkauf *Synth. Commun.* 2001, 31, 1921-1926; in A. W. White et al. *J. Med. Chem.* 2000, 43, 4084-4097; in J. Clayden et al. *Tetrahedron* 2004, 60, 4399-4412; in N. Maezaki et al. *Tetrahedron* 2000, 56, 7927-7945; in A. P Combs et al. *J. Med. Chem.* 2006, 49, 3774-3789; and in R. M. Moriarty et al. *J. Org. Chem.* 2004, 68, 1890-1902.

Examples of precise conditions suitable for carrying out the reduction of a carboxylate ester to a benzaldehyde can be found in the literature, for example in N. Nakane et al. *J. Org. Chem.* 2004, 69, 3538-3545; T. Abe et al. *Tetrahedron* 2001, 57, 2701-2710; and in R. Kanazawa and T. Tokoroyama *Synthesis* 1976, 526-527. Examples of precise conditions suitable for carrying out the reduction of a nitrile to a benzaldehyde can be found in the literature, for example in D. Castellnou et al. *Tetrahedron* 2005, 61, 12111-12120; in T. Itoh et al. *J. Am. Chem. Soc.* 2006, 128, 957-967; E. David et al. *J. Org. Chem.* 2005, 70, 3569-3573; and in B. D. Roth et al. *J. Med. Chem.* 1990, 33, 21-31.

Examples of precise conditions suitable for carrying out the conversion of a bromo-benzene or iodo-benzene derivative to a benzaldehyde by metal-halogen exchange followed by formylation can be found in the literature, for example in T. Kliś and J. Serwatowski *Tetrahedron Lett.* 2007, 48, 1169-1173; C. G. Oliveri et al. *J. Am. Chem. Soc.* 2006, 128, 16286-16296; in S. Fergus et al. *J. Org. Chem.* 2004, 69, 4663-4669; and in S. Hibino et al. *Heterocycles* 1989, 28, 275-282.

Examples of precise conditions suitable for carrying out the palladium-catalyzed carbonylation of a halobenzene derivative or the like can be found in the literature, for example in K. Orito et al. *J. Org. Chem.* 1999, 64, 6583-6596; in R. W. Bates et al. *Tetrahedron* 1995, 51, 8199-9212; and in H. Iwamoto et al. *Tetrahedron Lett.* 2002, 43, 8191-8194.

Examples of precise conditions suitable for carrying out the oxidative cleavage of the double bond of a vinyl-benzene derivative can be found in the literature, for example in A. Srikrishna and G. Satyanarayana *Tetrahedron* 2006, 62, 2893-2900; H. Maeda et al. *J. Org. Chem.* 2005, 70, 9693-9701; in A. Hashimoto et al. *Bioorg. Med. Chem.* 2005, 13, 3627-3639; in S. Lai and D. G. Lee *Synthesis* 2001, 1645-1648; in Y.-Z. Hu and D. L. J. Clive *J. Chem. Soc. Perkin Trans. I* 1997, 1421-1424; in S. Rao Kasibhatla et al. *J. Med. Chem.* 2000, 43, 1508-1518; and in D. Yang and C. Zhang *J. Org. Chem.* 2001, 66, 4814-4818.

Availability of Compounds of Formula 9

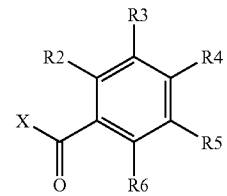

A sample list of commercially available benzoic acids of formula 9 is provided below. This list is provided for the purposes of illustration only and is not intended to limit the reagents of formula 9 that can be used to prepare compounds of the invention. These reagents are available from one or more of the following vendors Acros Organics USA, 500 American Road, Morris Plains, N.J. 07950, USA Aldrich Chemical Company, Inc., 1001 West Saint Paul Avenue, Milwaukee, Wis. 53233, USA.

Alfa Aesar, 26 Parkridge Road, Ward Hill, Mass. 01835, USA

Apollo Scientific Ltd., Whitefield Road, Bredbury, Stockport, Cheshire SK6 2QR, UK.

Matrix Scientific, P.O. Box 25067, Columbia, S.C. 29224-5067, USA

Oakwood Products, Inc., 1741 Old Dunbar Road, West Columbia, S.C. 29172, USA.

TCI America, 9211 N. Harborgate Street, Portland, Oreg. 97203, USA 2,5-Bis(trifluoromethyl)benzoic acid; 3,4-bis-trifluoromethyl-benzoic acid; 2-bromobenzoic acid; 3-bromobenzoic acid; 5-bromo-2-chlorobenzoic acid; 5-bromo-4-chloro-2-fluorobenzoic acid; 4-bromo-2,6-difluorobenzoic acid; 2-bromo-3-fluorobenzoic acid; 2-bromo-5-fluorobenzoic acid; 3-bromo-2-fluorobenzoic acid; 3-bromo-5-fluorobenzoic acid; 4-bromo-2-fluorobenzoic acid; 5-bromo-2-fluorobenzoic acid; 2-bromo -5-iodobenzoic acid; 5-bromo-2-iodobenzoic acid; 2-bromo-4-methylbenzoic acid; 3-bromo-2-methylbenzoic acid; 2-bromo-3-nitrobenzoic acid; 2-bromo -5-nitrobenzoic acid; 4-bromo-2,3,5,6-tetrafluorobenzoic acid; 2-bromo-3-(trifluoromethyl)benzoic acid; 3-bromo-5-(trifluoromethyl)benzoic acid; 3-chlorobenzoic acid; 2-chloro -4,5-difluorobenzoic acid; 5-chloro-2,3-difluoro-4-methylbenzoic acid; 6-chloro-2,3-difluoro-4-(trifluoromethyl)benzoic acid; 2-chloro-3,5-dinitrobenzoic acid; 2-chloro-3-fluorobenzoic acid; 2-chloro-4-fluorobenzoic acid; 2-chloro-6-fluoro-3-methylbenzoic acid; 4-chloro-3-iodobenzoic acid; 3-chloro-2-methyl-benzoic acid; 4-chloro-3-methylbenzoic acid; 4-chloro -2-nitrobenzoic acid; 5-chloro-2-nitrobenzoic acid; 3-chlorosalicylic acid; 4-chloro -2-(trifluoromethyl)benzoic acid; 5-chloro-2-(trifluoromethyl)-benzoic acid; 4-cyanobenzoic acid; 2-cyano-5-fluorobenzoic acid; 4-cyclopropyl-benzoic acid; 3,5-dibromobenzoic acid; 2,4-dibromo-6-fluorobenzoic acid; 2,3-dichlorobenzoic acid; 2,4-dichlorobenzoic acid; 2,4-dichloro-5-fluorobenzoic acid;

2,5-dichloro-3-nitrobenzoic acid; 3,5-dichlorosalicylic acid; 2,6-difluorobenzoic acid; 3,4-difluorobenzoic acid; 3,5-difluorobenzoic acid; 2,6-difluoro-3-nitrobenzoic acid; 2,6-dihydroxy-4-methylbenzoic acid; 3,4-dimethylbenzoic acid; 2,6-dimethyl-4-fluorobenzoic acid; 3,5-dinitrosalicylic acid; 4-fluorobenzoic acid; 2-fluoro-6-hydroxybenzoic acid; 2-fluoro-4-iodobenzoic acid; 2-fluoro-5-iodobenzoic acid; 2-fluoro-6-iodobenzoic acid; 4-fluoro -2-iodobenzoic acid; 2-fluoro-4-methylbenzoic acid; 4-fluoro-2-methylbenzoic acid; 2-fluoro-6-nitrobenzoic acid; 3-fluoro-4-nitrobenzoic acid; 4-fluoro-3-nitrobenzoic acid; 5-fluoro-2-nitrobenzoic acid; 2-fluoro-3-(trifluoromethyl)benzoic acid; 4-fluoro-3-(trifluoromethyl)benzoic acid; 5-fluoro-2-(trifluoromethyl)benzoic acid; 2-hydroxy-3-isopropyl-benzoic acid; 3-iodobenzoic acid; 5-iodosalicylic acid; 2-iodo-3-(trifluoromethyl)benzoic acid; 4-methyl-2-chlorobenzoic acid; 2-methyl-3-nitrobenzoic acid; 2-methyl-4-nitro-benzoic acid; 3-methyl-2-nitrobenzoic acid; 4-methyl-2-nitrobenzoic acid; 4-methyl-3-nitrobenzoic acid; 3-methylsalicylic acid; 5-methylsalicylic acid; 3-methyl-5-(trifluoromethyl)benzoic acid; 4-methyl-3-(trifluoromethyl)benzoic acid; 2-nitrobenzoic acid; 3-nitrobenzoic acid; 5-nitrosalicylic acid; 4-n-propylbenzoic acid; o-toluic acid; pentafluorobenzoic acid; 4-tert -butylbenzoic acid; 2,3,4,6-tetrafluorobenzoic acid; 2,3,4,5-tetrafluoro-6-chlorobenzoic acid; 3,4,5,6-tetrafluoro-2-hydroxy-benzoic acid; 2,3,5,6-tetrafluoro-4-methylbenzoic acid; 2,3,5,6-tetramethylbenzoic acid; 2,4,6-trichlorobenzoic acid; 2,3,4-trifluorobenzoic acid; 2,4,5-trifluorobenzoic acid; 2,4,6-trifluoro-3,5-dimethylbenzoic acid; 2-(trifluoromethyl)benzoic acid; 3-(trifluoromethyl)benzoic acid; 4-(trifluoromethyl)benzoic acid; 2,4,5-trifluoro-3-nitrobenzoic acid; 2,4,6-trifluoro-3-(trifluoro -methyl)benzoic acid; 2,4,5-trimethylbenzoic acid; and 2,4,6-trimethylbenzoic acid.

In addition to commercially available reagents, compounds of formula 9 may be made using a number of procedures that are widely known in the field of organic synthesis. A listing of many of these methods can be found in "Comprehensive Organic Transformations: A Guide to Functional Group Preparations" [R. C. Larock, VCH Publishers, Inc. New York, 1989], for example on pages 828, 834-841, 851, and 993. Some of the most common reactions used to prepare aldehydes of formula 9 include the oxidation of benzylic alcohols, for example using potassium permanganate in acetone; palladium-catalyzed carboxylation of an aryl bromide, iodide or triflate; lithium-halogen exchange followed by reaction with carbon dioxide or a chloroformate followed by hydrolysis; hydrolysis of a nitrile; by the iodoform reaction; or by oxidative cleavage of the double bond of a vinyl-benzene derivative.

A benzyl alcohol may be conveniently converted to a benzoic acid of formula 9 by treating the alcohol with an oxidizing agent such as potassium permanganate in a solvent such as acetone at a temperature between about 0° C. and about room temperature. The reaction may alternatively be carried out using water as solvent in the presence of a phase-transfer catalyst such as benzyl triethylammonium chloride. Examples of precise conditions suitable for carrying out the oxidation of a benzyl alcohol to give a benzoic acid can be found in the literature, for example in R. W. Friesen et al. *J. Med. Chem.* 2003, 46, 2413-2426; in G. H. Posner et al. *J. Med. Chem.* 2002, 45, 3824-3828; in J. Balint et al. *Tetrahedron Asymm.* 2001, 12, 3417-3422; in M. Zhao et al. *J. Org. Chem.* 1999, 64, 2564-2566; and in G. Solladié et al. *J. Org. Chem.* 1998, 63, 3895-3898.

A vinyl-benzene derivative may be conveniently converted to a benzoic acid of formula 9 by treating it with an oxidizing agent such as potassium permanganate in a solvent such as acetone at a temperature about room temperature. Examples of precise conditions suitable for carrying out the oxidative cleavage of the double bond of a vinyl-benzene derivative can be found in the literature, for example in G. H. Posner et al. *J. Med. Chem.* 2002, 45, 3824-3828; in Z. Li et al. *J. Med. Chem.* 2005, 48, 6169-6173; in B. R. Travis et al. *J. Am. Chem. Soc.* 2002, 124, 3824-3825; in P. W. Jeffs and T. P. Toube *J. Org. Chem.* 1966, 48,189-192; and in S. Sheffer-Dee-Noor and D. Ben-Ishai *Tetrahedron* 1994, 50, 7009-7018.

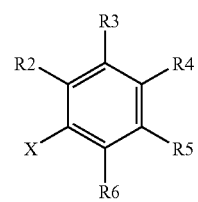

12

The preparation of an intermediate of formula 9 from a compound of formula 12 where X represents bromine or iodine can be carried out conveniently by treating the compound of formula 12 where X represents bromine or iodine with an organolithium reagent such as n-butyllithium or tert-butyllithium in a solvent such as tetrahydrofuran at a low temperature such as about −78° C. in order to effect metal-halogen exchange. It will be readily apparent to one of average skill in the art of organic synthesis that this procedure is limited in applicability to those cases where the R2, R3, R4, R5, and R6 are stable to the metal-halogen exchange reaction. The resulting organolithium intermediate of formula 15 where X represents lithium is then treated with carbon dioxide either in solid form as dry ice or in gaseous form, conveniently by bubbling carbon dioxide gas through a solution of the organolithium intermediate in tetrahydrofuran at low temperature. Examples of precise conditions suitable for carrying out this reaction can be found in the literature, for example in M. Schlosser et al. *Eur. J. Org. Chem.* 2006, 4398-4404; J. A. O'Meara et al. *J. Med. Chem.* 2005, 48, 5580-5588; M. Vivier et al. *J. Med. Chem.* 2005, 48, 6731-6740; in D. Mabire et al. *J. Med. Chem.* 2005, 48, 2134-2153; and in E. Castagnetti and M. Schlosser *Eur. J. Org. Chem.* 2001, 691-695.

Alternatively, the preparation of an intermediate of formula 9 from a compound of formula 12 where X represents bromine, iodine, or triflate can be carried out conveniently by treating the compound of formula 15 where X represents bromine, iodine, or triflate with water in the presence of a palladium catalyst such as bis(triphenylphosphine)palladium (II) dichloride, in the presence of an additional ligand such as triphenylphosphine or tri-o-tolylphosphine, and in the presence of an organic base such as triethylamine or diisopropylethylamine, under an atmosphere of carbon monoxide at a pressure of between about 1 atmosphere and about 10 atmospheres. The reaction may be carried out in the presence of an additional solvent such as dimethylformamide, dimethylsulfoxide, or tetrahydrofuran, and is conveniently carried out at a temperature of about 70° C. to about 100° C. Examples of precise conditions suitable for carrying out this reaction can be found in the literature, for example in D. A. Rama et al. *Tetrahedron* 1994, 50, 2543-2550; in F. Zouhiri et al. *Tetrahedron Lett.* 2005, 46, 2201-2205; in Y. Uozumi and T. Watanabe *J. Org. Chem.* 1999, 64, 6921-6923; in F. Karimi and B. Långström *J. Chem. Soc., Perkin Trans. 1* 2002, 2256-2259; and in G.-D. Zhu et al. *J. Med. Chem.* 2001, 44, 3469-3487.

A carboxylic acid of formula 9 can be prepared from a benzonitrile of formula 12 where X represents cyano. The reaction can be carried out by heating the nitrile in concentrated hydrochloric acid or in aqueous sulfuric acid at reflux, or by heating the nitrile in aqueous sodium hydroxide or potassium hydroxide in the optional additional presence of a co-solvent such as methanol at reflux. Examples of precise conditions suitable for carrying out this reaction can be found in the literature, for example in J. F. Callahan et al. *J. Med. Chem.* 2002, 45, 999-1001; in K. S. Gudmundsson et al. *Bioorg. Med. Chem.* 2005, 13, 5346-5361; in X. Bu et al. *Bioorg. Med. Chem.* 2005, 13, 3657-3665; in S. D. Barchéchath et al. *J. Med. Chem.* 2005, 48, 6409-6422; and in M. C. Van Zandt et al. *Bioorg. Med. Chem.* 2004, 12, 5661-5675.

A carboxylic acid of formula 9 can be prepared from an acetophenone of formula 12 where X represents C(=O)CH3 using a reaction called the haloform reaction (specifically the iodoform reaction or the bromoform reaction, depending on the reagent used). The reaction can be carried out by treating the acetophenone with iodine and potassium iodide or bromine in aqueous solution in the presence of a base such as aqueous sodium hydroxide in the optional additional presence of a co-solvent such as dioxane at a temperature between about 0° C. and about room temperature. Examples of precise conditions suitable for carrying out this reaction can be found in the literature, for example in F. P. Silverman et al. *J. Agric. Food Chem.* 2005, 53, 9775-9780; in J. P. Stormand C.-M. Andersson *J. Org. Chem.* 2000, 65, 5264-5274; in J. R. Hwu et al. *J. Med. Chem.* 1997, 40, 3434-3441; in B. Dumaîitre and N. Dodic *J. Med. Chem.* 1996, 39, 1635-1644; and in D. Gardette and J. Lhomme *J. Org. Chem.* 1979, 44, 2315-2318.

Availability of Compounds of Formula 11

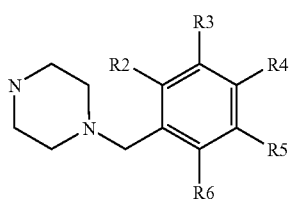

A sample list of commercially available reagents of formula 11 is provided below. This list is provided for the purposes of illustration only and is not intended to limit the reagents of formula 11 that can be used to prepare compounds of the invention. These reagents are available from one or more of the following vendors Acros Organics USA, 500 American Road, Morris Plains, N.J. 07950, USA Aldrich Chemical Company, Inc., 1001 West Saint Paul Avenue, Milwaukee, Wis. 53233, USA.

Alfa Aesar, 26 Parkridge Road, Ward Hill, Mass. 01835, USA

Apollo Scientific Ltd., Whitefield Road, Bredbury, Stockport, Cheshire SK6 2QR, UK.

Matrix Scientific, P.O. Box 25067, Columbia, S.C. 29224-5067, USA

Oakwood Products, Inc., 1741 Old Dunbar Road, West Columbia, S.C. 29172, USA.

TCI America, 9211 N. Harborgate Street, Portland, Oreg. 97203, USA 1-(2-Bromobenzyl)piperazine; 1-(3-bromobenzyl)piperazine; 1-(4-bromobenzyl)piperazine; 1-(4-bromo-2-fluorobenzyl)piperazine; 1-(4-tert -butylbenzyl)piperazine; 1-(2-chlorobenzyl)piperazine; 1-(3-chlorobenzyl)piperazine; 1-(4-chlorobenzyl)piperazine; 1-(2-chloro-benzyl)-piperazine hydrochloride; 1-(4-chloro-benzyl)-piperazine hydrochloride; 1-(2-chloro-4-fluoro-benzyl)-piperazine; 1-(2-chloro-6-fluorobenzyl)piperazine; 1-(3-cyanobenzyl) piperazine; 1-(2,4-dichlorobenzyl)piperaz-ine; 1-(2,6-dichlorobenzyl)piperazine; 1-(3,4-dichlorobenzyl) piperazine; 1-(2,3-difluoro-benzyl)-piperazine; 1-(2,4-difluorobenzyl)piperazine; 1-(2,5-difluorobenzyl) piperazine; 1-(2,6-difluorobenz-yl)piperazine; 1-(3,4-difluorobenzyl)piperazine; 1-(3,5-difluorobenzyl) piperazine; 1-(2,5-dimethyl-benzyl)-piperazine; 1-(3,4-dimethylbenzyl)piperazine; 1-(4-ethyl-benzyl)-piperazine; 1-(4-ethyl-benzyl)-piperazine hydrochloride; 1-(2-fluorobenzyl)piperazine; 1-(3-fluorobenzyl)piperazine; 1-(4-fluorobenzyl)piperazine; 1-(3-fluoro-benzyl)-piperazine hydrochloride; 1-(2-fluoro-benzyl)-piper -azine hydrochloride; 1-(2-iodobenzyl)piperazine; 1-(3-iodobenzyl)piperazine; 1-(4-iodobenzyl)-piperazine; 1-(2-methylbenzyl)piperazine; 1-(3-methylbenzyl)piperazine; 1-(4-methylbenzyl) piper-azine; 1-(3-methyl-benzyl)-piperazine dihydrochloride; 1-(2-methyl-benzyl)-piperazine hydrochloride; 1-(4-methyl-benzyl)-piperazine hydrochloride; 1-(2-nitrobenzyl)piperazine dihydrochloride; 1-(3-nitrobenzyl)piperazine dihydrochloride; 1-[3-(trifluoromethyl)benzyl] piperazine; 1-(2,4,6-trimethylbenzyl)piperazine.

Scheme 4

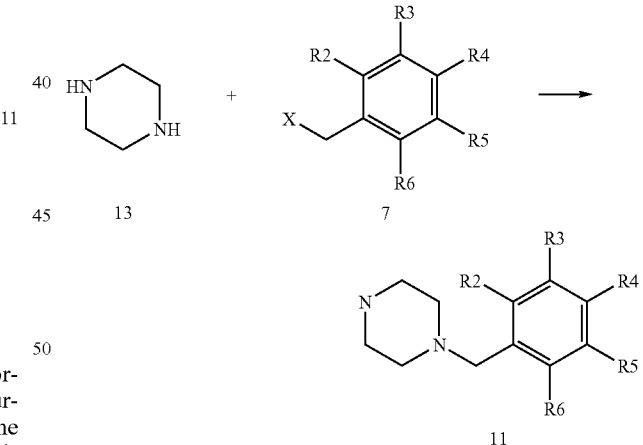

In addition to commercially available reagents, compounds of formula 11 may be made using the procedure outlined in Scheme 4. According to this process, the monohydrochloride salt of piperazine (piperazine free base has formula 13) is reacted with a compound of formula 7 where X represents a leaving group such as a halide (e.g., chloride, or preferably bromide) or a sulfonate ester (e.g., mesylate, tosylate, or benzenesulfonate)] in an inert solvent such as ethanol at room temperature for approximately one hour and then at about 70° C. for about 30 min. Examples of precise conditions suitable for carrying out such an alkylation reaction can be found in the literature, for example in GB 840,358. Alternatively, the compound of formula 7 where X represents a leaving group such as a halide (e.g., chloride, or preferably bromide) or a sulfonate ester (e.g., mesylate, tosylate, or benzenesulfonate) may be heated in excess piperazine in the absence of any additional solvent at a temperature of about 120° C. Examples of precise conditions suitable for carrying out such an alkylation reaction can be found in the literature, for example in U.S. Pat. No. 2,451,645.

The invention will now be further described in the Examples below, which are intended as an illustration only and do not limit the scope of the invention.

EXAMPLES

The following abbreviations are used for synthetic reagents:

| Abbreviation | Reagent | Available from |
|---|---|---|
| MP-TsOH | Macroporous polystyrene sulfonic acid resin | Aldrich |
| PL-NCO | StratoSpheres ™ PL-NCO (Isocyanate) resin | Aldrich |

LCMS Method

The purity of the intermediates was assessed by LC/MS using the following conditions. Column: Atlantis dC18, 2.1× 50 mm, 5 um; Mobile Phase A=water containing 0.1% formic acid, Mobile Phase B=acetonitrile containing 0.1% formic acid; Gradient: 5% B to 100% B over 2.5 min; Flow rate=1 mL/min; Injection volume=3 µL; Detection at 215 nm.

The purity and identity of the examples were assessed by LC/MS using a Micromass Platform II spectrometer: ES Ionization in positive mode (mass range: 150-1200 amu). Mobile Phase=Water containing 0.02% TFA, Mobile Phase B=Acetonitrile containing 0.02% TFA; Gradient 10% B to 90% B over 3 minutes; equilibration time of 1 minute; Flow rate=2 mL/minute Intermediate 1: 6-Chloro-3H-pyrimidin-4-one

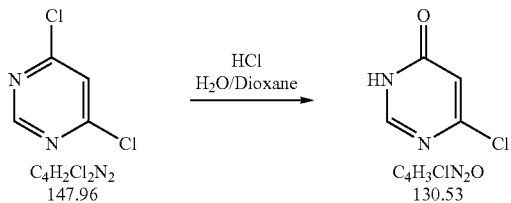

A mixture of 4,6-dichloropyrimidine (Aldrich; 10.00 g, 67.1 mmol), concentrated hydrochloric acid (50 mL), water (50 mL) and dioxane (50 mL) was heated at about 70° C. for 6 h, and then allowed to cool to room temperature. This gave a pink solution. The solvents were evaporated under reduced pressure (vacuum pump) to give a pink solid. Ethanol (50 mL) was added and the mixture was heated. The solid went into solution. The solution was placed in a warm bath (about 50° C.) and allowed to cool slowly. After standing over the weekend, the off-white solid was filtered off to give 6-chloro-3H -pyrimidin-4-one (5.02 g, 57%), mp 193-194° C. (lit. mp 192-193° C. in D. J. Brown and J. S. Harper *J. Chem. Soc.* 1961, 1298-1303). $^1$H NMR (d$_6$-DMSO) δ 6.50 (s, 1H), 8.19 (s, 1H), 13.00 (br s, 1H).

Intermediate 2: 4-(6-Oxo-1,6-dihydro-pyrimidin-4-yl)-piperazine-1-carboxylic acid tert-butyl ester

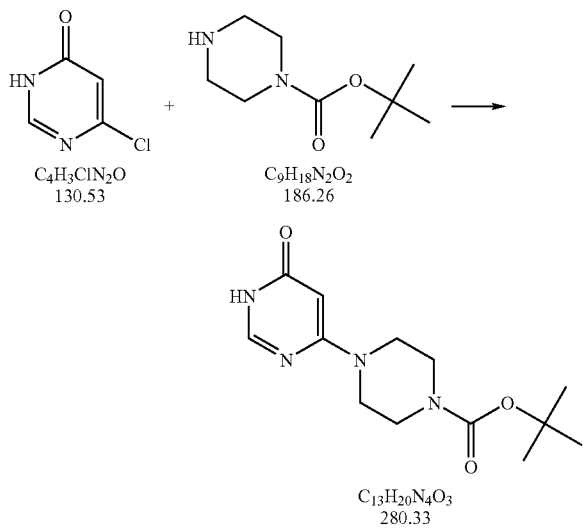

To a suspension of 6-chloro-3H-pyrimidin-4-one (~0.23 mol) in sec-butanol (525 mL) was added ethyldiisopropylamine (49.7 mL, 0.3 mol) and BOC-piperazine (available from Aldrich; 55.9 g, 0.3 mol). The reaction was stirred at 80° C. for 8 hours, and then allowed to cool to room temperature. The crude reaction mixture was filtered, and washed with sec-butanol to give 4-(6-oxo-1,6-dihydro-pyrimidin-4-yl) -piperazine-1-carboxylic acid tert-butyl ester (47.8 g, 74%) LCMS Purity=100% (Rt=1.42). $^1$H NMR (400 MHz, CDCl$_3$) δ 7.80 (s, 1H), 5.34 (s, 1H), 3.56-3.46 (m, 4H), 3.46-3.38 (m, 4H), 1.38 (s, 9H).

Intermediate 3: 4-(6-Oxo-1,6-dihydro-pyrimidin-4-yl)-piperazine-1-carboxylic acid benzyl ester

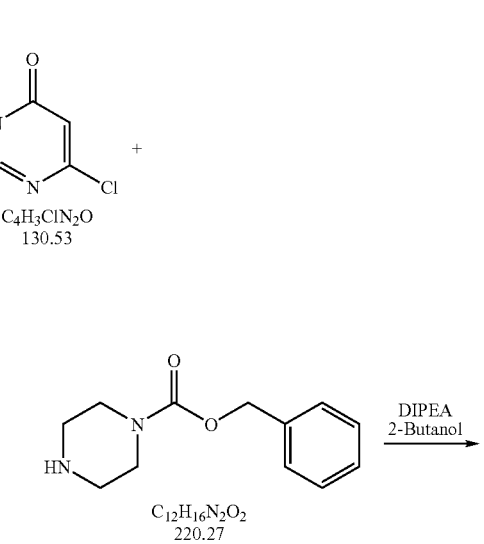

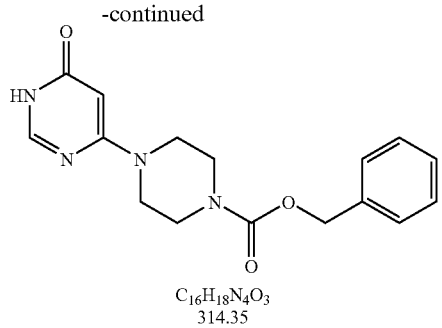

$C_{16}H_{18}N_4O_3$
314.35

A mixture of 6-chloro-3H-pyrimidin-4-one (36984-063-A; 3.90 g, 29.9 mmol), benzyl 1-piperaz-inecarboxylate (Aldrich; 8.81 g, 40.0 mmol), and diisopropylethylamine (7.0 mL, 40.2 mmol) in 2-butanol (100 mL) was heated in a 250 mL round-bottomed flask equipped with a reflux condenser in an oil-bath at about 80° C. (oil-bath temperature) for 8 hours. The heating bath was removed and the reaction mixture was left standing at room temperature overnight. The white solid was filtered off, washed with 2-butanol, and air-dried to give 4-(6-oxo-1,6-dihydro-pyrimidin-4-yl)-piperazine-1-carboxylic acid benzyl ester (7.76 g, 83%) as a white powder, mp 247-249° C. $^1$H NMR (d$_6$-DMSO) δ 1.39 (s, 9H), 3.45-3.50 (m, 8H), 5.08 (s, 2H), 5.26 (s, 1H), 7.28-7.38 (m, 5H), 7.90 (s, 1H), 11.66 (br s, 1H).

Intermediate 4: 6-Piperazin-1-yl-3H-pyrimidin-4-one

Method 1

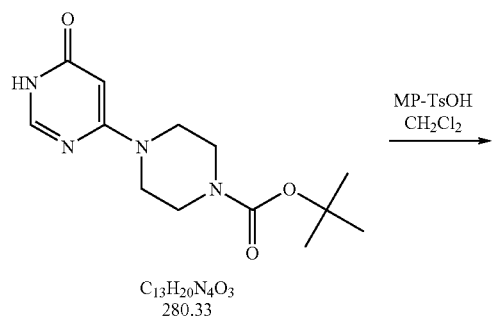

$C_{13}H_{20}N_4O_3$
280.33

MP-TsOH
CH$_2$Cl$_2$ $C_8H_{12}N_4O$
180.21

To a solution of 4-(6-oxo-1,6-dihydro-pyrimidin-4-yl)-piperazine-1-carboxylic acid tert-butyl ester (13.5 g, 48.2 mmol) in dichloromethane (200 mL) was added MP-TsOH (available from Aldrich; 81.0 g). The reaction was shaken at room temperature for 4 days. The crude reaction mixture was filtered and the resin was washed with methanol (460 mL). The desired product was eluted from the resin with 2M ammonia in methanol (460 mL) to give 6-piperazin-1-yl-3H-pyrimidin-4-one (8.4 g, 90%). LCMS Purity=96% (Rt=0.22 in the solvent front). $^1$H NMR (d$_6$-DMSO) δ 7.75 (s, 1H), 5.10 (s, 1H), 2.60-2.42 (m, 4H), 2.38-2.25 (m, 4H).

Method 2

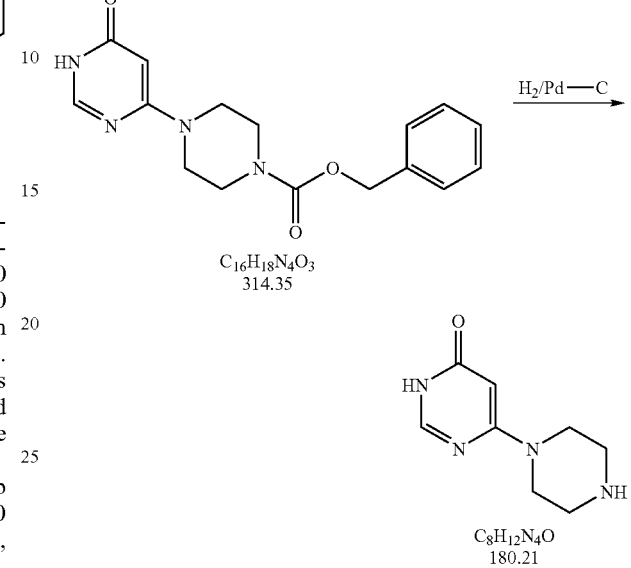

$C_{16}H_{18}N_4O_3$
314.35

H$_2$/Pd—C $C_8H_{12}N_4O$
180.21

A mixture of 4-(6-oxo-1,6-dihydro-pyrimidin-4-yl)-piperazine-1-carboxylic acid benzyl ester (Intermediate 3; 2.00 g, 7.14 mmol) and a catalytic amount of 10% palladium on carbon in ethanol (300 mL) was hydrogenated at atmospheric temperature and pressure. The starting material is not readily soluble in ethanol so it is clearly visible. After 6 h, the amount of starting material was significantly reduced. Hydrogenation was continued overnight, and a large amount of solid was present. Acetonitrile (300 mL) was added and the mixture was heated to dissolve the solid. The catalyst was filtered off using Celite, and the solvent was evaporated from the filtrate to give 6-piperazin-1-yl-3H-pyrimidin-4-one (820 mg, 64%) as a white solid.

Procedure A: Reductive Alkylation

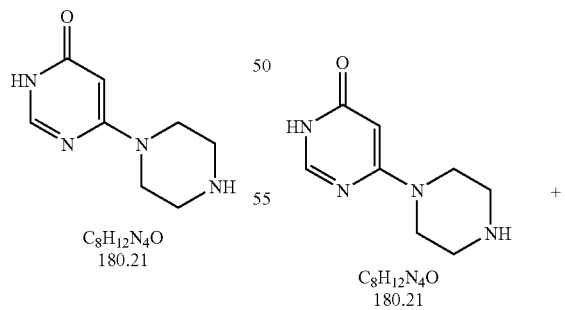

$C_8H_{12}N_4O$
180.21

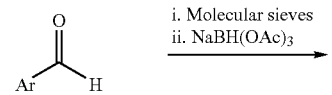

i. Molecular sieves
ii. NaBH(OAc)$_3$

-continued

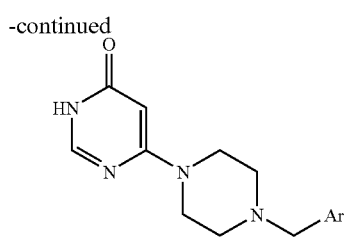

To a suspension of 6-piperazin-1-yl-3H-pyrimidin-4-one in dichloroethane (110 volumes) was added the aldehyde (1.5 equivalents) and molecular sieves. The reaction was shaken at room temperature for 1 hour. Sodium triacetoxyborohydride (2.0 equivalents) was added and the reaction mixture was shaken at room temperature for 48 hours. Methanol (2 volumes) was added and the reaction mixture was allowed to stand for 30 minutes. PL-NCO (Isocyanate) resin (4 equivalents) was added and the reactions shaken at room temperature for 48 hours. The scavenger resin was removed from the crude reaction mixture by filtration through a frit of large pore size. Where solid product was present in the filtrate the solid was removed by filtration and washed with methanol (1 volume) and dichloroethane (1 volume). The liquid filtrate was concentrated and slurried in methanol/dichloroethane (1:1, 1 volume). The slurry was filtered and the solid desired product was washed with methanol (1 volume) and dichloroethane (1 volume). Where no slurry formed the resulting solution was loaded onto MP-TsOH resin (3 equivalents) and washed with methanol, dichloroethane, methanol, dichloroethane and methanol. The desired product was eluted with 7M ammonia in methanol (0.5 volumes×5) and concentrated.

Procedure B: Reductive Alkylation

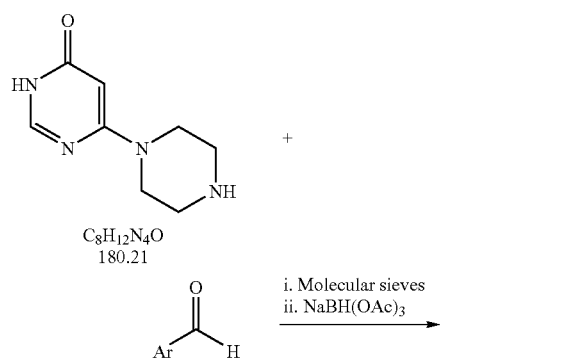

A mixture of 6-piperazin-1-yl-3H-pyrimidin-4-one (Intermediate 4) and 4A molecular sieves in dichloroethane (0.05 M) was stirred at room temperature under nitrogen for 10 min. The aldehyde (1.5 equivalents) was added and the mixture was stirred at room temperature for 1 h. Sodium triacetoxyborohydride (2.0-2.5 equivalents) was added and the mixture was stirred at room temperature for 48 h. The solvent was evaporated under reduced pressure and the residue was purified over silica gel (100-200 mesh), eluting with 5-10% methanol/dichloromethane, to give the product.

Example 1

6-[4-(3-Methyl-benzyl)-piperazin-1-yl]-3H-pyrimidin-4-one

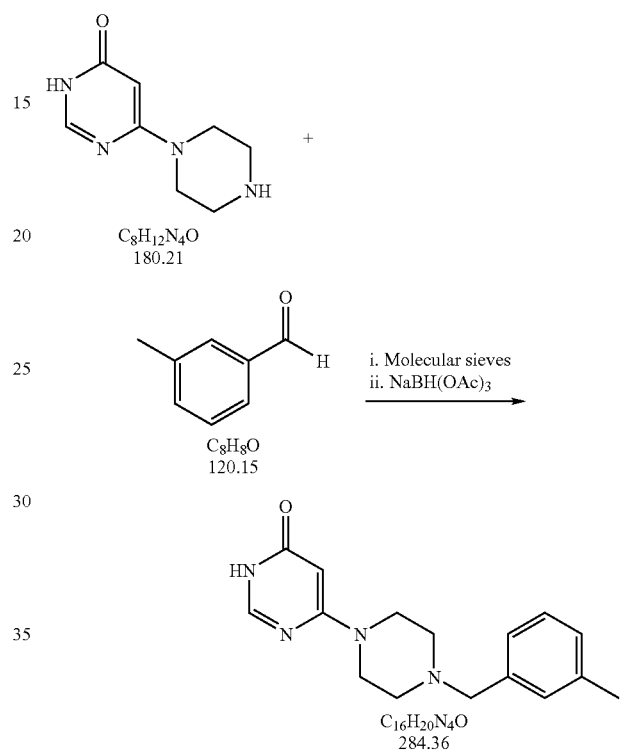

6-[4-(3-Methyl-benzyl)-piperazin-1-yl]-3H-pyrimidin-4-one was prepared using Procedure A from 6-piperazin-1-yl-3H-pyrimidin-4-one (Intermediate 4) and m-tolualdehyde. Mass spectrum (ES) MH+=285.

Example 2

6-[4-(2-Methyl-benzyl)-piperazin-1-yl]-3H-pyrimidin-4-one

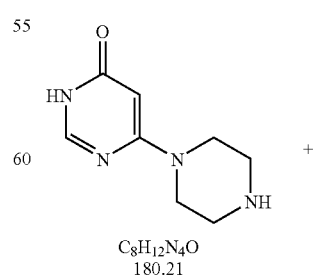

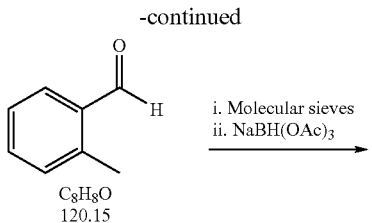

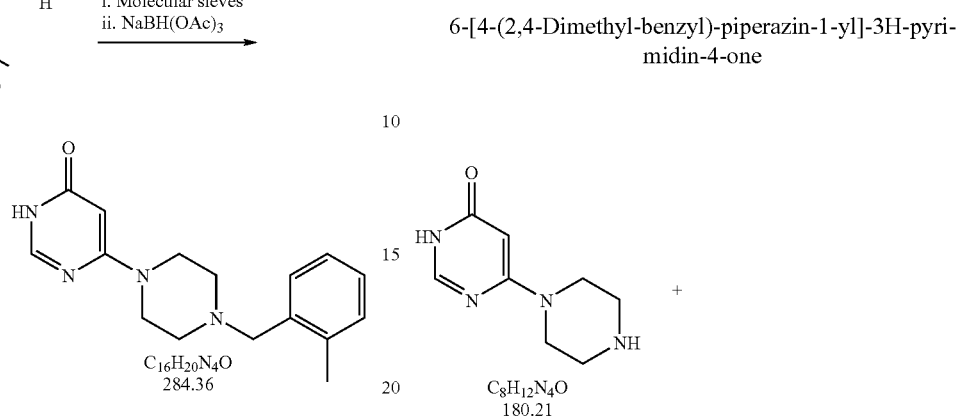

6-[4-(2-Methyl-benzyl)-piperazin-1-yl]-3H-pyrimidin-4-one was prepared using Procedure A from 6-piperazin-1-yl-3H-pyrimidin-4-one (Intermediate 4) and o-tolualdehyde. Mass spectrum (ES) MH+=285.

Example 3

6-[4-(2,6-Dimethyl-benzyl)-piperazin-1-yl]-3H-pyrimidin-4-one

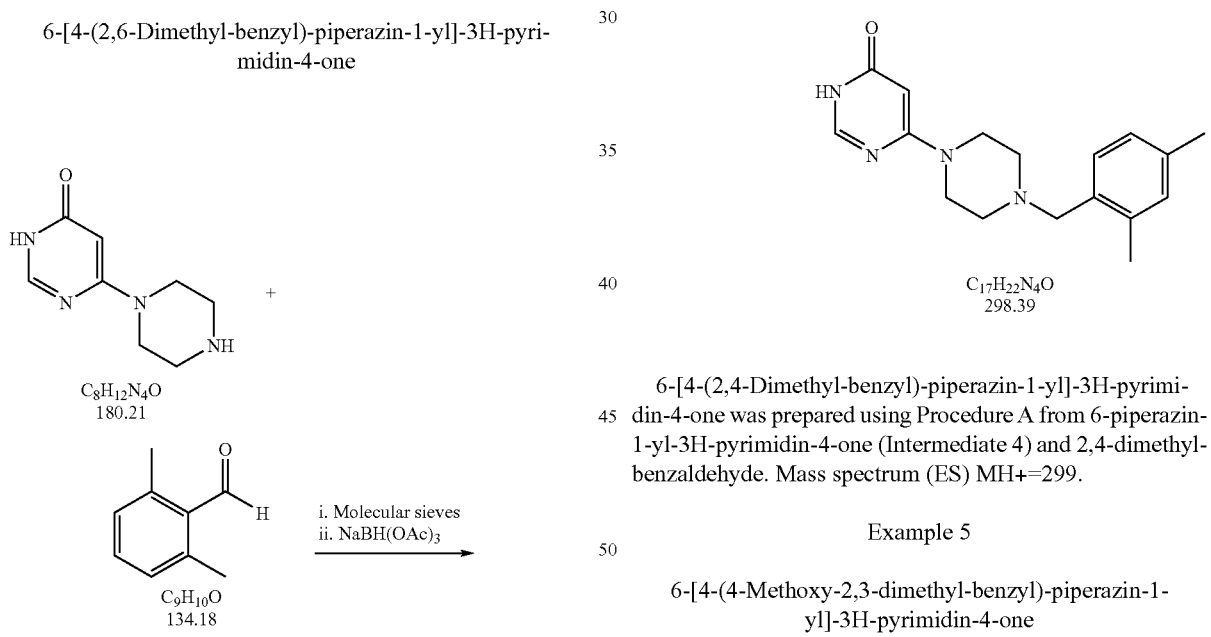

6-[4-(2,6-Dimethyl-benzyl)-piperazin-1-yl]-3H-pyrimidin-4-one was prepared using Procedure A from 6-piperazin-1-yl-3H-pyrimidin-4-one (Intermediate 4) and 2,6-dimethyl-benzaldehyde. Mass spectrum (ES) MH+=299.

Example 4

6-[4-(2,4-Dimethyl-benzyl)-piperazin-1-yl]-3H-pyrimidin-4-one

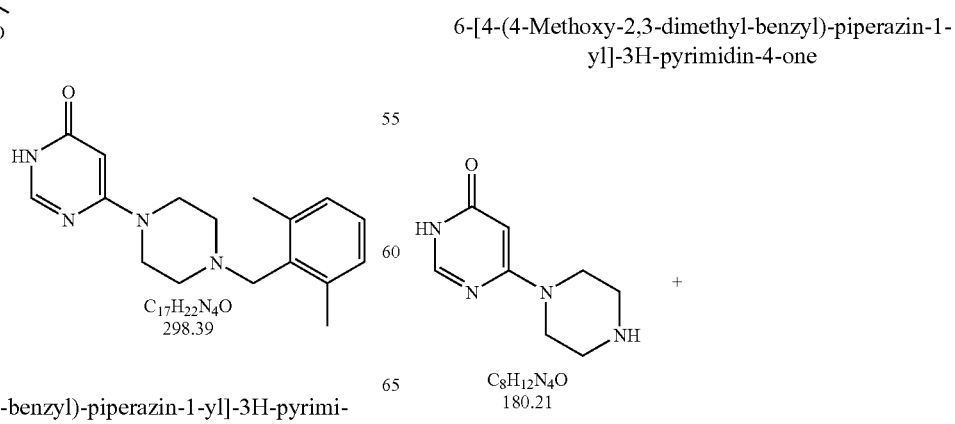

6-[4-(2,4-Dimethyl-benzyl)-piperazin-1-yl]-3H-pyrimidin-4-one was prepared using Procedure A from 6-piperazin-1-yl-3H-pyrimidin-4-one (Intermediate 4) and 2,4-dimethyl-benzaldehyde. Mass spectrum (ES) MH+=299.

Example 5

6-[4-(4-Methoxy-2,3-dimethyl-benzyl)-piperazin-1-yl]-3H-pyrimidin-4-one

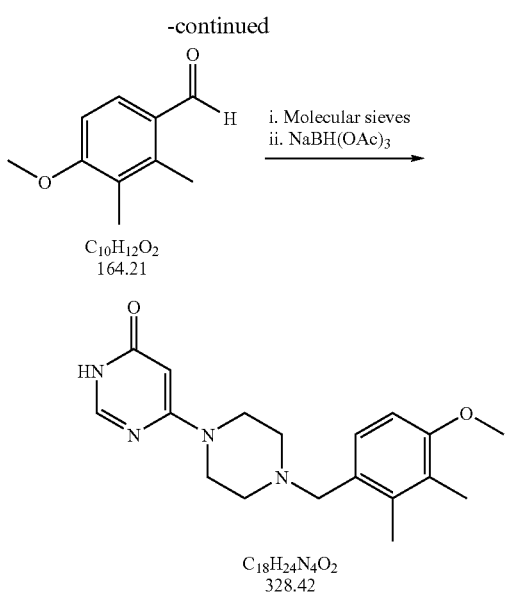

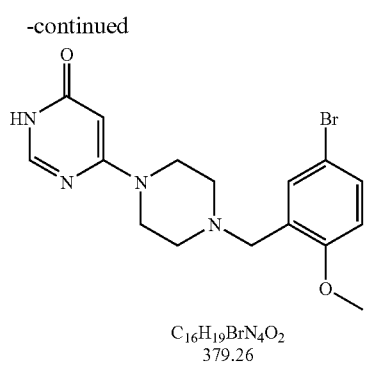

6-[4-(5-Bromo-2-methoxy-benzyl)-piperazin-1-yl]-3H-pyrimidin-4-one was prepared using Procedure A from 6-piperazin-1-yl-3H-pyrimidin-4-one (Intermediate 4) and 5-bromo-2-methoxybenzaldehyde. Mass spectrum (ES) MH+=379.

Example 7

6-[4-(5-Bromo-2-hydroxy-3-methoxy-benzyl)-piperazin-1-yl]-3H-pyrimidin-4-one

6-[4-(4-Methoxy-2,3-dimethyl-benzyl)-piperazin-1-yl]-3H-pyrimidin-4-one was prepared using Procedure A from 6-piperazin-1-yl-3H-pyrimidin-4-one (Intermediate 4) and 2,3-dimethylanisaldehyde. Mass spectrum (ES) MH+=329.

Example 6

6-[4-(5-Bromo-2-methoxy-benzyl)-piperazin-1-yl]-3H-pyrimidin-4-one

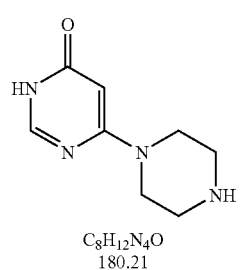

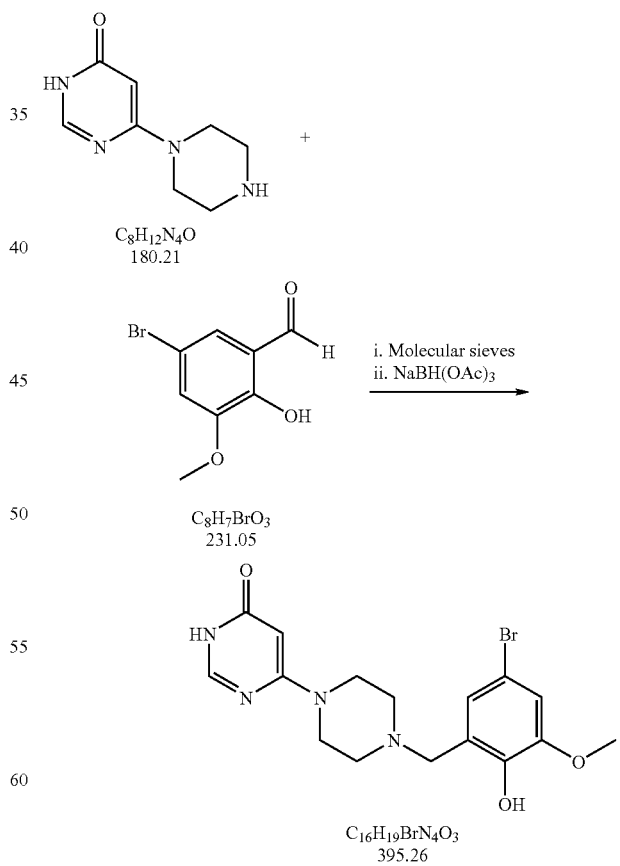

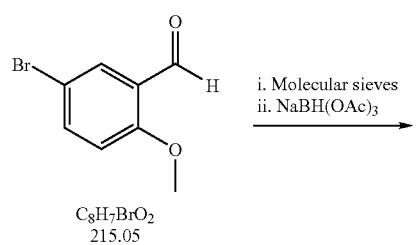

6-[4-(5-Bromo-2-hydroxy-3-methoxy-benzyl)-piperazin-1-yl]-3H-pyrimidin-4-one was prepared using Procedure A from 6-piperazin-1-yl-3H-pyrimidin-4-one (Intermediate 4) and 5-bromo-2-hydroxy-3-methoxybenzaldehyde. Mass spectrum (ES) MH+=395.

Example 8

6-[4-(2-Trifluoromethyl-benzyl)-piperazin-1-yl]-3H-pyrimidin-4-one

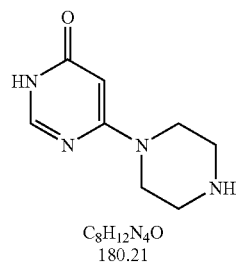

C$_8$H$_{12}$N$_4$O
180.21

+

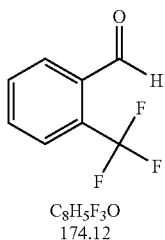

i. Molecular sieves
ii. NaBH(OAc)$_3$
⟶

C$_8$H$_5$F$_3$O
174.12

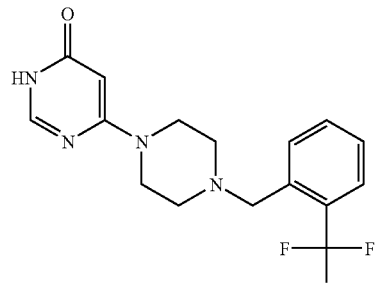

C$_{16}$H$_{17}$F$_3$N$_4$O
338.34

6-[4-(2-Trifluoromethyl-benzyl)-piperazin-1-yl]-3H-pyrimidin-4-one was prepared using Procedure A from 6-piperazin-1-yl-3H-pyrimidin-4-one (Intermediate 4) and 2-(trifluoromethyl)benzaldehyde. Mass spectrum (ES) MH+=339.

Example 9

6-[4-(2,5-Bis-trifluoromethyl-benzyl)-piperazin-1-yl]-3H-pyrimidin-4-one

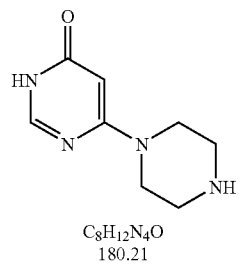

C$_8$H$_{12}$N$_4$O
180.21

+

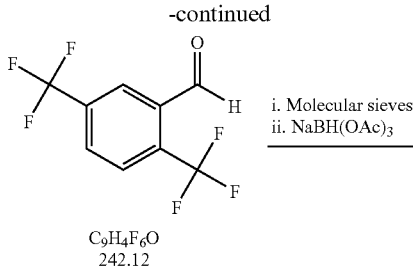

C$_9$H$_4$F$_6$O
242.12 i. Molecular sieves
ii. NaBH(OAc)$_3$
⟶

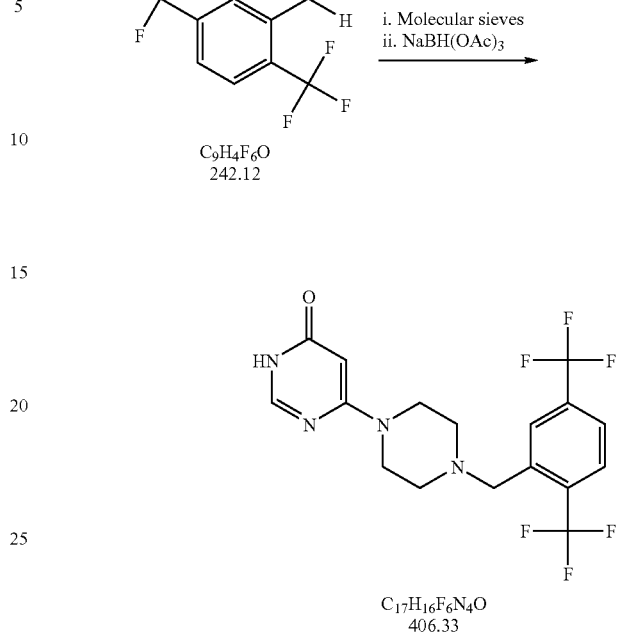

C$_{17}$H$_{16}$F$_6$N$_4$O
406.33

6-[4-(2,5-Bis-trifluoromethyl-benzyl)-piperazin-1-yl]-3H-pyrimidin-4-one was prepared using Procedure A from 6-piperazin-1-yl-3H-pyrimidin-4-one (Intermediate 4) and 2,5-bis(trifluoromethyl)benzaldehyde. Mass spectrum (ES) MH+=407.

Example 10

3-[4-(6-Oxo-1,6-dihydro-pyrimidin-4-yl)-piperazin-1-ylmethyl]-benzonitrile

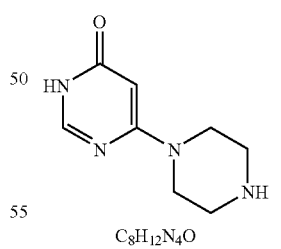

C$_8$H$_{12}$N$_4$O
180.21

+

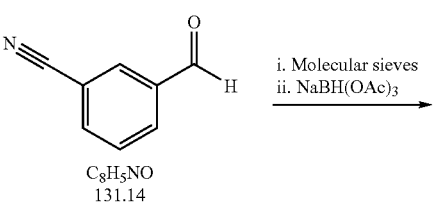

C$_8$H$_5$NO
131.14 i. Molecular sieves
ii. NaBH(OAc)$_3$
⟶

-continued

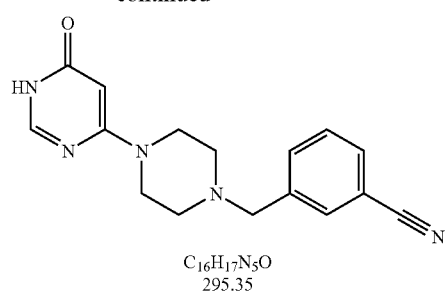

C₁₆H₁₇N₅O
295.35

3-[4-(6-Oxo-1,6-dihydro-pyrimidin-4-yl)-piperazin-1-yl-methyl]-benzonitrile was prepared using Procedure A from 6-piperazin-1-yl-3H-pyrimidin-4-one (Intermediate 4) and 3-cyanobenzaldehyde. Mass spectrum (ES) MH+=296.

Example 11

2-Fluoro-5-[4-(6-oxo-1,6-dihydro-pyrimidin-4-yl)-piperazin-1-ylmethyl]-benzo-nitrile

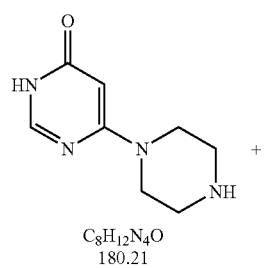

C₈H₁₂N₄O
180.21

+

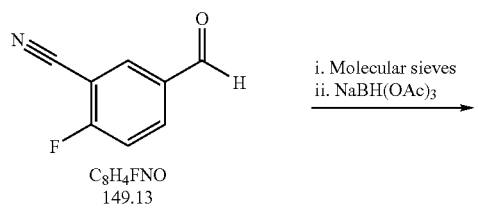

C₈H₄FNO
149.13 i. Molecular sieves
ii. NaBH(OAc)₃
→

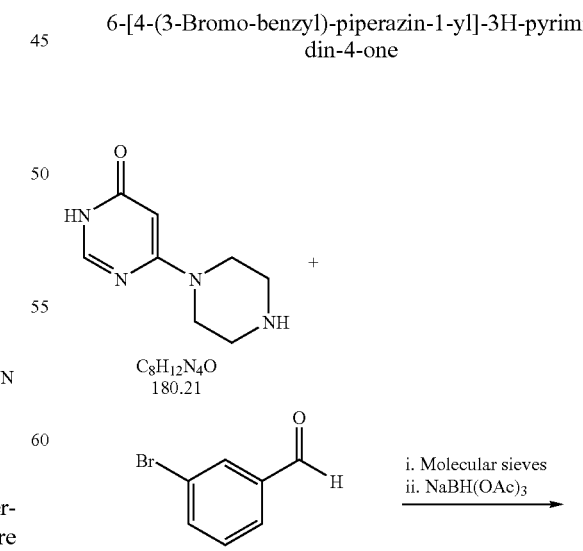

C₁₆H₁₆FN₅O
313.34

2-Fluoro-5-[4-(6-oxo-1,6-dihydro-pyrimidin-4-yl)-piperazin-1-ylmethyl]-benzonitrile was prepared using Procedure A from 6-piperazin-1-yl-3H-pyrimidin-4-one (Intermediate 4) and 2-fluoro-5-formylbenzonitrile. Mass spectrum (ES) MH+=314.

Example 12

6-[4-(3-Chloro-benzyl)-piperazin-1-yl]-3H-pyrimidin-4-one

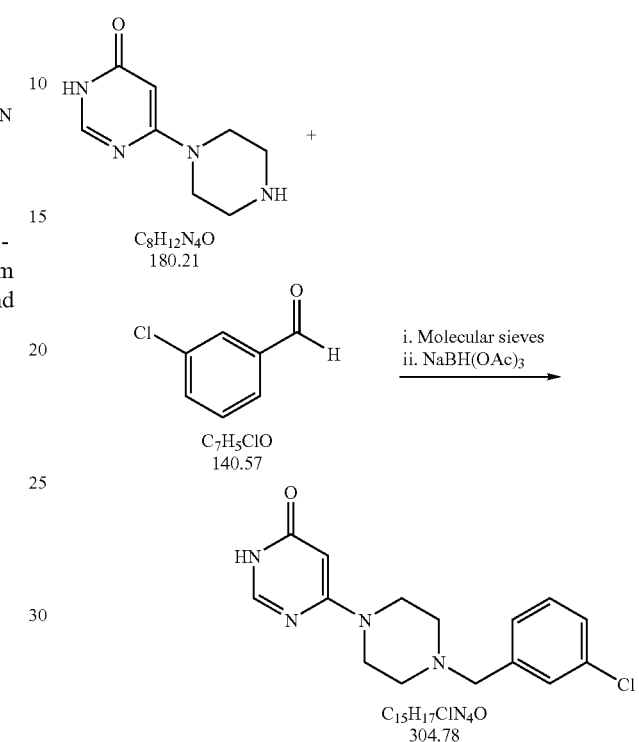

6-[4-(3-Chloro-benzyl)-piperazin-1-yl]-3H-pyrimidin-4-one was prepared using Procedure A from 6-piperazin-1-yl-3H-pyrimidin-4-one (Intermediate 4) and 3-chlorobenzaldehyde. Mass spectrum (ES) MH+=305.

Example 13

6-[4-(3-Bromo-benzyl)-piperazin-1-yl]-3H-pyrimidin-4-one

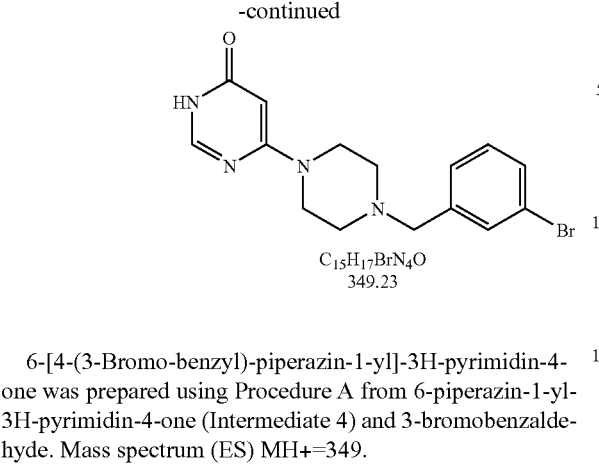

6-[4-(3-Bromo-benzyl)-piperazin-1-yl]-3H-pyrimidin-4-one was prepared using Procedure A from 6-piperazin-1-yl-3H-pyrimidin-4-one (Intermediate 4) and 3-bromobenzaldehyde. Mass spectrum (ES) MH+=349.

Example 14

6-[4-(2,6-Dichloro-benzyl)-piperazin-1-yl]-3H-pyrimidin-4-one

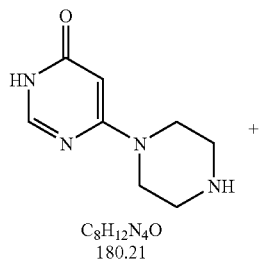

6-[4-(2,6-Dichloro-benzyl)-piperazin-1-yl]-3H-pyrimidin-4-one was prepared using Procedure A from 6-piperazin-1-yl-3H-pyrimidin-4-one (Intermediate 4) and 2,6-dichlorobenzaldehyde (available from Fluka). Mass spectrum (ES) MH+=339.

Example 15

6-[4-(3,4-Dichloro-benzyl)-piperazin-1-yl]-3H-pyrimidin-4-one

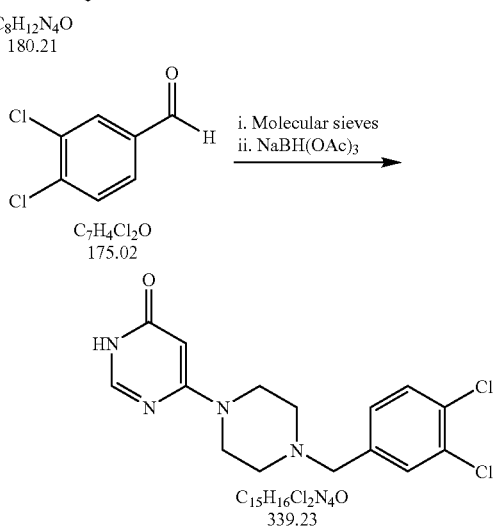

6-[4-(3,4-Dichloro-benzyl)-piperazin-1-yl]-3H-pyrimidin-4-one was prepared using Procedure A from 6-piperazin-1-yl-3H-pyrimidin-4-one (Intermediate 4) and 3,4-dichlorobenzaldehyde. Mass spectrum (ES) MH+=339.

Example 16

6-[4-(2,3,6-Trichloro-benzyl)-piperazin-1-yl]-3H-pyrimidin-4-one

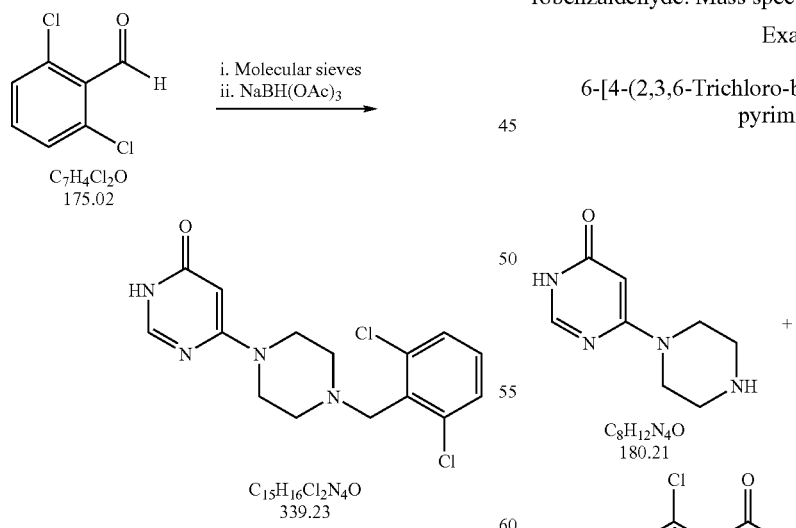

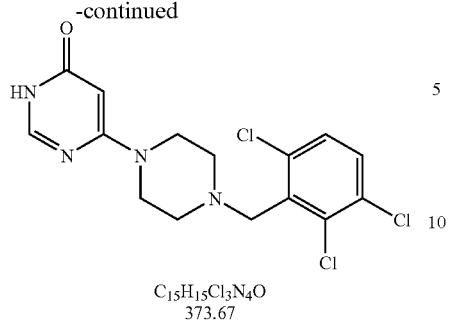

C₁₅H₁₅Cl₃N₄O
373.67

6-[4-(2,3,6-Trichloro-benzyl)-piperazin-1-yl]-3H-pyrimidin-4-one was prepared using Procedure A from 6-piperazin-1-yl-3H-pyrimidin-4-one (Intermediate 4) and 2,3,6-trichlorobenzaldehyde. Mass spectrum (ES) MH+=373.

Example 17

6-[4-(2,3-Dichloro-benzyl)-piperazin-1-yl]-3H-pyrimidin-4-one

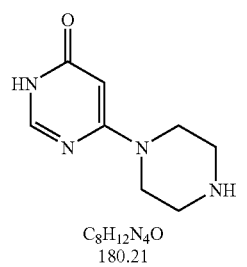

C₈H₁₂N₄O
180.21

+

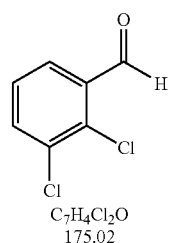

C₇H₄Cl₂O
175.02 i. Molecular sieves
ii. NaBH(OAc)₃
→

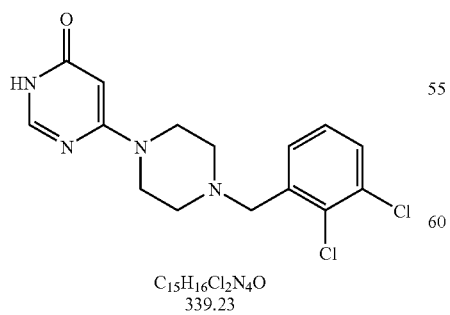

C₁₅H₁₆Cl₂N₄O
339.23

6-[4-(2,3-Dichloro-benzyl)-piperazin-1-yl]-3H-pyrimidin-4-one was prepared using Procedure A from 6-piperazin-1-yl-3H-pyrimidin-4-one (Intermediate 4) and 2,3-dichlorobenzaldehyde. Mass spectrum (ES) MH+=339.

Example 18

6-[4-(2-Bromo-benzyl)-piperazin-1-yl]-3H-pyrimidin-4-one

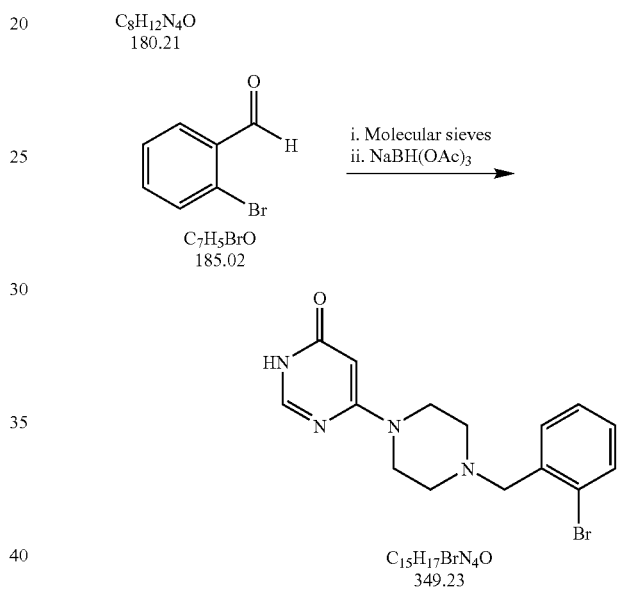

C₈H₁₂N₄O
180.21

+

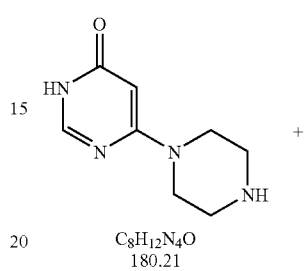

C₇H₅BrO
185.02 i. Molecular sieves
ii. NaBH(OAc)₃
→

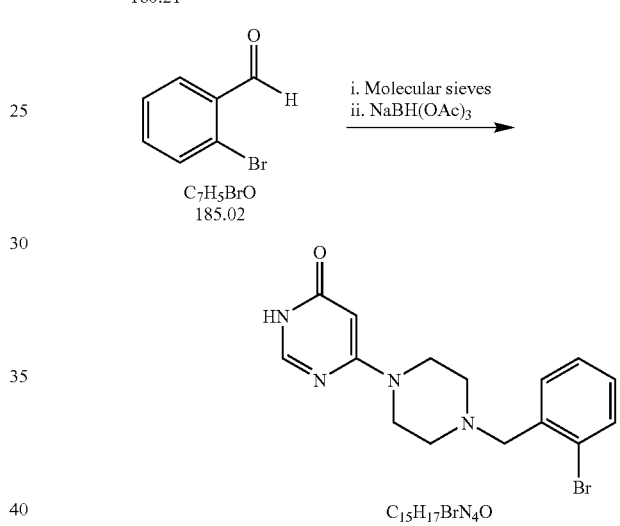

C₁₅H₁₇BrN₄O
349.23

6-[4-(2-Bromo-benzyl)-piperazin-1-yl]-3H-pyrimidin-4-one was prepared using Procedure A from 6-piperazin-1-yl-3H-pyrimidin-4-one (Intermediate 4) and 2-bromobenzaldehyde. Mass spectrum (ES) MH+=349.

Example 19

6-[4-(5-Bromo-2-fluoro-benzyl)-piperazin-1-yl]-3H-pyrimidin-4-one

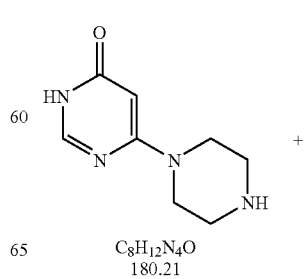

C₈H₁₂N₄O
180.21

+

-continued

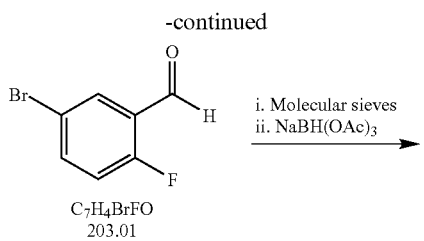

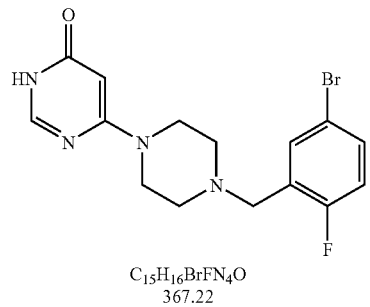

6-[4-(5-Bromo-2-fluoro-benzyl)-piperazin-1-yl]-3H-pyrimidin-4-one was prepared using Procedure A from 6-piperazin-1-yl-3H-pyrimidin-4-one (Intermediate 4) and 5-bromo-2-fluorobenzaldehyde. Mass spectrum (ES) MH+=367.

Example 20

6-[4-(2-Bromo-5-fluoro-benzyl)-piperazin-1-yl]-3H-pyrimidin-4-one

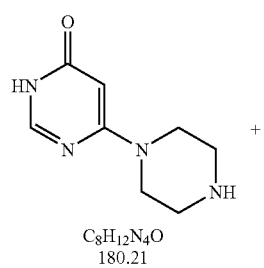

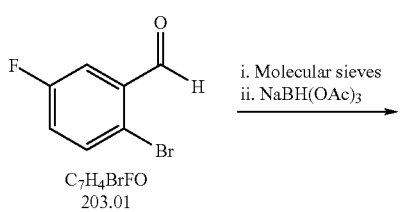

-continued

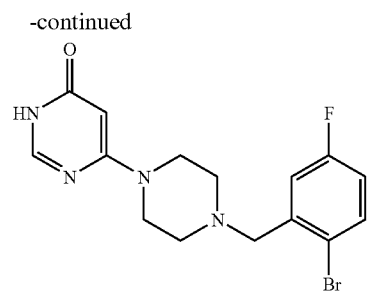

6-[4-(2-Bromo-5-fluoro-benzyl)-piperazin-1-yl]-3H-pyrimidin-4-one was prepared using Procedure A from 6-piperazin-1-yl-3H-pyrimidin-4-one (Intermediate 4) and 2-bromo-5-fluorobenzaldehyde. Mass spectrum (ES) MH+=367.

Example 21

6-[4-(3,4-Difluoro-benzyl)-piperazin-1-yl]-3H-pyrimidin-4-one

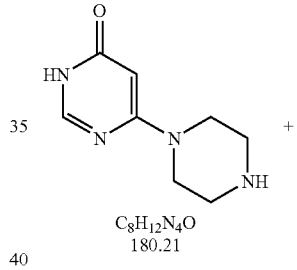

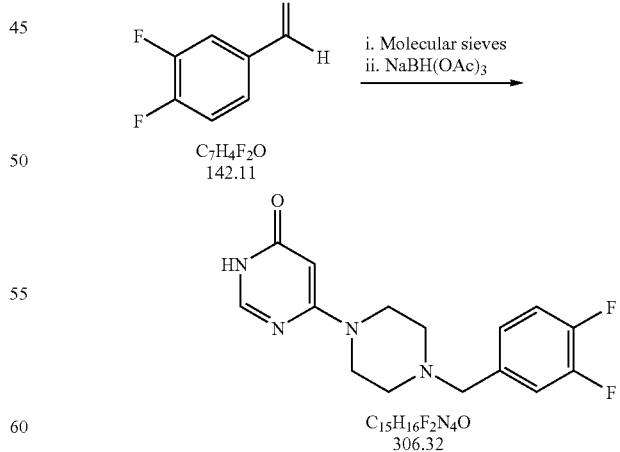

6-[4-(3,4-Difluoro-benzyl)-piperazin-1-yl]-3H-pyrimidin-4-one was prepared using Procedure A from 6-piperazin-1-yl-3H-pyrimidin-4-one (Intermediate 4) and 3,4-difluorobenzaldehyde. Mass spectrum (ES) MH+=307.

Example 22

6-[4-(3-Chloro-4-fluoro-benzyl)-piperazin-1-yl]-3H-pyrimidin-4-one

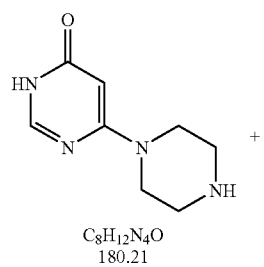

C$_8$H$_{12}$N$_4$O
180.21

+

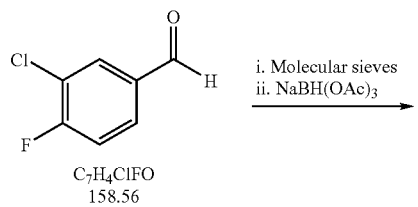

C$_7$H$_4$ClFO
158.56 i. Molecular sieves
ii. NaBH(OAc)$_3$

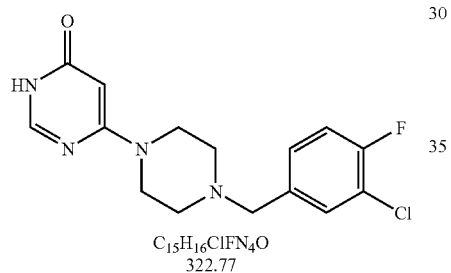

C$_{15}$H$_{16}$ClFN$_4$O
322.77

6-[4-(3-Chloro-4-fluoro-benzyl)-piperazin-1-yl]-3H-pyrimidin-4-one was prepared using Procedure A from 6-piperazin-1-yl-3H-pyrimidin-4-one (Intermediate 4) and 3-chloro-4-fluorobenzaldehyde. Mass spectrum (ES) MH+=323.

Example 23

6-[4-(2-Chloro-5-trifluoromethyl-benzyl)-piperazin-1-yl]-3H-pyrimidin-4-one

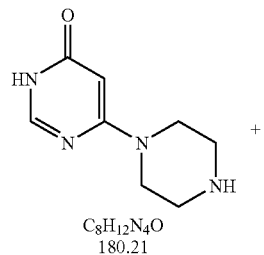

C$_8$H$_{12}$N$_4$O
180.21

+

-continued

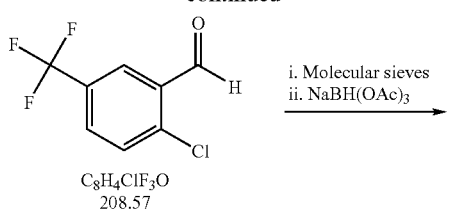

C$_8$H$_4$ClF$_3$O
208.57 i. Molecular sieves
ii. NaBH(OAc)$_3$

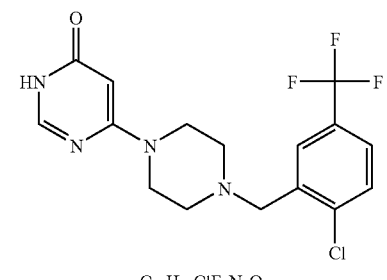

C$_{16}$H$_{16}$ClF$_3$N$_4$O
372.78

6-[4-(2-Chloro-5-trifluoromethyl-benzyl)-piperazin-1-yl]-3H-pyrimidin-4-one was prepared using Procedure A from 6-piperazin-1-yl-3H-pyrimidin-4-one (Intermediate 4) and 2-chloro-5-(trifluoromethyl)benzaldehyde. Mass spectrum (ES) MH+=373.

Example 24

6-[4-(3,5-Dichloro-2-hydroxy-benzyl)-piperazin-1-yl]-3H-pyrimidin-4-one

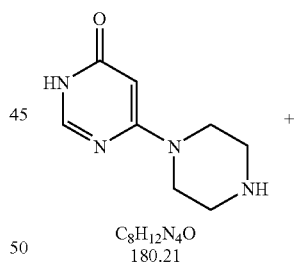

C$_8$H$_{12}$N$_4$O
180.21

+

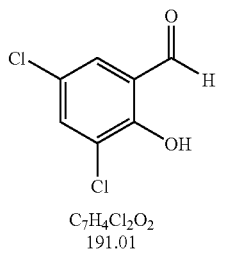

C$_7$H$_4$Cl$_2$O$_2$
191.01 i. Molecular sieves
ii. NaBH(OAc)$_3$

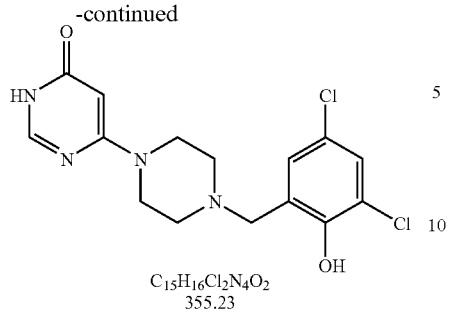

C₁₅H₁₆Cl₂N₄O₂
355.23

6-[4-(3,5-Dichloro-2-hydroxy-benzyl)-piperazin-1-yl]-3H-pyrimidin-4-one was prepared using Procedure A from 6-piperazin-1-yl-3H-pyrimidin-4-one (Intermediate 4) and 3,5-dichlorosalicylaldehyde. Mass spectrum (ES) MH+=355.

Example 25

6-[4-(5-Bromo-2-hydroxy-benzyl)-piperazin-1-yl]-3H-pyrimidin-4-one

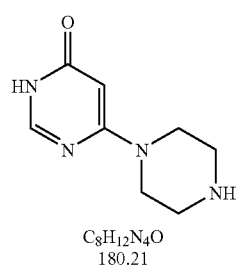

C₈H₁₂N₄O
180.21

+

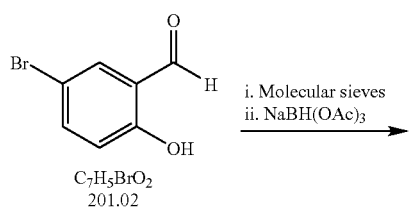

C₇H₅BrO₂
201.02 i. Molecular sieves
ii. NaBH(OAc)₃ →

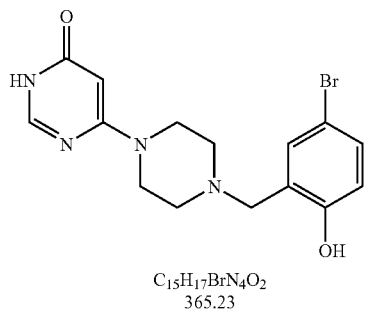

C₁₅H₁₇BrN₄O₂
365.23

6-[4-(5-Bromo-2-hydroxy-benzyl)-piperazin-1-yl]-3H-pyrimidin-4-one was prepared using Procedure A from 6-piperazin-1-yl-3H-pyrimidin-4-one (Intermediate 4) and 5-bromosalicylaldehyde. Mass spectrum (ES) MH+=365.

Example 26

6-[4-(3-Nitro-benzyl)-piperazin-1-yl]-3H-pyrimidin-4-one

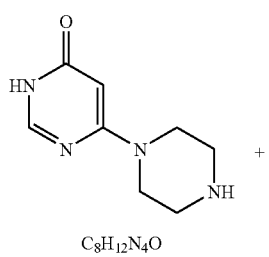

C₈H₁₂N₄O
180.21

+

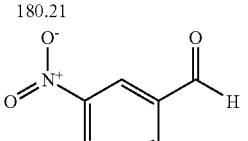

C₇H₅NO₃
151.12 i. Molecular sieves
ii. NaBH(OAc)₃ →

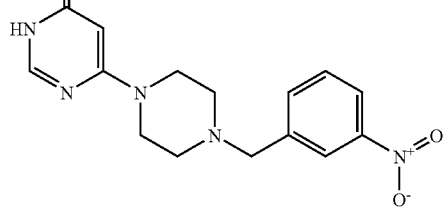

C₁₅H₁₇N₅O₃
315.33

6-[4-(3-Nitro-benzyl)-piperazin-1-yl]-3H-pyrimidin-4-one was prepared using Procedure A from 6-piperazin-1-yl-3H-pyrimidin-4-one (Intermediate 4) and 3-nitrobenzaldehyde. Mass spectrum (ES) MH+=316.

Example 27

6-[4-(2-Nitro-benzyl)-piperazin-1-yl]-3H-pyrimidin-4-one

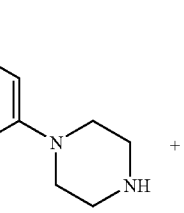

C₈H₁₂N₄O
180.21

+

-continued

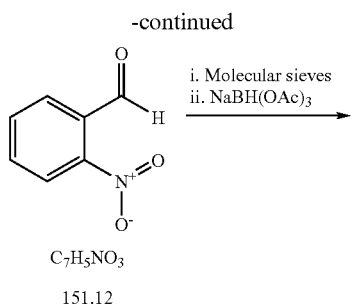

C7H5NO3
151.12

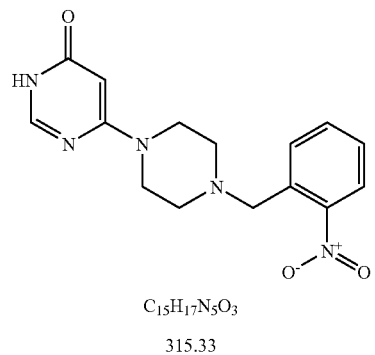

C15H17N5O3
315.33

6-[4-(2-Nitro-benzyl)-piperazin-1-yl]-3H-pyrimidin-4-one was prepared using Procedure A from 6-piperazin-1-yl-3H-pyrimidin-4-one (Intermediate 4) and 2-nitrobenzaldehyde. Mass spectrum (ES) MH+=316.

Example 28

6-[4-(5-Chloro-2-nitro-benzyl)-piperazin-1-yl]-3H-pyrimidin-4-one

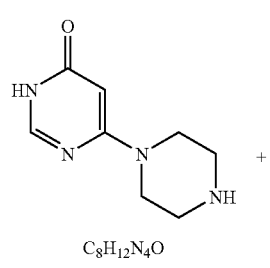

C8H12N4O
180.21

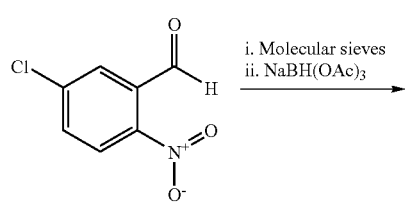

C7H4ClNO3
185.57

-continued

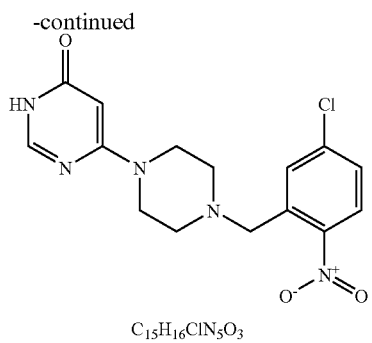

C15H16ClN5O3
349.78

6-[4-(5-Chloro-2-nitro-benzyl)-piperazin-1-yl]-3H-pyrimidin-4-one was prepared using Procedure A from 6-piperazin-1-yl-3H-pyrimidin-4-one (Intermediate 4) and 5-chloro-2-nitrobenzaldehyde. Mass spectrum (ES) MH+=350.

Example 29

6-[4-(2-Hydroxy-5-nitro-benzyl)-piperazin-1-yl]-3H-pyrimidin-4-one

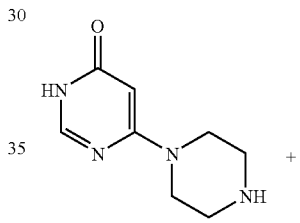

C8H12N4O
180.21

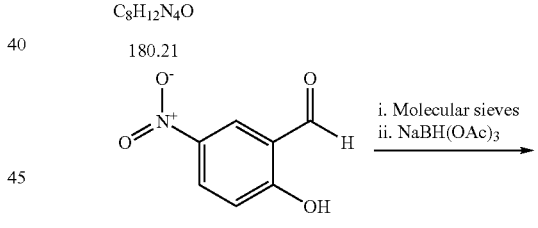

C7H5NO4
167.12

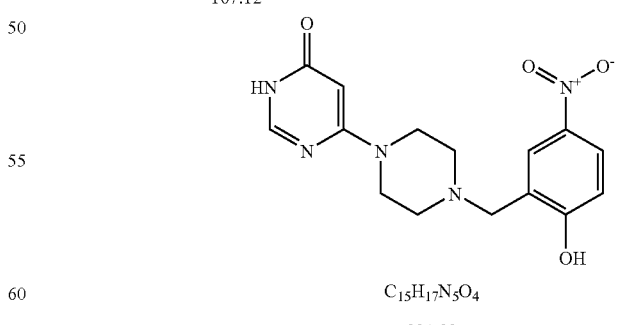

C15H17N5O4
331.33

6-[4-(2-Hydroxy-5-nitro-benzyl)-piperazin-1-yl]-3H-pyrimidin-4-one was prepared using Procedure A from 6-piperazin-1-yl-3H-pyrimidin-4-one (Intermediate 4) and 2-hydroxy-5-nitrobenzaldehyde. Mass spectrum (ES) MH+=332.

Example 30

6-[4-(2-Hydroxy-benzyl)-piperazin-1-yl]-3H-pyrimidin-4-one

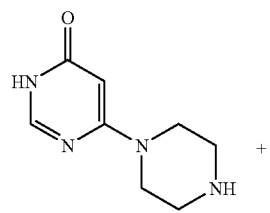

C$_8$H$_{12}$N$_4$O
180.21

+

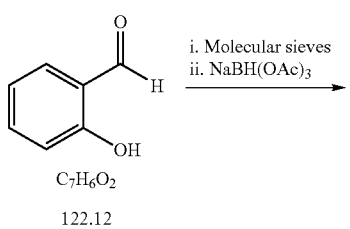

C$_7$H$_6$O$_2$
122.12 i. Molecular sieves
ii. NaBH(OAc)$_3$

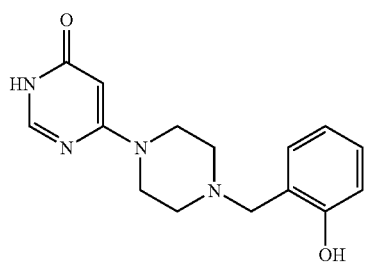

C$_{15}$H$_{18}$N$_4$O$_2$
286.34

6-[4-(2-Hydroxy-benzyl)-piperazin-1-yl]-3H-pyrimidin-4-one was prepared using Procedure A from 6-piperazin-1-yl-3H-pyrimidin-4-one (Intermediate 4) and salicylaldehyde. Mass spectrum (ES) MH+=287.

Example 31

6-[4-(2-Hydroxy-5-trifluoromethoxy-benzyl)-piperazin-1-yl]-3H-pyrimidin-4-one

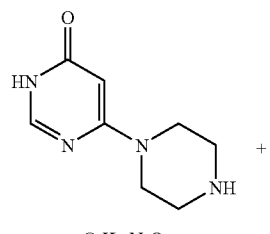

C$_8$H$_{12}$N$_4$O
180.21

+

-continued

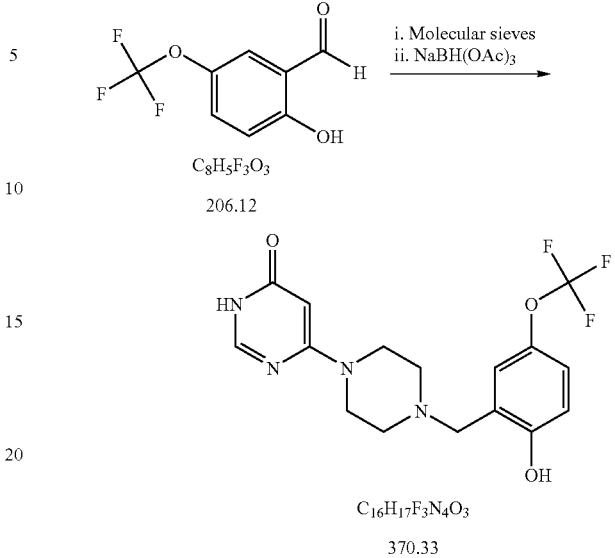

C$_8$H$_5$F$_3$O$_3$
206.12 i. Molecular sieves
ii. NaBH(OAc)$_3$

C$_{16}$H$_{17}$F$_3$N$_4$O$_3$
370.33

6-[4-(2-Hydroxy-5-trifluoromethoxy-benzyl)-piperazin-1-yl]-3H-pyrimidin-4-one was prepared using Procedure A from 6-piperazin-1-yl-3H-pyrimidin-4-one (Intermediate 4) and 2-hydroxy-5-trifluoromethoxybenzaldehyde. Mass spectrum (ES) MH+=371.

Example 32

6-[4-(2-Chloro-4-fluoro-benzyl)-piperazin-1-yl]-3H-pyrimidin-4-one

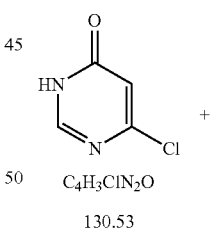

C$_4$H$_3$ClN$_2$O
130.53

+

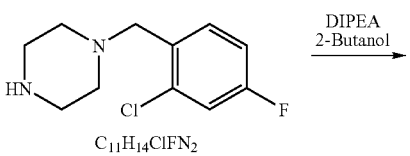

C$_{11}$H$_{14}$ClFN$_2$
228.70

DIPEA
2-Butanol

-continued

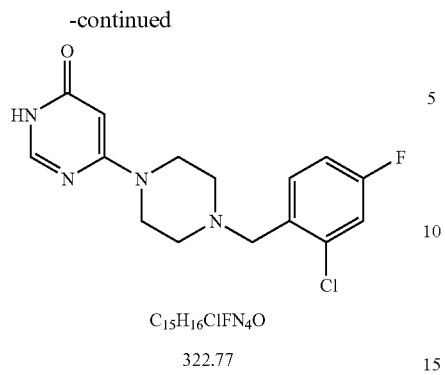

C₁₅H₁₆ClFN₄O
322.77

A mixture of 6-chloro-3H-pyrimidin-4-one (Intermediate 4; 100 mg, 0.77 mmol), 1-(2-chloro-6-fluorobenzyl)piperazine (Oakwood; 87 mg, 0.38 mmol), and diisopropylethylamine (200 μL, 1.1 mmol) in 2-butanol (5 mL) was heated in a sealed scintillation vial on a hot plate at about 80° C. for 8 hours and then allowed to cool to room temperature and stand at room temperature for 40 hours. The mixture was filtered. The solid was washed with 2-butanol and air-dried to give 6-[4-(2-chloro-6-fluorobenzyl)-piperazin-1-yl]-3H-pyrimidin-4-one (21 mg, 17%) as a white solid, mp 255-256° C. (dec). $^1$H NMR (d$_6$-DMSO) δ 2.41-2.44 (m, 4H), 3.42-3.45 (m, 4H), 5.24 (s, 1H), 7.19-7.24 (m, 1H), 7.40-7.43 (m, 1H), 7.51-7.56 (m, 1H), 7.87 (s, 1H), 11.61 (br s, 1H). LRMS ES+M+H 323. HRMS Calcd. for C$_{15}$H$_{17}$ClFN$_4$O (M+H), 323.1070. Found, 323.1069.

Example 33

6-[4-(3-Fluoro-benzyl)-piperazin-1-yl]-3H-pyrimidin-4-one

C₄H₃ClN₂O
130.53

+

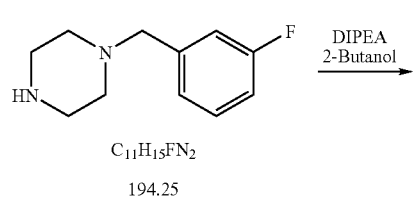

C₁₁H₁₅FN₂
194.25

-continued

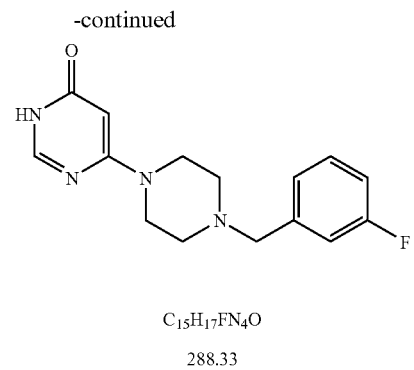

C₁₅H₁₇FN₄O
288.33

A mixture of 6-chloro-3H-pyrimidin-4-one (Intermediate 4; 100 mg, 0.77 mmol), 1-(3-fluorobenz-yl)piperazine (Aldrich; 194 mg, 1.0 mmol), and diisopropylethylamine (200 μL, 1.1 mmol) in 2-butanol (5 mL) was heated in a sealed scintillation vial on a hot plate at about 80° C. for 8 hours and then allowed to cool and stand at room temperature overnight. The mixture was filtered. The solid was washed with 2-butanol and air-dried to give 6-[4-(3-fluoro-benzyl)-piperazin-1-yl]-3H-pyrimidin-4-one (145 mg, 65%), as a white solid, mp 273-275° C. (dec.). $^1$H NMR (d$_6$-DMSO) δ 2.36-2.39 (m, 4H), 3.44-3.47 (m, 4H), 5.23 (s, 1H), 7.04-7.16 (m, 3H), 7.32-7.40 (m, 1H), 7.86 (s, 1H), 11.60 (s, 1H). LRMS ES+M+H 289. HRMS Calcd. for C$_{15}$H$_{18}$FN$_4$O (M+H), 289.1459. Found, 289.1459.

Example 34

6-[4-(4-Bromo-2-fluoro-benzyl)-piperazin-1-yl]-3H-pyrimidin-4-one

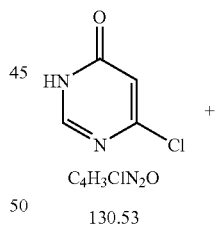

C₄H₃ClN₂O
130.53

+

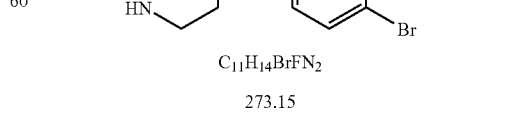

C₁₁H₁₄BrFN₂
273.15

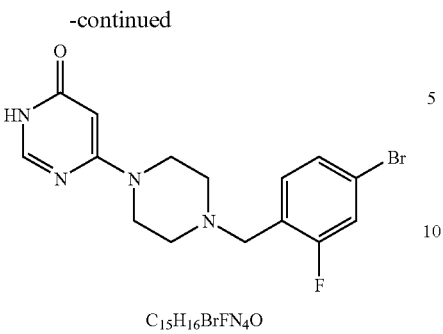

C₁₅H₁₆BrFN₄O
367.22

A mixture of 6-chloro-3H-pyrimidin-4-one (Intermediate 4; 100 mg, 0.77 mmol), 1-(4-bromo-2-fluorobenzyl)piperazine (Aldrich; 273 mg, 1.0 mmol), and diisopropylethylamine (200 μL, 1.1 mmol) in 2-butanol (5 mL) was heated in a sealed scintillation vial on a hot plate at about 80° C. for 14 hours and then allowed to cool and stand at room temperature overnight. The mixture was filtered. The solid was washed with 2-butanol and air-dried to give 4-(4-bromo-2-fluoro-benzyl)-piperazin-1-yl]-3H-pyrimidin-4-one (229 mg, 81%), as a white solid, mp 275-276° C. $^1$H NMR (d$_6$-DMSO) δ 2.37-2.40 (m, 4H), 3.42-3.45 (m, 4H), 5.22 (s,1H), 7.35-7.41 (m, 2H), 7.49-7.52 (m, 1H), 7.86 (s, 1H), 11.59 (br s, 1H). LRMS ES+M+H 367. HRMS Calcd. for C$_{15}$H$_{17}$BrFN$_4$O (M+H), 367.0565. Found, 367.0564.

Example 35

6-[4-(3-Bromo-2-methyl-benzyl)-piperazin-1-yl]-3H-pyrimidin-4-one

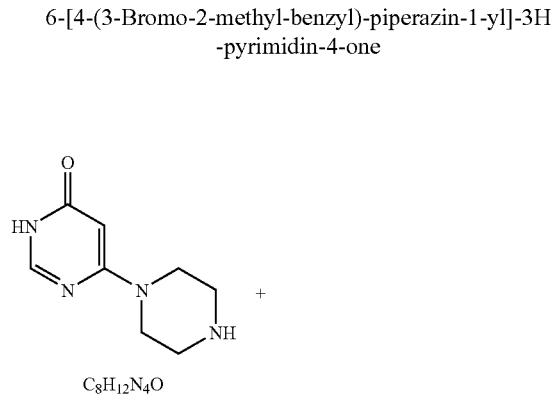

C₈H₁₂N₄O
180.21

C₈H₇BrO
199.05

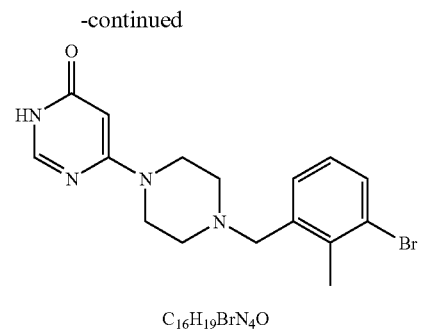

C₁₆H₁₉BrN₄O
363.26

6-[4-(3-Bromo-2-methyl-benzyl)-piperazin-1-yl]-3H-pyrimidin-4-one was prepared using Procedure B from 6-piperazin-1-yl-3H-pyrimidin-4-one (Intermediate 4) and 3-bromo-2-methylbenzaldehyde (which may be prepared as described in N. Subasinghe et al. WO 2003099805). $^1$H NMR (400 MHz, CDCl$_3$) δ 2.45-2.50 (m, 7H), 3.48-3.54 (m, 6H), 5.36 (s, 1H), 6.97-7.01 (m, 1H), 7.16-7.21 (m, 1H), 7.47-7.49 (m, 1H), 7.82 (s, 1H), 11.95 (br s, 1H). Mass spectrum (ES) MH+=363.

Example 36

6-(4-Biphenyl-2-ylmethyl-piperazin-1-yl)-3H-pyrimidin-4-one

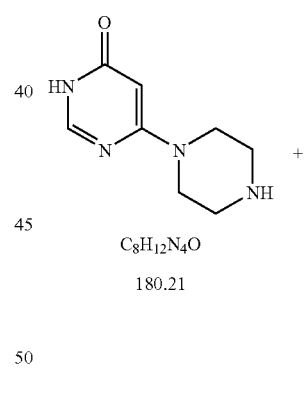

C₈H₁₂N₄O
180.21

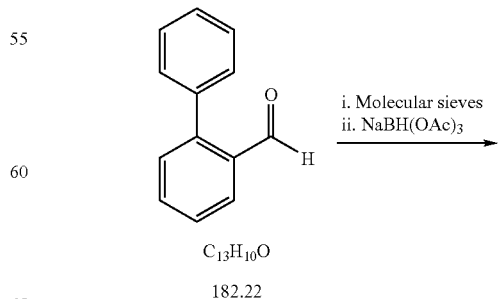

C₁₃H₁₀O
182.22

-continued

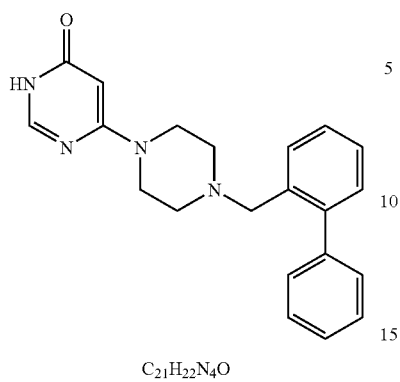

C₂₁H₂₂N₄O 346.44

6-(4-Biphenyl-2-ylmethyl-piperazin-1-yl)-3H-pyrimidin-4-one was prepared using Procedure B from 6-piperazin-1-yl-3H-pyrimidin-4-one (Intermediate 4) and 2-phenylbenzaldehyde (available from Aldrich). $^1$H NMR (400 MHz, CDCl₃) δ 2.36-2.39 (m, 4H), 3.43-3.48 (m, 6H), 5.32 (s, 1H), 7.25-7.40 (m, 8H), 7.80 (s, 1H), 12.20 (br s, 1H). Mass spectrum (ES) MH+=347.

Example 37

6-(4-Benzo[1,3]dioxol-4-ylmethyl-piperazin-1-yl)-3H-pyrimidin-4-one

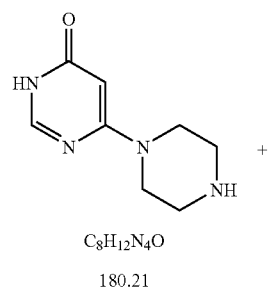

C₈H₁₂N₄O 180.21

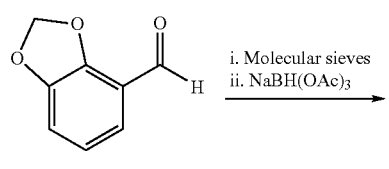

C₈H₆O₃

150.14

-continued

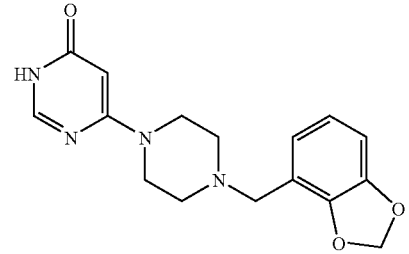

C₁₆H₁₈N₄O₃

314.35

6-(4-Benzo[1,3]dioxol-4-ylmethyl-piperazin-1-yl)-3H-pyrimidin-4-one was prepared using Procedure B from 6-piperazin-1-yl-3H-pyrimidin-4-one (Intermediate 4) and 2,3-(methylenedioxy)benzaldehyde (available from Aldrich). $^1$H NMR (400 MHz, CDCl₃) δ 2.51-2.54 (m, 4H), 3.48-3.58 (m, 6H), 5.35 (s, 1H), 5.95 (s, 2H), 6.74-6.82 (m, 2H), 7.81 (s, 1H). Mass spectrum (ES) MH+=315.

Example 38

6-[4-(2-Hydroxy-3-methyl-benzyl)-piperazin-1-yl]-3H-pyrimidin-4-one

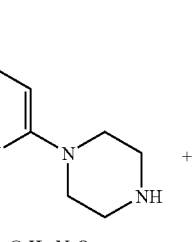

C₈H₁₂N₄O 180.21

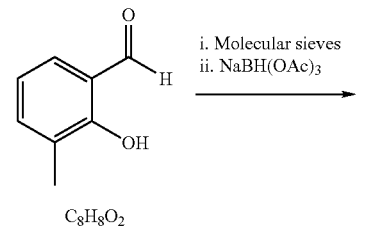

C₈H₈O₂

136.15

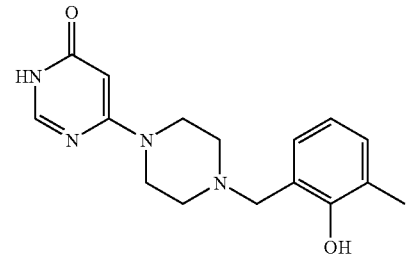

C₁₆H₂₀N₄O₂

300.36

6-[4-(2-Hydroxy-3-methyl-benzyl)-piperazin-1-yl]-3H-pyrimidin-4-one was prepared using Procedure B from 6-piperazin-1-yl-3H-pyrimidin-4-one (Intermediate 4) and 2-hydroxy-3-methylbenzaldehyde (available from Aldrich). $^1$H NMR (400 MHz, CDCl$_3$) δ 2.25 (s, 3H), 2.58-2.63 (m, 4H), 3.48-3.63 (m, 4H), 3.71 (s, 2H), 5.39 (s, 1H), 6.69-6.73 (m, 1H), 6.82-6.83 (m, 1H), 7.05-7.07 (m, 1H), 7.84 (s, 1H), 10.60 (br s, 1H), 12.60 (br s, 1H). Mass spectrum (ES) MH+=301.

Example 39

6-[4-(2-Hydroxy-5-methyl-benzyl)-piperazin-1-yl]-3H-pyrimidin-4-one

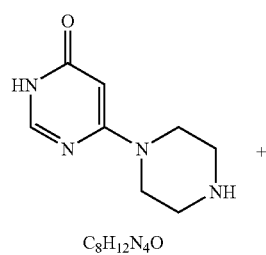

C$_8$H$_{12}$N$_4$O
180.21

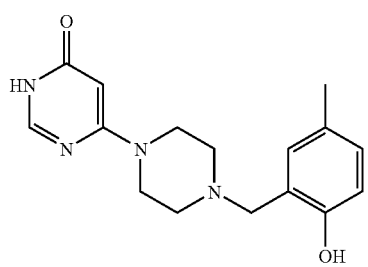

C$_8$H$_8$O$_2$
136.15 i. Molecular sieves
ii. NaBH(OAc)$_3$

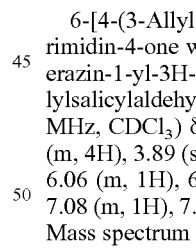

C$_{16}$H$_{20}$N$_4$O$_2$
300.36

6-[4-(2-Hydroxy-5-methyl-benzyl)-piperazin-1-yl]-3H-pyrimidin-4-one was prepared using Procedure B from 6-piperazin-1-yl-3H-pyrimidin-4-one (Intermediate 4) and 2-hydroxy-5-methylbenzaldehyde (available from Aldrich) (available from Aldrich). $^1$H NMR (400 MHz, CDCl$_3$) δ 2.23 (s, 3H), 2.58-2.63 (m, 4H), 3.48-3.63 (m, 4H), 3.69 (s, 2H), 5.39 (s, 1H), 6.73-6.78 (m, 2H), 6.98-7.00 (m, 1H), 7.85 (s, 1H), 10.10 (br s, 1H), 12.75 (br s, 1H). Mass spectrum (ES) MH+=301.

Example 40

6-[4-(3-Allyl-2-hydroxy-benzyl)-piperazin-1-yl]-3H-pyrimidin-4-one

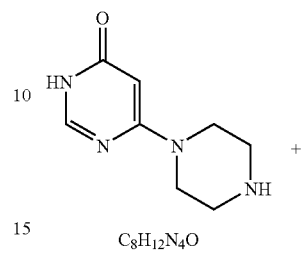

C$_8$H$_{12}$N$_4$O
180.21

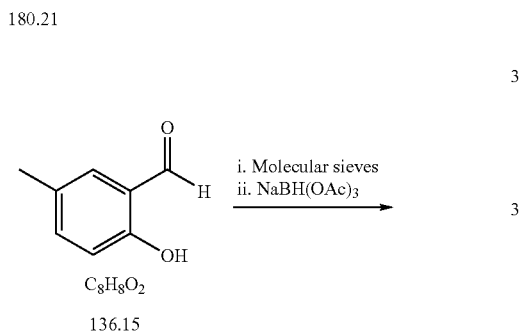

C$_{10}$H$_{10}$O$_2$
162.19 i. Molecular sieves
ii. NaBH(OAc)$_3$

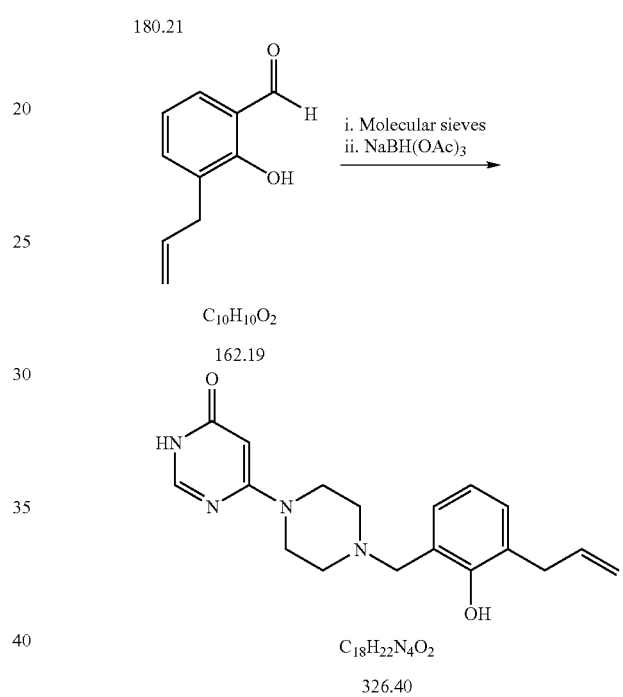

C$_{18}$H$_{22}$N$_4$O$_2$
326.40

6-[4-(3-Allyl-2-hydroxy-benzyl)-piperazin-1-yl]-3H-pyrimidin-4-one was prepared using Procedure B from 6-piperazin-1-yl-3H-pyrimidin-4-one (Intermediate 4) and 3-allylsalicylaldehyde (available from Aldrich). $^1$H NMR (400 MHz, CDCl$_3$) δ 2.58-2.64 (m, 4H), 3.38 (s, 2H), 3.58-3.63 (m, 4H), 3.89 (s, 2H), 5.06-5.15 (m, 2H), 5.39 (s, 1H), 5.97-6.06 (m, 1H), 6.73-6.77 (m, 1H), 6.85-6.89 (m, 1H), 6.99-7.08 (m, 1H), 7.84 (s, 1H), 10.65 (br s, 1H), 12.31 (br s, 1H). Mass spectrum (ES) MH+=327.

Example 41

6-[4-(3-tert-Butyl-2-hydroxy-benzyl)-piperazin-1-yl]-3H-pyrimidin-4-one

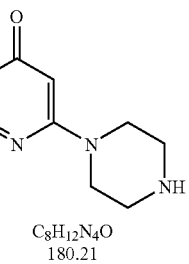

C$_8$H$_{12}$N$_4$O
180.21

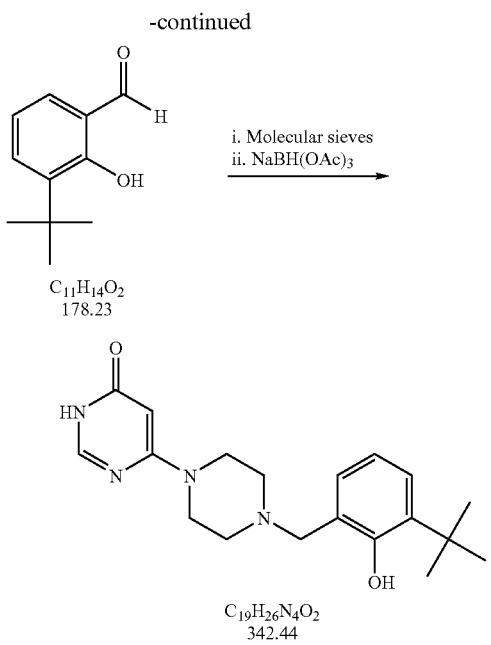

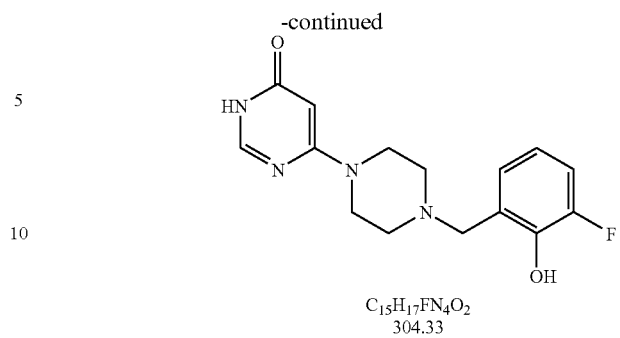

6-[4-(3-Fluoro-2-hydroxy-benzyl)-piperazin-1-yl]-3H-pyrimidin-4-one was prepared using Procedure B from 6-piperazin-1-yl-3H-pyrimidin-4-one (Intermediate 4) and 3-fluorosalicylaldehyde (available from Aldrich). $^1$H NMR (400 MHz, CDCl$_3$) δ 2.62-2.66 (m, 4H), 3.58-3.65 (m, 4H), 3.79 (s, 2H), 5.40 (s, 1H), 6.71-6.76 (m, 2H), 6.99-7.03 (m, 1H), 7.84 (s, 1H), 11.85 (br s, 1H). Mass spectrum (ES) MH+=305.

6-[4-(3-tert-Butyl-2-hydroxy-benzyl)-piperazin-1-yl]-3H-pyrimidin-4-one was prepared using Procedure B from 6-piperazin-1-yl-3H-pyrimidin-4-one (Intermediate 4) and 3-tert-butyl-2-hydroxybenzaldehyde (available from Aldrich). $^1$H NMR (400 MHz, CDCl$_3$) δ 1.40 (s, 9H), 2.58-2.63 (m, 4H), 3.48-3.60 (m, 4H), 3.73 (s, 2H), 5.40 (s, 1H), 6.72-6.76 (m, 1H), 6.84-6.86 (m, 1H), 7.20-7.22 (m, 1H), 7.85 (s,1H), 10.80 (br s, 1H), 12.65 (br s, 1H). Mass spectrum (ES) MH+=343.

Example 42

6-[4-(3-Fluoro-2-hydroxy-benzyl)-piperazin-1-yl]-3H-pyrimidin-4-one

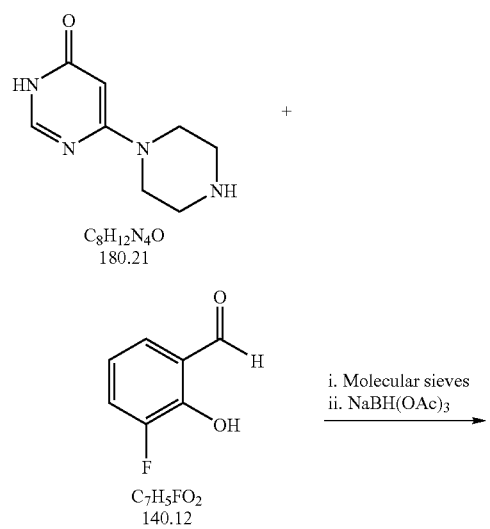

Example 43

6-[4-(5-Fluoro-2-hydroxy-benzyl)-piperazin-1-yl]-3H-pyrimidin-4-one

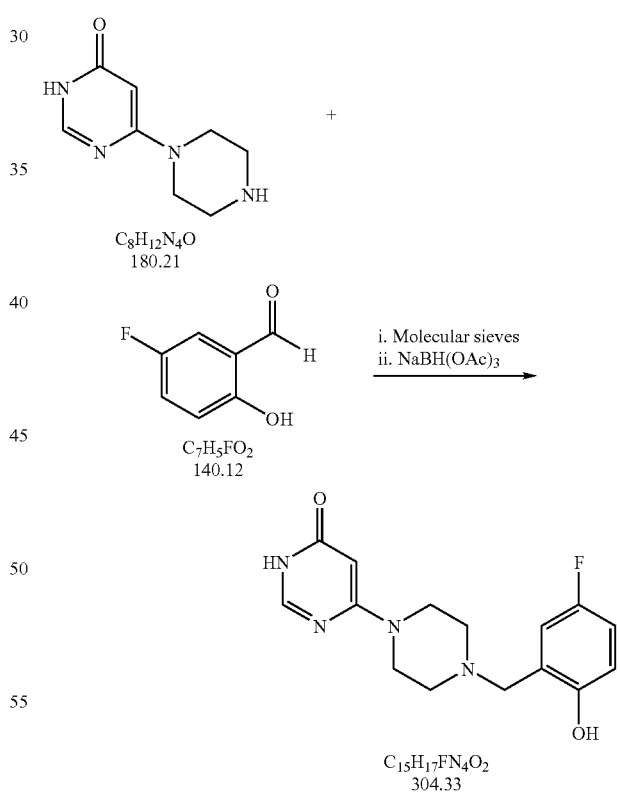

6-[4-(5-Fluoro-2-hydroxy-benzyl)-piperazin-1-yl]-3H-pyrimidin-4-one was prepared using Procedure B from 6-piperazin-1-yl-3H-pyrimidin-4-one (Intermediate 4) and 5-fluoro-2-hydroxybenzaldehyde (available from Aldrich). $^1$H NMR (400 MHz, DMSO-d$_6$) δ 2.45-2.48 (m, 4H), 3.43-3.49 (m, 4H), 3.57 (s, 2H), 5.28 (s, 1H), 6.73-6.80 (m, 1H), 6.89-6.94 (m, 1H), 6.99-7.02 (m, 1H), 7.89 (s, 1H), 9.90 (br s, 1H), 11.64 (br s, 1H). Mass spectrum (ES) MH+=305.

Example 44

6-[4-(3,5-Difluoro-2-hydroxy-benzyl)-piperazin-1-yl]-3H-pyrimidin-4-one

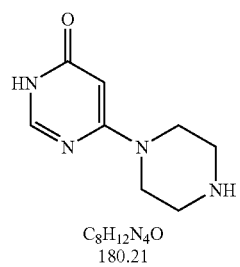

C$_8$H$_{12}$N$_4$O
180.21

+

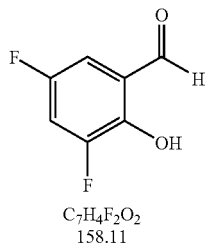

C$_7$H$_4$F$_2$O$_2$
158.11 i. Molecular sieves
ii. NaBH(OAc)$_3$

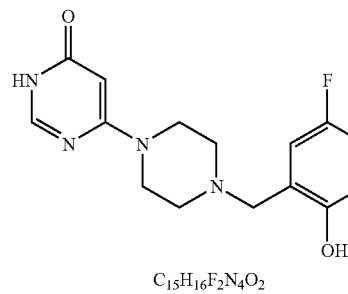

C$_{15}$H$_{16}$F$_2$N$_4$O$_2$
322.32

6-[4-(3,5-Difluoro-2-hydroxy-benzyl)-piperazin-1-yl]-3H-pyrimidin-4-one was prepared using Procedure B from 6-piperazin-1-yl-3H-pyrimidin-4-one (Intermediate 4) and 3,5-difluorosalicylaldehyde (available from Aldrich). $^1$H NMR (400 MHz, DMSO-d$_6$) δ 3.48-3.53 (m, 4H), 3.67 (s, 2H), 5.27 (s, 1H), 6.89-6.91 (m, 1H), 7.09-7.13 (m, 1H), 7.89 (s, 1H), 11.64 (br s, 1H). Mass spectrum (ES) MH+=323.

Example 45

6-[4-(3-Chloro-2-hydroxy-benzyl)-piperazin-1-yl]-3H-pyrimidin-4-one

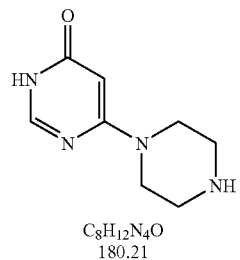

C$_8$H$_{12}$N$_4$O
180.21

+

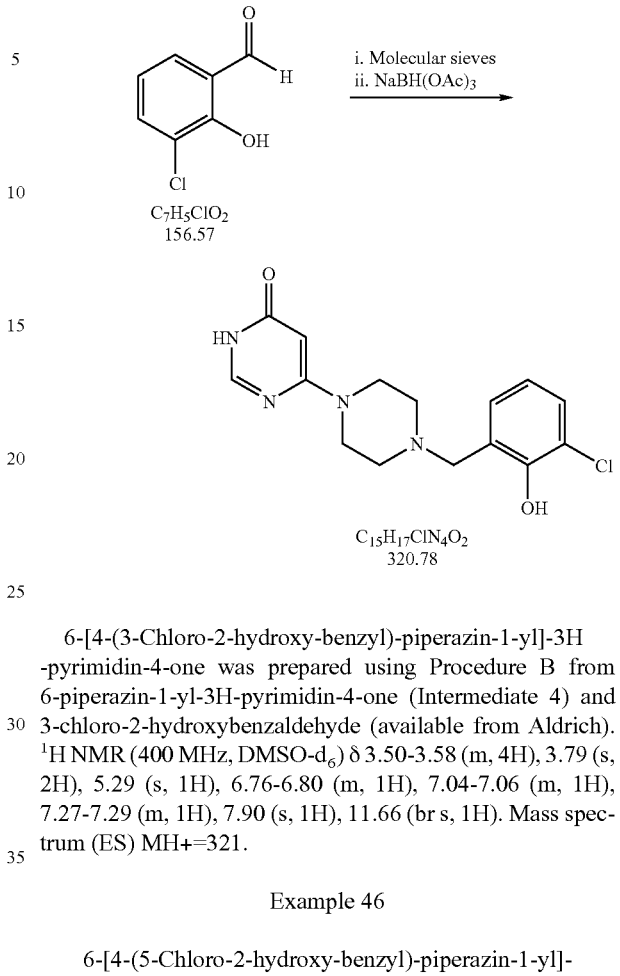

6-[4-(3-Chloro-2-hydroxy-benzyl)-piperazin-1-yl]-3H-pyrimidin-4-one was prepared using Procedure B from 6-piperazin-1-yl-3H-pyrimidin-4-one (Intermediate 4) and 3-chloro-2-hydroxybenzaldehyde (available from Aldrich). $^1$H NMR (400 MHz, DMSO-d$_6$) δ 3.50-3.58 (m, 4H), 3.79 (s, 2H), 5.29 (s, 1H), 6.76-6.80 (m, 1H), 7.04-7.06 (m, 1H), 7.27-7.29 (m, 1H), 7.90 (s, 1H), 11.66 (br s, 1H). Mass spectrum (ES) MH+=321.

Example 46

6-[4-(5-Chloro-2-hydroxy-benzyl)-piperazin-1-yl]-3H-pyrimidin-4-one

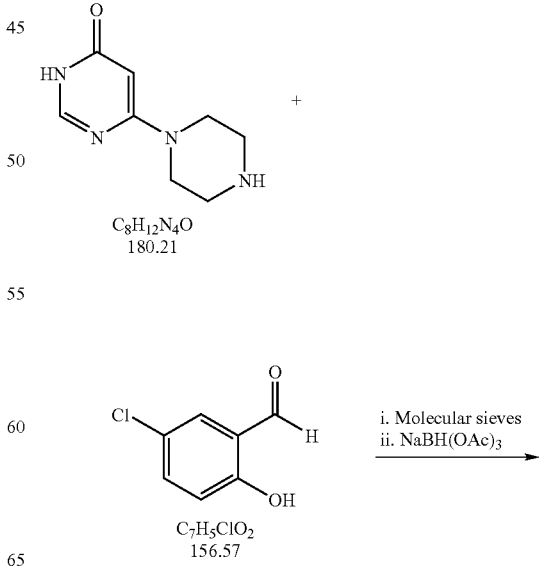

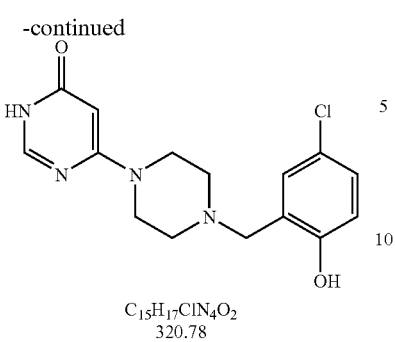

6-[4-(5-Chloro-2-hydroxy-benzyl)-piperazin-1-yl]-3H-pyrimidin-4-one was prepared using Procedure B from 6-piperazin-1-yl-3H-pyrimidin-4-one (Intermediate 4) and 5-chlorosalicylaldehyde (available from Aldrich). $^1$H NMR (400 MHz, CDCl$_3$) δ 2.60-2.64 (m, 4H), 3.58-3.65 (m, 4H), 3.70 (s, 2H), 5.40 (s, 1H), 6.76-6.78 (m, 1H), 6.96-6.99 (m, 1H), 7.13-7.15 (m, 1H), 7.85 (s, 1H), 10.60 (br s, 1H), 12.65 (br s, 1H). Mass spectrum (ES) MH+=321.

Example 47

6-[4-(5-Chloro-2-hydroxy-3-methyl-benzyl)-piperazin-1-yl]-3H-pyrimidin-4-one

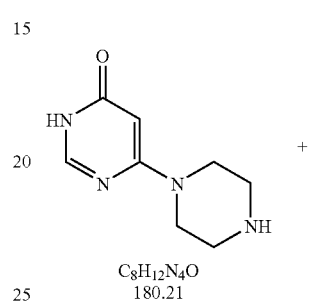

6-[4-(5-Chloro-2-hydroxy-3-methyl-benzyl)-piperazin-1-yl]-3H-pyrimidin-4-one was prepared using Procedure B from 6-piperazin-1-yl-3H-pyrimidin-4-one (Intermediate 4) and 5-chloro-2-hydroxy-3-methylbenzaldehyde (available from Alfa Aesar, Ward Hill, Mass., USA). $^1$H NMR (400 MHz, CDCl$_3$) δ 2.19 (s, 3H), 2.58-2.63 (m, 4H), 3.48-3.67 (m, 6H), 5.40 (s, 1H), 6.80-6.81 (m, 1H), 7.03-7.04 (m, 1H), 7.85 (s, 1H), 10.60 (br s, 1H), 12.45 (br s, 1H). Mass spectrum (ES) MH+=335.

Example 48

6-[4-(3-Bromo-2-hydroxy-benzyl)-piperazin-1-yl]-3H-pyrimidin-4-one

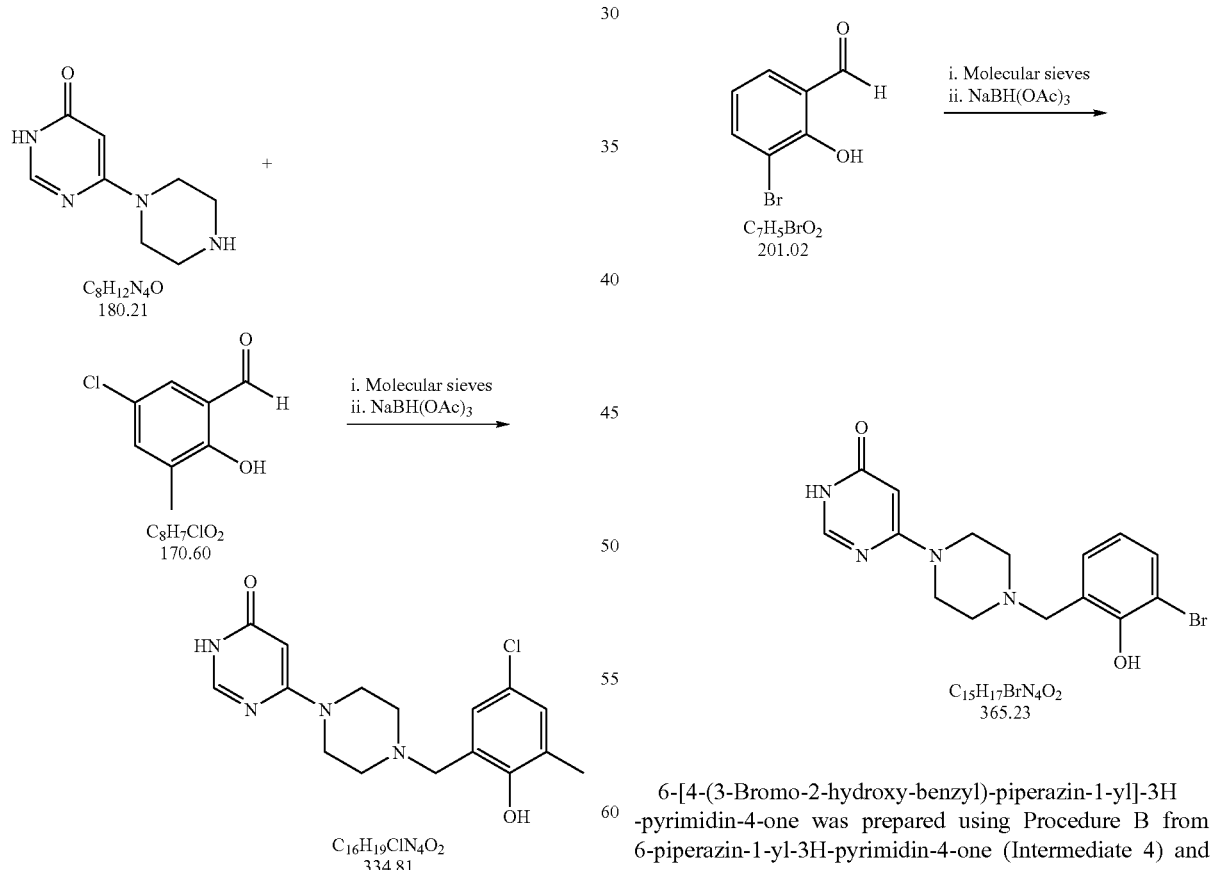

6-[4-(3-Bromo-2-hydroxy-benzyl)-piperazin-1-yl]-3H-pyrimidin-4-one was prepared using Procedure B from 6-piperazin-1-yl-3H-pyrimidin-4-one (Intermediate 4) and 3-bromo-2-hydroxybenzaldehyde (available from Aldrich). $^1$H NMR (400 MHz, CDCl$_3$) δ 2.62-2.66 (m, 4H), 3.60-3.70 (m, 4H), 3.75 (s, 2H), 5.40 (s, 1H), 6.67-6.70 (m, 1H), 6.92-6.94 (m, 1H), 7.43-7.45 (m, 1H), 7.84 (s, 1H), 11.95 (br s, 1H). Mass spectrum (ES) MH+=365.

Example 49

6-[4-(3,5-Dibromo-2-hydroxy-benzyl)-piperazin-1-yl]-3H-pyrimidin-4-one

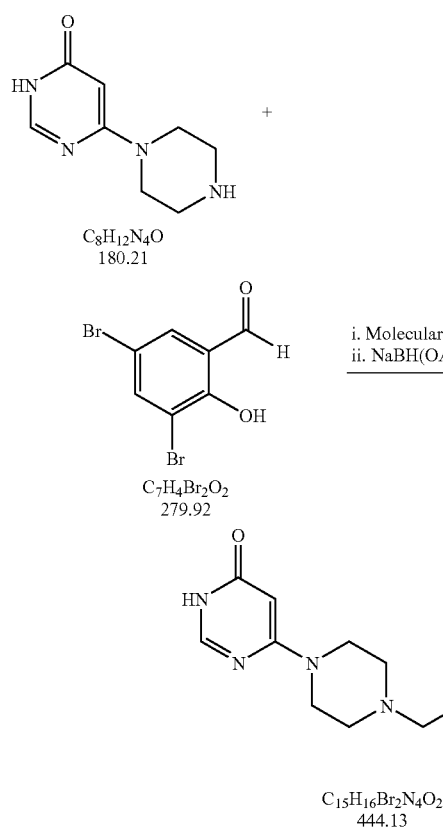

6-[4-(3,5-Dibromo-2-hydroxy-benzyl)-piperazin-1-yl]-3H-pyrimidin-4-one was prepared using Procedure B from 6-piperazin-1-yl-3H-pyrimidin-4-one (Intermediate 4) and 3,5-dibromosalicylaldehyde (available from Aldrich). $^1$H NMR (400 MHz, CDCl$_3$) δ 2.62-2.66 (m, 4H), 3.48 (s, 1H), 3.58-3.65 (m, 4H), 3.72 (s, 2H), 5.40 (s, 1H), 7.07 (s, 1H), 7.58 (s, 1H), 7.84 (s, 1H), 11.90 (br s, 1H). Mass spectrum (ES) MH+=445.

Example 50

6-[4-(3-Bromo-5-chloro-2-hydroxy-benzyl)-piperazin-1-yl]-3H-pyrimidin-4-one

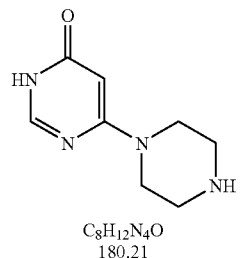

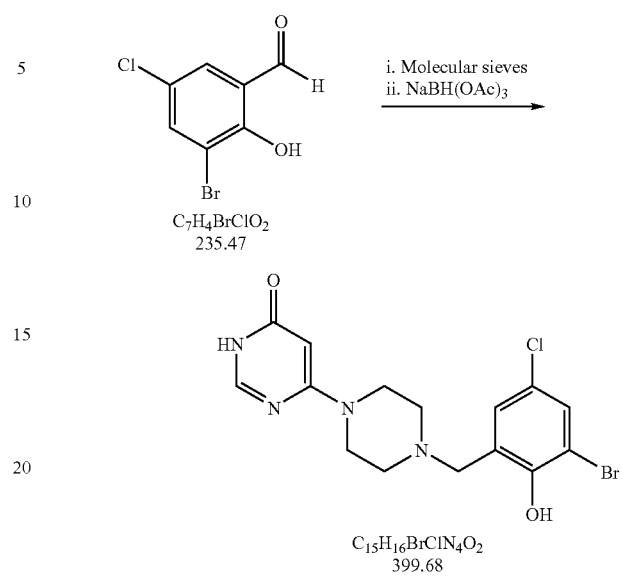

6-[4-(3-Bromo-5-chloro-2-hydroxy-benzyl)-piperazin-1-yl]-3H-pyrimidin-4-one was prepared using Procedure B from 6-piperazin-1-yl-3H-pyrimidin-4-one (Intermediate 4) and 3-bromo-5-chlorosalicylaldehyde (available from Aldrich). $^1$H NMR (400 MHz, CDCl$_3$) δ 2.62-2.66 (m, 4H), 3.48-3.66 (m, 4H), 3.72 (s, 2H), 5.40 (s, 1H), 6.93-6.94 (m, 1H), 7.44-7.45 (m, 1H), 7.86 (s, 1H), 12.85 (br s, 1H). Mass spectrum (ES) MH+=401.

Example 51

6-[4-(2-Hydroxy-5-iodo-benzyl)-piperazin-1-yl]-3H-pyrimidin-4-one

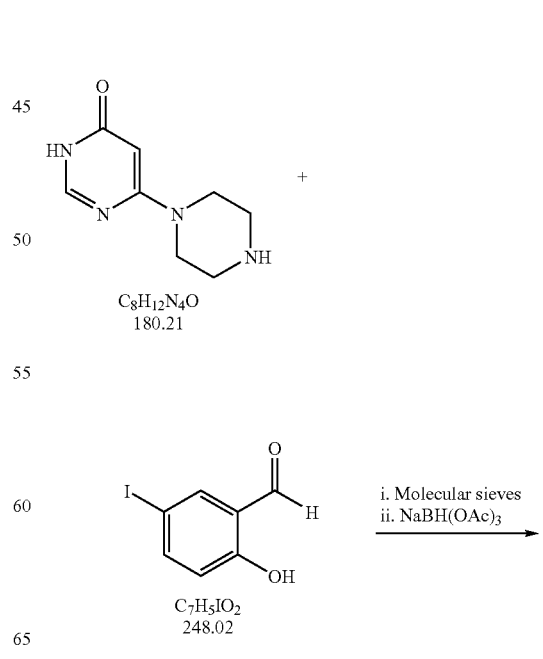

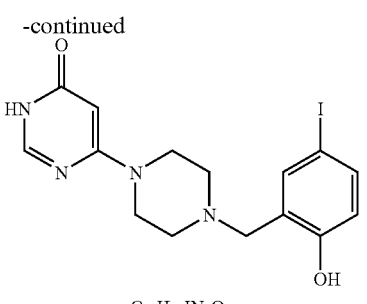

C₁₅H₁₇IN₄O₂
412.23

6-[4-(2-Hydroxy-5-iodo-benzyl)-piperazin-1-yl]-3H-pyrimidin-4-one was prepared using Procedure B from 6-piperazin-1-yl-3H-pyrimidin-4-one (Intermediate 4) and 5-iodosalicylaldehyde (available from Aldrich). $^1$H NMR (400 MHz, DMSO-d$_6$) δ 2.42-2.47 (m, 4H), 3.28-3.55 (m, 6H), 5.26 (s, 1H), 6.61-6.63 (m, 1H), 7.38-7.46 (m, 2H), 7.84 (s, 1H), 10.30 (br s, 1H), 11.63 (br s, 1H). Mass spectrum (ES) MH+=413.

Example 52

6-[4-(5-Allyl-2-hydroxy-3-methoxy-benzyl)-piper-azin-1-yl]-3H-pyrimidin-4-one

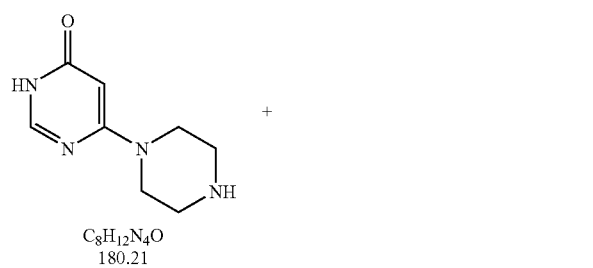

C₈H₁₂N₄O
180.21

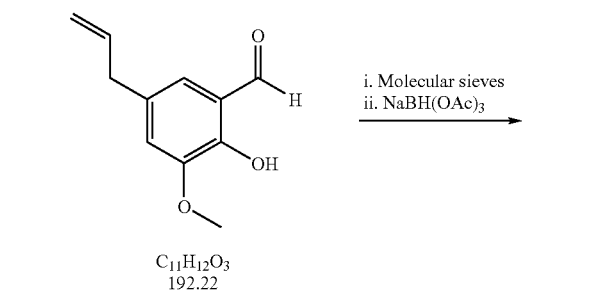

C₁₁H₁₂O₃
192.22

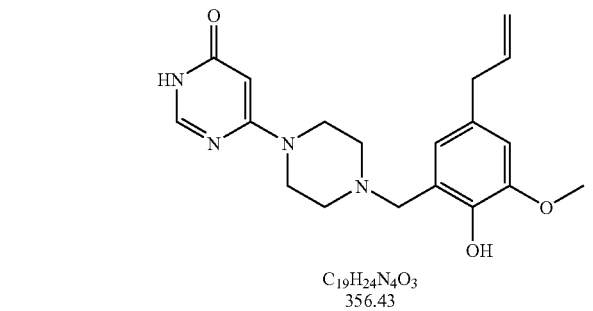

C₁₉H₂₄N₄O₃
356.43

6-[4-(5-Allyl-2-hydroxy-3-methoxy-benzyl)-piperazin-1-yl]-3H-pyrimidin-4-one was prepared using Procedure B from 6-piperazin-1-yl-3H-pyrimidin-4-one (Intermediate 4) and 5-allyl-2-hydroxy-3-methoxybenzaldehyde (available from Acros Organics, Geel, Belgium). $^1$H NMR (400 MHz, CDCl$_3$) δ 2.58-2.63 (m, 4H), 3.27-3.29 (m, 2H), 3.58-3.65 (m, 4H), 3.71 (s, 2H), 3.91 (s, 3H), 5.03-5.08 (m, 2H), 5.39 (s, 1H), 5.88-5.95 (m, 1H), 6.43 (s, 1H), 6.65 (s, 1H), 7.84 (s, 1H), 10.40 (br s, 1H), 12.80 (br s, 1H). Mass spectrum (ES) MH+=357.

Example 53

6-[4-(5-Chloro-2-hydroxy-3-methoxy-benzyl)-piperazin-1-yl]-3H-pyrimidin-4-one

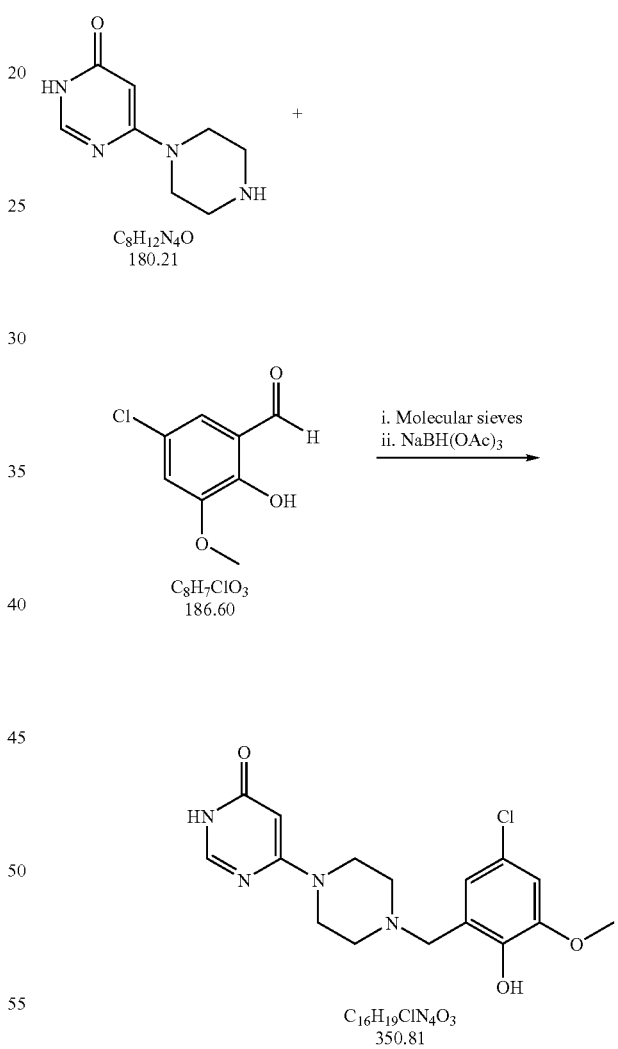

6-[4-(5-Chloro-2-hydroxy-3-methoxy-benzyl)-piperazin-1-yl]-3H-pyrimidin-4-one was prepared using Procedure B from 6-piperazin-1-yl-3H-pyrimidin-4-one (Intermediate 4) and 5-chloro-2-hydroxy-3-methoxybenzaldehyde (available from Aldrich). $^1$H NMR (400 MHz, CDCl$_3$) δ 2.50-2.55 (m, 4H), 3.60-3.66 (m, 4H), 3.70 (s, 2H), 3.88 (s, 3H), 5.39 (s, 1H), 6.61-6.62 (m, 1H), 6.80-6.81 (m, 1H), 7.84 (s, 1H), 12.40 (br s, 1H). Mass spectrum (ES) MH+=351.

Example 54

6-[4-(2-Hydroxy-5-iodo-3-methoxy-benzyl)-piperazin-1-yl]-3H-pyrimidin-4-one

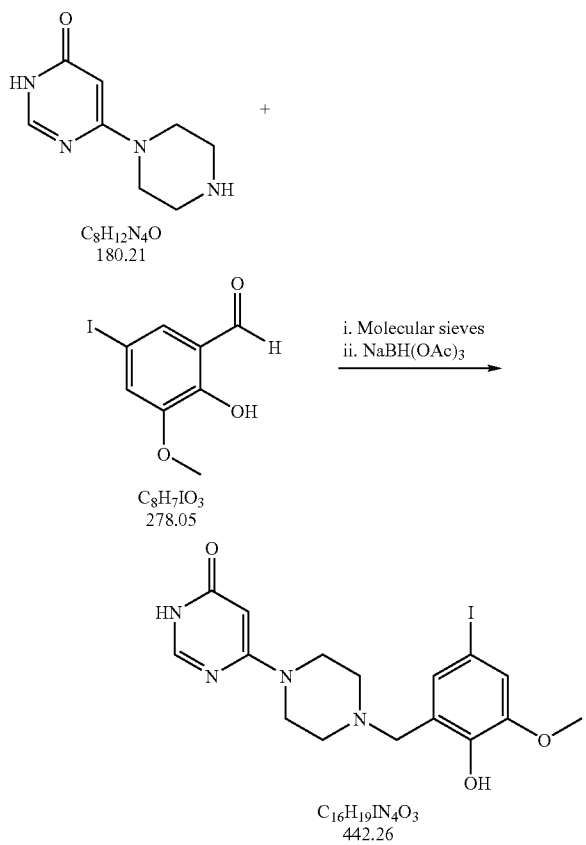

6-[4-(2-Hydroxy-5-iodo-3-methoxy-benzyl)-piperazin-1-yl]-3H-pyrimidin-4-one was prepared using Procedure B from 6-piperazin-1-yl-3H-pyrimidin-4-one (Intermediate 4) and 5-iodo-o-vanillin (available from Alfa Aesar, Ward Hill, Mass., USA). $^1$H NMR (400 MHz, CDCl$_3$) δ 2.60-2.64 (m, 4H), 3.48-3.52 (m, 4H), 3.69 (s, 2H), 3.85 (s, 3H), 5.39 (s, 1H), 6.94-6.96 (m, 1H), 7.07 (s, 1H), 7.84 (s, 1H), 12.13 (br s, 1H). Mass spectrum (ES) MH+=443.

Example 55

6-[4-(2-Hydroxy-3-methoxy-5-nitro-benzyl)-piperazin-1-yl]-3H-pyrimidin-4-one

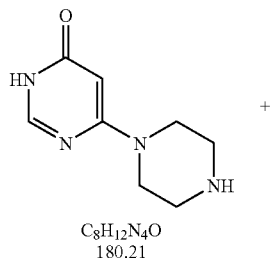

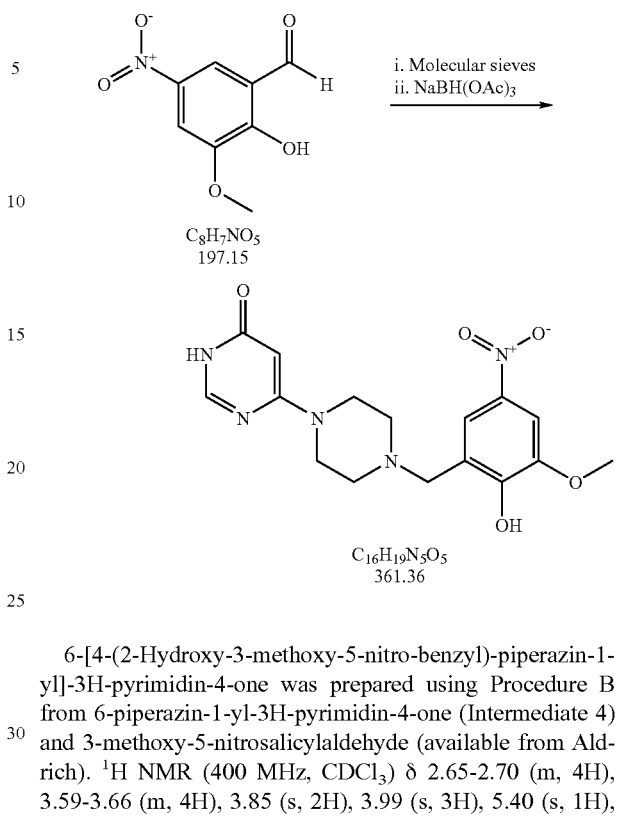

6-[4-(2-Hydroxy-3-methoxy-5-nitro-benzyl)-piperazin-1-yl]-3H-pyrimidin-4-one was prepared using Procedure B from 6-piperazin-1-yl-3H-pyrimidin-4-one (Intermediate 4) and 3-methoxy-5-nitrosalicylaldehyde (available from Aldrich). $^1$H NMR (400 MHz, CDCl$_3$) δ 2.65-2.70 (m, 4H), 3.59-3.66 (m, 4H), 3.85 (s, 2H), 3.99 (s, 3H), 5.40 (s, 1H), 7.67 (s, 1H), 7.72 (s, 1H), 7.85 (s, 1H), 12.20 (br s, 1H). Mass spectrum (ES) MH+=362.

Biological Assay

Example 56

Testing of Compounds of the Invention In Vitro

Stearoyl CoA desaturase activity was monitored by a modification of the acyl carrier protein assay described by B. R. Talamo and K. Bloch in *Anal. Biochem.* 1968, 29, 300-304. The SCD assay monitors the release of tritiated water from the desaturation of 9,10-$^3$H-stearoyl CoA.

Mouse liver microsomes, prepared from mice fed a high carbohydrate diet, were a source of the SCD and cyt b5 and cyt b5 reductase, necessary accessory proteins for the coupled reaction. Reaction mixtures for compound titrations contained 50 mM Tris HCl pH 7.5, 100 mM NaCl, 0.165 mg/ml BSA, 2.4% DMSO, 1 mM NADH, 0.03% T-20, and 300 nM (9,10) $^3$H-stearoyl CoA (Perkin-Elmer). Reactions were initiated upon the addition of 4 ug/ml SCD microsomes. Incubations were terminated after 25 minutes at room temperature with cold 6% TCA. After standing 10 minutes at 4 deg C., samples were centrifuged 15 minutes at 4000 rpm to pellet precipitated protein. Supernatants were added to microtiter plates containing suspensions of activated charcoal (Darco G-60, Fisher Scientific) and mixed by inversion. Plates were then centrifuged to separate $^3$H—H$_2$O product from charcoal-bound reactants. Supernatants were quantitated in a Perkin Elmer Topcount 384 after solubilization in ScintiSafe Plus 50% (Fisher Scientific).

Inhibition (%) of SCD activity by compounds was calculated according to the following formula:

$$\% \text{ Inhibition} = 100 * [1 - (CPM_{sample} - CPM_{blank}) / (CPM_{total} - CPM_{blank})]$$

The results of the in vitro inhibition of SCD1 by representative compounds of the present invention are shown in the following Table, wherein "A" designates an IC50 value less than or equal 1.0 µM and "B" an IC50 value greater than or equal to 1.1 µM.

| Compound | Name | IC50 |
| --- | --- | --- |
| Example 1 | 6-[4-(3-Methyl-benzyl)-piperazin-1-yl]-3H-pyrimidin-4-one | A |
| Example 2 | 6-[4-(2-Methyl-benzyl)-piperazin-1-yl]-3H-pyrimidin-4-one | A |
| Example 3 | 6-[4-(2,6-Dimethyl-benzyl)-piperazin-1-yl]-3H-pyrimidin-4-one | A |
| Example 4 | 6-[4-(2,4-Dimethyl-benzyl)-piperazin-1-yl]-3H-pyrimidin-4-one | B |
| Example 5 | 6-[4-(4-Methoxy-2,3-dimethyl-benzyl)-piperazin-1-yl]-3H-pyrimidin-4-one | B |
| Example 6 | 6-[4-(5-Bromo-2-methoxy-benzyl)-piperazin-1-yl]-3H-pyrimidin-4-one | B |
| Example 7 | 6-[4-(5-Bromo-2-hydroxy-3-methoxy-benzyl)-piperazin-1-yl]-3H-pyrimidin-4-one | A |
| Example 8 | 6-[4-(2-Trifluoromethyl-benzyl)-piperazin-1-yl]-3H-pyrimidin-4-one | A |
| Example 9 | 6-[4-(2,5-Bis-trifluoromethyl-benzyl)-piperazin-1-yl]-3H-pyrimidin-4-one | A |
| Example 10 | 3-[4-(6-Oxo-1,6-dihydro-pyrimidin-4-yl)-piperazin-1-ylmethyl]-benzonitrile | B |
| Example 11 | 2-Fluoro-5-[4-(6-oxo-1,6-dihydro-pyrimidin-4-yl)-piperazin-1-ylmethyl]-benzonitrile | A |
| Example 12 | 6-[4-(3-Chloro-benzyl)-piperazin-1-yl]-3H-pyrimidin-4-one | A |
| Example 13 | 6-[4-(3-Bromo-benzyl)-piperazin-1-yl]-3H-pyrimidin-4-one | A |
| Example 14 | 6-[4-(2,6-Dichloro-benzyl)-piperazin-1-yl]-3H-pyrimidin-4-one | B |
| Example 15 | 6-[4-(3,4-Dichloro-benzyl)-piperazin-1-yl]-3H-pyrimidin-4-one | A |
| Example 16 | 6-[4-(2,3,6-Trichloro-benzyl)-piperazin-1-yl]-3H-pyrimidin-4-one | A |
| Example 17 | 6-[4-(2,3-Dichloro-benzyl)-piperazin-1-yl]-3H-pyrimidin-4-one | A |
| Example 18 | 6-[4-(2-Bromo-benzyl)-piperazin-1-yl]-3H-pyrimidin-4-one | A |
| Example 19 | 6-[4-(5-Bromo-2-fluoro-benzyl)-piperazin-1-yl]-3H-pyrimidin-4-one | B |
| Example 20 | 6-[4-(2-Bromo-5-fluoro-benzyl)-piperazin-1-yl]-3H-pyrimidin-4-one | A |
| Example 21 | 6-[4-(3,4-Difluoro-benzyl)-piperazin-1-yl]-3H-pyrimidin-4-one | A |
| Example 22 | 6-[4-(3-Chloro-4-fluoro-benzyl)-piperazin-1-yl]-3H-pyrimidin-4-one | A |
| Example 23 | 6-[4-(2-Chloro-5-trifluoromethyl-benzyl)-piperazin-1-yl]-3H-pyrimidin-4-one | B |
| Example 24 | 6-[4-(3,5-Dichloro-2-hydroxy-benzyl)-piperazin-1-yl]-3H-pyrimidin-4-one | A |
| Example 25 | 6-[4-(5-Bromo-2-hydroxy-benzyl)-piperazin-1-yl]-3H-pyrimidin-4-one | A |
| Example 26 | 6-[4-(3-Nitro-benzyl)-piperazin-1-yl]-3H-pyrimidin-4-one | B |
| Example 27 | 6-[4-(2-Nitro-benzyl)-piperazin-1-yl]-3H-pyrimidin-4-one | A |
| Example 28 | 6-[4-(5-Chloro-2-nitro-benzyl)-piperazin-1-yl]-3H-pyrimidin-4-one | A |
| Example 29 | 6-[4-(2-Hydroxy-5-nitro-benzyl)-piperazin-1-yl]-3H-pyrimidin-4-one | A |
| Example 30 | 6-[4-(2-Hydroxy-benzyl)-piperazin-1-yl]-3H-pyrimidin-4-one | B |
| Example 31 | 6-[4-(2-Hydroxy-5-trifluoromethoxy-benzyl)-piperazin-1-yl]-3H-pyrimidin-4-one | A |
| Example 32 | 6-[4-(2-Chloro-4-fluoro-benzyl)-piperazin-1-yl]-3H-pyrimidin-4-one | B |
| Example 33 | 6-[4-(3-Fluoro-benzyl)-piperazin-1-yl]-3H-pyrimidin-4-one | B |
| Example 34 | 6-[4-(4-Bromo-2-fluoro-benzyl)-piperazin-1-yl]-3H-pyrimidin-4-one | B |
| Example 35 | 6-[4-(3-Bromo-2-methyl-benzyl)-piperazin-1-yl]-3H-pyrimidin-4-one | A |
| Example 36 | 6-(4-Biphenyl-2-ylmethyl-piperazin-1-yl)-3H-pyrimidin-4-one | B |
| Example 37 | 6-(4-Benzo[1,3]dioxol-4-ylmethyl-piperazin-1-yl)-3H-pyrimidin-4-one | B |
| Example 38 | 6-[4-(2-Hydroxy-3-methyl-benzyl)-piperazin-1-yl]-3H-pyrimidin-4-one | A |
| Example 39 | 6-[4-(2-Hydroxy-5-methyl-benzyl)-piperazin-1-yl]-3H-pyrimidin-4-one | A |
| Example 40 | 6-[4-(3-Allyl-2-hydroxy-benzyl)-piperazin-1-yl]-3H-pyrimidin-4-one | A |
| Example 41 | 6-[4-(3-tert-Butyl-2-hydroxy-benzyl)-piperazin-1-yl]-3H-pyrimidin-4-one | A |
| Example 42 | 6-[4-(3-Fluoro-2-hydroxy-benzyl)-piperazin-1-yl]-3H-pyrimidin-4-one | A |

-continued

| Compound | Name | IC50 |
|---|---|---|
| Example 43 | 6-[4-(5-Fluoro-2-hydroxy-benzyl)-piperazin-1-yl]-3H-pyrimidin-4-one | A |
| Example 44 | 6-[4-(3,5-Difluoro-2-hydroxy-benzyl)-piperazin-1-yl]-3H-pyrimidin-4-one | A |
| Example 45 | 6-[4-(3-Chloro-2-hydroxy-benzyl)-piperazin-1-yl]-3H-pyrimidin-4-one | A |
| Example 46 | 6-[4-(5-Chloro-2-hydroxy-benzyl)-piperazin-1-yl]-3H-pyrimidin-4-one | A |
| Example 47 | 6-[4-(5-Chloro-2-hydroxy-3-methyl-benzyl)-piperazin-1-yl]-3H-pyrimidin-4-one | A |
| Example 48 | 6-[4-(3-Bromo-2-hydroxy-benzyl)-piperazin-1-yl]-3H-pyrimidin-4-one | A |
| Example 49 | 6-[4-(3,5-Dibromo-2-hydroxy-benzyl)-piperazin-1-yl]-3H-pyrimidin-4-one | A |
| Example 50 | 6-[4-(3-Bromo-5-chloro-2-hydroxy-benzyl)-piperazin-1-yl]-3H-pyrimidin-4-one | A |
| Example 51 | 6-[4-(2-Hydroxy-5-iodo-benzyl)-piperazin-1-yl]-3H-pyrimidin-4-one | A |
| Example 52 | 6-[4-(5-Allyl-2-hydroxy-3-methoxy-benzyl)-piperazin-1-yl]-3H-pyrimidin-4-one | B |
| Example 53 | 6-[4-(5-Chloro-2-hydroxy-3-methoxy-benzyl)-piperazin-1-yl]-3H-pyrimidin-4-one | A |
| Example 54 | 6-[4-(2-Hydroxy-5-iodo-3-methoxy-benzyl)-piperazin-1-yl]-3H-pyrimidin-4-one | A |
| Example 55 | 6-[4-(2-Hydroxy-3-methoxy-5-nitro-benzyl)-piperazin-1-yl]-3H-pyrimidin-4-one | B |

It is to be understood that the invention is not limited to the particular embodiments of the invention described above, as variations of the particular embodiments may be made and still fall within the scope of the appended claims.

What is claimed is:

1. A compound of formula (I):

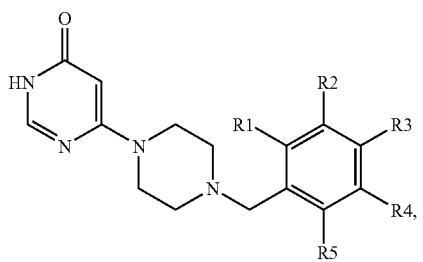

wherein:
$R^1$ and $R^5$, independently of each other, are hydrogen, unsubstituted lower alkyl, halogen, trifluoromethyl, hydroxy, aryl, alkoxy or $NO_2$;
R1 and R2, optionally, together with the carbon atoms to which they are attached, form a 9-membered ring having 1 or 2 heteroatoms;
$R^2$ and $R^4$, independently of each other, are hydrogen, unsubstituted lower alkyl, lower alkyenyl, alkoxy, halogen, cyano, trifluoromethyl, O-trifluoromethyl or $NO_2$; and
$R^3$ is hydrogen, unsubstituted lower alkyl, alkoxy or halogen;
wherein at least one of $R^1$, $R^2$, $R^3$, $R^4$ or $R^5$ is hydrogen, and pharmaceutically acceptable salts thereof.

2. The compound according to claim 1, wherein $R^1$ is halogen, $R^4$ is alkoxy and $R^5$ is hydroxy.

3. The compound according to claim 1, wherein $R^1$, $R^4$ and $R^5$ are each hydrogen.

4. The compound according to claim 1, wherein $R^2$ is halogen, $R^4$ is halogen and $R^5$ is hydroxy.

5. The compound according to claim 1, wherein both $R^2$ and $R^3$ are unsubstituted lower alkyl.

6. The compound according to claim 1, wherein both $R^2$ and $R^5$ are trifluoromethyl.

7. The compound according to claim 1, wherein both $R^3$ and $R^4$ are halogen.

8. The compound according to claim 1, wherein both $R^4$ and $R^5$ are halogen.

9. The compound according to claim 1, wherein $R^2$ is halogen and $R^3$ is hydroxy.

10. The compound according to claim 1, wherein $R^2$ is halogen and $R^5$ is $NO_2$.

11. The compound according to claim 1, wherein $R^2$ is —O-trifluoromethyl and $R^5$ is hydroxy.

12. The compound according to claim 1, wherein $R^3$ is halogen.

13. The compound according to claim 1, wherein $R^4$ is unsubstituted lower alkyl.

14. The compound according to claim 1, wherein $R^5$ is unsubstituted lower alkyl.

15. The compound according to claim 1, wherein $R^5$ is trifluoromethyl.

16. The compound according to claim 1, wherein $R^5$ is halogen.

17. The compound according to claim 1, wherein $R^5$ is $NO_2$.

18. The compound according to claim 1, wherein said compound is:
6-[4-(3-Bromo-benzyl)-piperazin-1-yl]-3H-pyrimidin-4-one;
6-[4-(5-Bromo-2-hydroxy-benzyl)-piperazin-1-yl]-3H-pyrimidin-4-one;
6-[4-(3-Chloro-benzyl)-piperazin-1-yl]-3H-pyrimidin-4-one;
6-[4-(5-Chloro-2-nitro-benzyl)-piperazin-1-yl]-3H-pyrimidin-4-one;

6-[4-(2,3-Dichloro-benzyl)-piperazin-1-yl]-3H-pyrimidin-4-one;

6-[4-(3,5-Dichloro-2-hydroxy-benzyl)-piperazin-1-yl]-3H-pyrimidin-4-one;

6-[4-(2,6-Dimethyl-benzyl)-piperazin-1-yl]-3H-pyrimidin-4-one;

6-[4-(2-Hydroxy-5-trifluoromethoxy-benzyl)-piperazin-1-yl]-3H-pyrimidin-4-one;

6-[4-(2-Nitro-benzyl)-piperazin-1-yl]-3H-pyrimidin-4-one; or

6-[4-(2-Trifluoromethyl-benzyl)-piperazin-1-yl]-3H-pyrimidin-4-one.

19. A pharmaceutical composition, comprising a therapeutically effective amount of a compound according to claim 1 or a pharmaceutically acceptable salt thereof and a pharmaceutically acceptable carrier.

* * * * *